(12) United States Patent
Gunn et al.

(10) Patent No.: US 10,946,083 B2
(45) Date of Patent: *Mar. 16, 2021

(54) ANTI-MICROBIAL IMMUNOMODULATION

(71) Applicant: Qu Biologies Inc., Burnaby (CA)

(72) Inventors: Harold David Gunn, Vancouver (CA); Salim Dhanji, North Vancouver (CA); David W. Mullins, Lebanon, NH (US)

(73) Assignee: Qu Biologies Inc., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,040

(22) Filed: Jan. 31, 2019

(65) Prior Publication Data

US 2019/0247484 A1  Aug. 15, 2019

Related U.S. Application Data

(63) Continuation of application No. 15/308,302, filed as application No. PCT/CA2015/050377 on May 1, 2015, now Pat. No. 10,251,946.

(60) Provisional application No. 61/988,117, filed on May 2, 2014.

(51) Int. Cl.
  *A61K 39/108* (2006.01)
  *A61K 39/00* (2006.01)

(52) U.S. Cl.
  CPC ...... *A61K 39/0266* (2013.01); *A61K 39/0258* (2013.01); *A61K 2039/521* (2013.01); *A61K 2039/54* (2013.01); *A61K 2039/541* (2013.01); *A61K 2039/545* (2013.01); *A61K 2039/55* (2013.01); *A61K 2039/57* (2013.01); *A61K 2039/58* (2013.01); *Y02A 50/30* (2018.01)

(58) Field of Classification Search
  None
  See application file for complete search history.

(56) References Cited

U.S. PATENT DOCUMENTS

| | | | |
|---|---|---|---|
| 3,928,565 A | 12/1975 | Homma et al. | |
| 4,329,452 A | 5/1982 | Maruyama | |
| 4,880,626 A | 11/1989 | McMichael | |
| 5,652,332 A | 7/1997 | Little, II | |
| 5,869,057 A | 2/1999 | Rock | |
| 6,348,586 B1 | 2/2002 | Chang et al. | |
| 6,447,777 B1 | 9/2002 | Terman et al. | |
| 6,902,743 B1 | 6/2005 | Setterstrom et al. | |
| 7,018,629 B2 | 3/2006 | Jacob et al. | |
| 8,034,359 B2 | 10/2011 | Gunn | |
| 8,501,198 B2 | 8/2013 | Gunn | |
| 9,107,864 B2 | 8/2015 | Gunn | |
| 9,974,848 B2 | 5/2018 | Sampson et al. | |
| 10,130,692 B2 * | 11/2018 | Gunn | A61K 39/0275 |
| 10,251,946 B2 * | 4/2019 | Gunn | A61P 31/12 |
| 2002/0044948 A1 | 4/2002 | Khleif et al. | |
| 2003/0059400 A1 | 3/2003 | Szalay | |
| 2003/0073628 A1 | 4/2003 | Shailubhai et al. | |
| 2004/0014661 A1 | 1/2004 | Goetsch et al. | |
| 2005/0070463 A1 | 3/2005 | Libon et al. | |
| 2005/0175630 A1 | 8/2005 | Raz et al. | |
| 2006/0127411 A1 | 6/2006 | Neuber | |
| 2006/0147477 A1 | 7/2006 | Cabezon Siliva et al. | |
| 2007/0134264 A1 | 6/2007 | Marshall | |
| 2009/0074816 A1 | 3/2009 | Gunn | |
| 2010/0099600 A1 | 4/2010 | Ny et al. | |
| 2011/0020401 A1 | 1/2011 | Gunn | |
| 2017/0087237 A1 | 3/2017 | Gunn et al. | |
| 2017/0368166 A1 | 12/2017 | Gunn | |
| 2018/0050099 A1 | 2/2018 | Gunn et al. | |
| 2019/0247484 A1 * | 8/2019 | Gunn | A61P 31/04 |

FOREIGN PATENT DOCUMENTS

| | | | |
|---|---|---|---|
| CA | 2571805 A1 | 4/2008 | |
| EP | 1415655 A1 | 5/2004 | |
| GB | 2370770 A | 7/2002 | |
| JP | S54129117 A | 10/1979 | |
| JP | S56108716 A | 8/1981 | |
| JP | S5839624 A | 3/1983 | |
| JP | S6012071 A | 1/1985 | |
| JP | 2002-509888 A | 4/2002 | |
| JP | 2004-067541 | 3/2004 | |
| JP | 2006-131623 | 5/2006 | |
| JP | 2006-524703 A | 11/2006 | |
| JP | 2009-537547 A | 10/2009 | |
| WO | WO 9323079 A1 | 11/1993 | |
| WO | WO 1995/26742 A | 10/1995 | |
| WO | WO9832452 A1 | 7/1998 | |
| WO | WO 01/56387 A1 | 8/2001 | |
| WO | WO 0211713 A2 | 2/2002 | |
| WO | WO 2002/023994 A1 | 3/2002 | |
| WO | WO 02074939 A1 | 9/2002 | |
| WO | WO 03/009859 A1 | 2/2003 | |
| WO | WO 03/049752 A2 | 6/2003 | |
| WO | WO 2003/049751 A | 6/2003 | |
| WO | WO 03045333 A2 | 6/2003 | |
| WO | WO 2003/063593 A1 | 8/2003 | |
| WO | WO 03104272 A1 | 12/2003 | |

(Continued)

OTHER PUBLICATIONS

Abel et al. Common infections in the history of cancer patients and controls. J Cancer Res Clin Oncol. 1991; 117(4):339-344.

Abramson et al. Relationship between physical activity and inflammation among apparently healthy middle-aged and older US adults. Arch Intern Med. 2002;162(11):1286-1292.

(Continued)

*Primary Examiner* — Nita M. Minnifield
(74) *Attorney, Agent, or Firm* — Bret E. Field; Bozicevic, Field & Francis LLP

(57) ABSTRACT

The invention provides methods of modulating an immune system in a vertebrate host for the therapeutic or prophylactic treatment of infection by a first microbial pathogen in a target tissue, comprising administration at an administration site of an effective amount of an antigenic formulation comprising antigenic determinants specific for a second heterologous microbial pathogen.

20 Claims, 17 Drawing Sheets

(56) References Cited

FOREIGN PATENT DOCUMENTS

| WO | WO 2004064717 A2 | 8/2004 |
|---|---|---|
| WO | WO 2004069256 A1 | 8/2004 |
| WO | WO 2005/049056 A2 | 6/2005 |
| WO | WO 2005/099750 A1 | 10/2005 |
| WO | WO 2005/120560 A1 | 12/2005 |
| WO | WO 2008/049231 A1 | 5/2008 |
| WO | WO 2009013443 A1 | 1/2009 |
| WO | WO 2009/021977 A1 | 2/2009 |
| WO | WO2009027753 A1 | 3/2009 |
| WO | WO 2010/068413 A1 | 6/2010 |
| WO | WO 2012012874 A1 | 2/2012 |

OTHER PUBLICATIONS

Ajani et al. Dietary fiber and c-reactive protein: Findings from National Health and Nutrition Examination Survey Data. 2004;134:1181-5.
Akre et al. Aspirin and risk for gastric cancer: a population-based case-conrol study in Sweden. Br J Cancer 2001;84:965-968.
Al-Ahaideb. 2008 (Septic arthritis in patients with rheumatoid arthritis; Journal of Orthopaedic Surgery and Research; 3:33-36).
Asadullah et al. Interleukin-10 therapy—review of a new approach. Pharmacol Rev 2003;55:241.
Assersohn et al., "A Randomized Pilot Study of SRL172 (*Mycobaterium vaccae*) in Patients with Small Cell Lung Cancer (SCLC) Treated with Chemotherapy" Clinical Oncology (2002) 14: 23-27.
Baer et al. Dietary fatty acids affect plasma markers of inflammation in healthy men fed controlled diets: A randomized crossover study. Am J Clin Nutr 2004;79:969-73.
Balch et al., A randomized prospective trial of adjuvant C. parvum immunotherapy in 260 patients with clinically localized melanoma (stage I), Cancer 49(6): 1079-1084 (Mar. 15, 1982).
Balkwill et al. Cancer Cell (2005) 7,211-217.
Balkwil et al. Inflammation and cancer: back to Virchow? Lancet 2001;357:539.
Baron et al. Nonsteroidal anti-inflammatory drugs and cancer prevention. Annu Rev Med 2000;51:511-23.
Barreda et al. Regulation of myeloid development and function by colony stimulating factors. Dev Comp Immunol 2004;28:509.
Bast et al., "Immunostimulants", Holland-Free Cancer Medicine 5$^{th}$ Edition—NCBI Bookshelf; http://www.ncbi.nlm.nih.gov/bookshelf.br.togi?book-cmed&part-A13924; 20 pp (2000).
Beaman et al., Effect of growth stage on mycolic acid structure in cell walls of Nocardia asteroides GUH-2. Journal of Bacteriology 1988; 170(3): 1137-1142.
Beatty et al., "CD40 Agonists Alter Tumor Stroma and Show Efficacy Against Pancreatic Carcinoma in Mice and Humans", Science (2011) vol. 331, pp. 1612-1616.
Behr et al. Comparative genomics of BCG vaccines by whole genome microarray. Science 1999; 284: 1520-1523.
Ben-Baruch. Breast cancer progression: a vicious cycle of pro-malignancy activities is mediated by inflammatory cells, chemokines and cytokines. Kluwer Academic Publishers; 2005.
Ben-Baruch. Host microenvironment in breast cancer development: inflammatory cells, cytokines and chemokines in breast cancer progression: reciprocal tumor-microenvironment interactions. Breast Cancer Res 2003;5:31.
Ben-Baruch. Inflammation-associated immune suppression in cancer: The roles played by cytokines, chemokines and additional mediators. Seminars in Cancer Biology 16(2006)38-52.
Beuth et al. Modulation of murine tumor growth and colonization by bromelaine, an extract of the pineapple plant (Ananas comosum) In Vivo Mar.-Apr. 2005;19(2):483-5.
Bierman et al. Remissions in acute leukemia of childhood following actue infectious disease. Cancer 1953;6:591-605.
Bingham. The fibre-folate debate in colo-rectal cancer. Proc. Nutr. Soc. Feb. 2006;65(1):19-23.
Bingle et al. Pathol. (2002) 196,254-65.

Biswas et al. "Macrophage plasticity and interaction with lymphocyte subsets: cancer as a paradigm", Nature Immunology (2010) vol. 11, No. 10, pp. 889-896.
Bouchardy et al. Cancer risk by occupation and socioeconomic group among men—a study by the Association of Swiss Registries. Scand J Work Environ Health 2002;28(Suppl 1):1-88.
Braat et al., "Prevention of experimental colitis by parenteral administration of a pathogen-derived immunomodulatory molecule" Colonic Inflammation Gut. (2007) vol. 56, No. 3; pp. 351-357.
Brigati et al. Tumors and inflammatory infiltrates: friends or foes? Clin Exp Metastasis 2002;19:247.
Brown-Elliott et al. Clinical and laboratory features of the *Nocardia* spp. Based on current molecular taxonomy. Clinical Microbiology Reviews 2006; 19(2): 259-282.
Brunda et al., "Immunotherapy of the guinea pig line 10 hepatocarcinoma with a variety of nonviable bacteria", Cancer Research, 1980, 40(9):3211-3213.
Bruun et al. Diet and exercise reduce low-grade inflammation and macrophage infiltration in adipose tissue but not in skeletal muscle in severely obese subjects. Article in Press. AM J Physiol Endocrinol Metab (Dec. 12, 2005) D01:10.1152/ajpendo.00506.2005.
Buhtoiarov et al., "Anti-tumour synergy of cytotoxic chemotherapy and anti-CD40 plus CpG-ODN immunotherapy through repolarization of tumour-associated macrophages", Immunology (2011) vol. 132, No. 2, pp. 226-239.
Busse et al., "Influence of Cyclic AMP Level and Interferon Level in the Lymphocytes and Change in the Rate of Taking Root of the Tumor of a Transplantable Melanoma of the Syrian Hamster by Treatment with BCG Measles Vaccine as well as L Dopa and Amantadine", Radiobiologia Radiothfrapia. vol. 21, No. 3 (1980) pp. 292-301. (German Translation).
Butler et al. Epidemiology of pneumococcal infections in the elderly. Drugs Aging 1999;15(Suppl 1):11-9.
Chakrabarty, "Microorganisms and Cancer: Quest for a Therapy" Journal of Bacteriology, (2003), vol. 185, pp. 2683-2686.
Chang et al., "Macrophage Arginase Promotes Tumor Cell Growth and Suppresses Nitric Oxide-mediated Tumor Cytotoxicity", Cancer Research (2001) vol. 61, pp. 1100-1106.
Cheng et al. Clinical trial of Corynebacterium parvum (intra-lymphnode and intravenous) and radiation therapy in the treatment of head and neck carcinoma. Cancer Jan. 15, 1982;49(2):239-44.
Cole. Efforts to explain spontaneous regression of cancer. J Surg Oncol. 1981; 17:201-209.
Cole. Spontaneous regression of cancer and the importance of finding its cause. NCI Monogr. 1976; 44:5-9.
Coley. Late results of the treatment of inoperable sarcoma by the mixed toxins of erysipelas and Bacillus prodigiosus. Am J Med Sci 1906; 131:375-430.
Coley. The treatment of inoperable sarcoma by bacterial toxins (the mixed toxins of the streptococcus of erysipelas and th bacillus prodigiosus). Practitioner 1909;83:589-613.
Coley. The treatment of malignant tumors by repeated inoculations of erysipelas: with a report of ten original cases.Am J Med Sci 1893; 105:487-511.
Comeri et al. Role of BCG in T1G3 bladder transitional cell carcinoma (TCC): our experience. Arch Urol Ital Androl Feb. 1996; 68(1):55-9.
Comes et al. IFN-gamma-independent synergistic effects of IL-2 and IL-15 induce anti-tumour immune responses in syngeneic mice. Eur J Immunol 2002;32:1914.
Condeelis et al. Macrophages: Obligate partners for tumor cell migration, invasion, and metastasis. Cell 124 Jan. 27, 2006 263-6.
Condeelis et al. Intravital imaging of cell movement in tumours. Nat Rev Cancer 3(2003)921-930.
Cosenza et al. "Metastasis of hepatocellular carcinoma to the right colon manifested by gastrointestinal bleeding", Am. Surg., 1999, 65(3): 218-21.
Cotterchio et al. Nonsteroidal anti-inflammatory drug use and breast cancer risk. Cancer Epidemiol Biomarkers Prev 2001;10:1213-1217.
Coussens et al., "Inflammation and Cancer", Nature (2002) 420(6917):860-867.

(56) References Cited

OTHER PUBLICATIONS

Creasman et al. A randomized trial of cyclophosphamide, doxorubicin, and cisplatin with and without BCG in patients with suboptimal stage III and IV ovarian cancer: a Gynecologic Oncology Group study. Gynecol Oncol 1990; 39:239-243.
Crowther et al. Microenvironmental influence on macrophage regulation of angiogenesis in wounds and malignant tumors. J Leukoc Biol 2001;70:478.
Curiel et al. Specific recruitment of regulatory T cells in ovarian carcinoma fosters immune privilege and predicts reduced survival. Nat Med 2004;10:942-949.
Daum et al. Mortality experience of a cohort of cotton textile workers. Final progress report on Contract No. HSM 99-72-71 (NIOSH), Mar. 1, 1975.
Davidson. Carcinoma and malaria. Br. Med J 1902;1:77.
De Visser et al. The Inflammatory Tumor Microenvironment and its Impact on Cancer Development. Dittmar T, Jaenker KS, Schmidt A (eds): Infection and Inflammation: Impacts on Oncogenesis. Contrib Microbiol Basel, Karger, 2006, vol. 13,118-137.
De Visser et al. De novo carcinogenesis promoted by chronic inflammation is B lymphocyte dependent. Cancer Cell 2005;7:411-423.
Dechsupa et al. Siamois 1 and Siamois 2 Induce Apoptosis in Human Breast Cancer MDA-MB-435 Cells Xenograft In Vivo. Cancer Biol Ther. Jan. 29, 2007;6(1).
Dempke et al. Cyclooxygenase-2: a novel target for cancer chemotherapy? J Cancer Res Clin Oncol 2001;127:411.
Derynck et al. TGFβsignaling in tumor suppression and cancer progression. Nat Genet 2001;29:117.
Di Carlo et al. Immunological mechanisms elicited at the tumour site by lymphocyte activation gene-3 (LAG-3) versus IL-12: sharing a common Th1 anti-tumour immune pathway. J Pathol 2005;205:82.
Fisher et al. Evaluation of the worth of corynebacterium parvum in conjunction with chemotherapy as adjuvant treatment for primary breast cancer. Eight-year results from the National Surgical Adjuvant Breast and Bowel Project B-10 Cancer Jul. 15, 1990;66(2)220-7.
Disaia et al. Phase III study on the treatment with cervical cancer stage IIB, IIIB, and IVA, with radiotherapy alone versus radiotherapy plus immunotherapy with intravenous Corynebacterium parvum: a Gynecologic Oncology Group Study. Gynecol Oncol Mar. 1987;26(3)386-97.
Dock. The influence of complicating diseases upon leukemia. Am J Med Sci. 1904; 127:563-592.
Dumont et al. Targeting the TGFβsignaling network in human neoplasia. Cancer Cell 2003;3:531.
Dumont et al. Transforming growth factor-βand breast cancer: Tumor promoting effects of transforming growth factor-β. Breast Cancer Res 2000;2:125.
Eichenwald et al. Acute diarrheal disease. Med Clin N Am 1970;54:443-54.
Elegbede et al. (1993) Effects of anticarcinogenic monoterpenes on phase II hepatic metabolizing enymes. Carcinogenesis 14:1221-3.
Elgert et al. Tumor-induced immune dysfunction: the macrophage connection. J Leukoc Biol 1998; 64: 275-290.
Elliott et al., "Clearance of apoptotic cells: implications in health and disease", J. Cell Biol. (2010) vol. 189, No. 7, pp. 1059-1070.
Elosua et al. Association between physical activity, physical performance, and inflammatory biomarkers in an elderly population: The InCHIANTI Study. J Gerontology: Medical Sciences 2005;60A(6);760-67.
Enterline et al. Endotoxins, cotton dust and cancer. Lancet 1985;2:934-5.
Erb et al., "Clinical and Technical Considerations for Imaging Colorectal Cancers with Technetium-99m-Labeled AntiCEA Fab' Fragment", J Nucl Med Technol, 2000, 28(1): 12-18.
Everson et al. Spontaneous regression of cancer. A study and abstract of reports in the world medical literature and personal communications concerning spontaneous regression of malignant disease. W.B Saunders Co. Philadelphia. 1966.
Everson et al. Spontaneous regression of cancer: Preliminary report. Ann Surgery. 1966; 144:366-383.
Everson. Spontaneous regression of cancer. Ann New York Acad Sci. 1964; 114: 721-735.
Fenton et al. "Induction of T-cell immunity against Ras oncoproteins by soluble protein or Ras-expressing *Escherichia coli*", J Natl Cancer Inst, 1995, 87(24): 1853-1861.
First Examination Report dated Sep. 14, 2010 for Indian Patent Application No. 119/KOLNP/2007.
Fisher et al. "Evaluation of the worth of crynebacterium parvum in conjunction with chemotherapy as adjuvant treatment for primary breast cancer. Eight-year results from the National Surgical Adjuvant Breast and Bowel Project B-10" Cancer (Jul. 15, 1990) 66(2):220-7.
Friedman et al. (1987): Distinctive immunomodulatory effects of endotoxin and nontoxic lipopolysaccharide derivatives in lymphoid cell cultures J Biol Response Mod 6(6):664-77.
Gablzon et al. Contrasting effects of activated and nonactivated macrophages and macrophages from tumor-bearing mice on tumor growth in vivo. J Natl Cancer Inst 1980;65913-20.
Gao et al. Plasma c-reactive protein and homocystine concentrations are related to feqeunt fruit and vegetable intake in Hispanic and non-Hispanic white elders. J Nutr 2004;134:913-8.
Garcia-Hernandez et al. Interleukin 10 promotes B 16-melanoma growth by inhibition of macrophage functions and induction of tumour and vascular cell proliferation. Immunology 2002;105:231.
Garcia-Rodriquez et al. Reduced risk of colorectal cancer among long-term users of aspirin and nonaspirin nonsteroidal anti-inflammatory drugs. Epidemiology 2001;12:88-93.
Garland et al. The role of vitamin D in cancer prevention. Am J Public Heath Feb. 2006(96)252-61.
Gaynor. (2003) One Oncologist's view of integrative care: Keynote address, Comprehensive Cancer Care Conference. Integrative Cancer Therapies 3(1):82-87.
Gersemann et al., "Innate immune dysfunction in inflammatory bowel disease", Journal of Internal Medicine (2012) vol. 271, No. 5, pp. 421-428.
Goede et al. Induction of inflammatory angiogenesis by monocyte chemoattractant protein-1. Int J Cancer 1999;82:765.
Gottke et al. Hepatitis in disseminated bacillus Calmette-Guerin infection. Can J Gastroenterol 2000; 14:333-6.
Graham. The epidemiology of acute respiratory infections in children and adults: a global perspective. Epidemiol Rev 1990;12:149-78.
Grant. Epidemiology of disease risks in relation to vitamin D insufficiency. Prog Biophys Mol Biol 2006 92(1)65-79.
Grossarth-Maticek et al. Reported Herpes-virus infection, fever and cancer incidence in a prospective study. J Chronic Dis. 1987; 40:967-976.
Grosso et al. MUC1/sec-espressing tumors are rejected in vivo by a T cell-dependent mechanism and secrete high levels of CCL@. J Immunol 2004;173:1721.
Gutierrez. 2005 (Bone and Joint Infections in Children; Pediatr. Clin N Am. 52:779-794).
Hachem et al., Cutaneous and pulmonary infections caused by Mycobacterium vaccae. Clin Infect Dis. Jul. 1996;23(1):173-5.
Hadden. Immunodeficiency and cancer: prospects for correction. Int Immunopharmacol 2003;2:1061.
Haldane. The co-existence of tubercle and cancer. Edinburgh Med J 1862;8:343-9.
Hanada et al. Prognostic value of tumor-associated macrophage count in human bladder cancer. Int J Urol. 2000; 7:263-9.
Hanaue et al., Hemolytic streptococcus preparation OK-432; beneficial adjuvant therapy in recurrent gastric carcinoma, Tokai J Exp Clin Med 12(4): 209-214 (Nov. 1987).
Harper-Wynne et al., Addition of SRL 172 to standard chemotherapy in small cell lung cancer (SCLC) improves symptom control, Lung Cancer 47(2):289-290 (Feb. 2005).
Harris et al. Prostaglandins as modulators of immunity. Trends Immunol 2002;23:144.
Havas et al. (1993) Clinical Results and immunologic effects of a mixed bacterial vaccine in cancer patients. Med Oncol. & Tumour Pharmachother. 10(4):145-58.

(56) References Cited

OTHER PUBLICATIONS

Hemminki et al. Socioeconomic factors in cancer in Sweden. Int J Cancer 2003;105:692-700.
Hewitt et al. Exercise for breast cancer survival: the effect on cancer risk and cancer-related fatigue. Int J Fertil Womens Med Sep.-Oct. 2005;50(5 Pt 1):231-9.
Higgins et al., Virus therapy in the treatment of tumors, Bull Hosp Joint Dis 12:379-382 (1951).
Hobohm. Fever therapy revisited. British Journal of Cancer 2005; 92: 421-425.
Hoffman. The mortality from cancer in the Western hemisphere. J Cancer Res. 1916;1:21-48.
Holmes et al. Physical activity and survival after breast cancer diagnosis. JAMA. May 25, 2005;293(20):2479-86.JAMA May 25, 2005;293(20):2479-86.
Homem de Bittencourt et al. Antiproliferative prostaglandins and the MRP/GS-X pump role in cancer immuno-suppression and insight into new strategies in cancer gene therapy. Biochem Pharmacol 2001;62:811.
Hoption Cann et al. Spontaneous Remission of Pancreatic Cancer. Case Rep Clin Prac Rev 2004;5:293-6.
Hoption Cann et al. (2003) Dr. William Coley and tumour regression: a place in history or in the future? Postgrad Med J 2003;79:672-680.
Hoption Cann et al. Acute infections as a means of cancer prevention: Opposing effects to chronic infections? Cancer Detection and Prevention 30(2006)83-93.
Hrouda et al., "Immunotherapy of advanced prostate cancer: a phase I/II trial using Mycobacterium caccae (SRL172)" British Journal of Urology (1998) vol. 82, No. 4 pp. 568-573.
Interview Summary dated May 9, 2011 for U.S. Appl. No. 12/234,569 (4 pp.).
Jeannin et al., "OmpA targets dendritic cells, induces their maturation and delivers antigen into the MHC class I presentation pathway", Nature Immunology, 2000, 1(6): 502-509.
Jensen et al., "Macrophage Markers in Serum and Tumor Have Prognostic Impact in American Joint Committee on Cancer Stage I/II Melanoma", Journal of Clinical Oncology (2009) vol. 27, No. 20, pp. 3330-3337.
Jian et al. Protective effects of green tea against prostate cancer: a case-control study in southeast China. Int J Cancer Jan. 1, 2004;108(1)130-5.
Johansson et al. Epidemiology and etiology of bladder cancer. Semin Surg Oncol 1997;13:291-8.
Johnston. Clinical effects of Coley's Toxins. I. Controlled study. II. A seven-year study. Cancer Chemotherapy Reports1962; 21:19-48.
Josefsson et al. 2001 (Protection against experimental *Staphylococcus aureus* arthritis by vaccination with clumping factor A, a voel virulence determinant; J of Infect. Dis. 184:1572-80).
Jurincic-Winkler et al. Effect of keyhole limpet hemocyanin (KLH) and bacillus Calmette-Guerin (BCG) instillation on carcinoma in situ of the urinary bladder. Anticancer Res Nov.-Dec. 1995; 15(66): 2771-6.
Kapp. Microorganisms as antineoplastic agents in CNS tumors. Arch Neurol. 1983; 40:637-642.
Kassabov et al., "Inhibition of spontaneous pulmonary metastases of Lewis lung carcinoma by oral treatment with Respivax and Broncho-Vaxom", Cancer Immunol Immunother (1991) 33(5): 307-313.
Kelemen et al. Vegetables, fruit, and antioxidant-related nutrients and risk of non-Hodgkin lymphoma: a National Cancer Institute—Surveillance, Epidemiology, and End Results population-based case-control study. Am J Clint Nutr Jun. 2006;83(6):1401-10.
Keller et al. Cell Immunol 134(1991)249-55.
Keller et al. Lymphokines and bacteria, that induce tumoricidal activity, trigger a different secretory response in macrophages. Eur J Immunol Mar. 1990b; 20(3):695-8.
Keller et al. Coordinate up- and down-modulation of inducible nitric oxide synthase, nitric oxide production, and tumoricidal activity in rat bone-marrow-derived mononuclear phagocytes by lipopolysaccharide and gram-negative bacteria. Biochem Biophys Res Commun 1995;211:183-9.
Keller et al. J. Immunol 138(1987)2366-71.
Khan et al., "Oxidised lipoproteins may promote inflammation through the selective delay of engulfment but not binding of apoptotic cells by macrophages", Atherosclerosis (2003) vol. 171, pp. 21-29.
Kizaki et al. Spontaneous remission in hypoplastic acute leukemia. Keio J Med 1988; 37:299-307.
Kleef et al., "Endotoxin and Exotoxin Induced Tumor Regression with Special Reference to Coley Toxins: A Survey of the Literature and Possible Immunological Mechanisms", Report to the National Cancer Institute Office of Alternative and Complementary Medicine (Aug. 1997).
Kolmel et al., "Prior immunization of patients with malignant melanoma with vaccinia of BCG is associated with better survival. An European Organization for Research and Treatment of Cancer cohort study on 542 patients", Eur J Cancer 41:118-125 (2005).
Kolmel et al. Treatment of advanced malignant melanoma by a pyrogenic bacterial lysate: a pilot study, Onkologie 14:411-417 (1991).
Kolmel et al. Febrile infections and malignant melanoma: results of a case-control study. Melanoma Res. 1992; 2:207-211.
Korzenik, "Is Crohn's disease due to defective immunity?", Gut. (2007) vol. 56, No. 1, pp. 2-5.
Kurzrock. Cytokine deregulation in cancer. Biomed Pharmacother 2001;55:543.
Lee et al. Angiogenesis and inflammation in invasive carcinoma of the breast. J Clin Pathol 1997;50:669.
Leek et al. Tumor-associated macrophages in breast cancer. J Mammary Gland Biol Neoplasia 2002;7:177.
Leek et al. Macrophage infiltration is associated with VEGF and EGFR expression in breast cancer. J Pathol 2000;190:430.
Leek et al. Necrosis correlates with high vascular density and focal macrophage infiltration in invasive carcinoma of the breast. Br. J Cancer 1999;79:991.
Lewis et al. Cytokine regulation of angiogenesis in breast cancer: the role of tumor-associated macrophages. J Leukoc Biol 1995;57:747.
Lewis et al. Expression of vascular endothelial growth factor by macrophages is up-regulated in poorly vascularized areas of breast carcinomas. J Pathol 2000;192:150.
Li et al. A clinical study on PA_MSHA vaccine used for adjuvant therapy of lymphoma and lung cancer, Hua Xi Vi Ke Da Xue Xue Bao 31(3):334-337 (Sep. 2000).
Likhite, "Rejection of Tumors and Metastases in Fischer 344 Rats Following Intratumor Administration of Killed Corynebacterium Parvum", Int. J. Cancer 14: 684-690 (1974).
Lin et al. J Mammary Gland Biol Neoplasia 7(2002)147-162.
Liu et al. Relation between a diet with a high glycemic load and plasma concentrations of high-sensitivity c-reactive protein in middle-aged women. Am J Clin Nutr 2002;75(3):492-8.
Luboshits et al Elevated expression of the CC chemokine regulated on activation, normal T cell expressed and secreted (RANTES) in advanced breast carcinoma. Cancer Res 1999;59:4681.
Ludwig Lung Cancer Study Group. Adverse effect of intrapleural Coryebacterium parvum as adjuvant therapy in resected stage I and II non-small-cell carcinoma of the lung. J Thorac Cardiovasc Surg 1985; 89: 842-847.
Lunet et al. Fruit and vegetables consumption and gastric cancer: a systemic review and meta-analysis of cohort studies. Nutr. Cancer 2005;53(1):1-10.
Ma et al., "The M1 form of tumor-associated macrophages in non-small cell lung cancer is positively associated with survival time", BMC Cancer (2010) vol. 10, No. 112, pp. 1-9.
MacLean et al., "Vaccination strategies for the prevention of cervical cancer" Expert Review of Anticancer Therapy, Future Drugs, London (2005) vol. 5, No. 1.
Mager, "Bacteria and Cancer: Cause, Coincidence or Cure? A Review." Journal of Translational Medicine 5 Mar. 28, 2006 4[14]:doi:10.1186/1479-5876-4-14.

(56) References Cited

OTHER PUBLICATIONS

Malmberg. Effective immunotherapy against cancer: a question of overcoming immune suppression and immune escape? Cancer Immunol Immunother 2004;53:879.

Mantovani et al. Tumour-associated macrophages as a prototypic type II polarized phagocyte population: role in tumour progression. Eur J Cancer 2004;40:1660.

Mantovani et al. Chemokines in the recruitment and shaping of the leukocyte infiltrate of tumors. Semin Cancer Biol 2004;14:155.

Mantovani et al. Macrophage polarization: Tumour-associated macrophages as a paradigm for polarized M2 mononuclear phagocytes. Trends Immunol 2002;23:549.

Mantovani et al., "Macrophages, innate immunity and cancer: balance, tolerance, and diversity", Current Opinion in Immunology (2010) vol. 22, No. 2, pp. 231-237.

Marks et al., "Crohn's Disease: an Immune Deficiency State", Clinic. Rev. Allerg. Immunol. (2010) vol. 38, pp. 20-31.

Marks et al., "Defective acute inflammation in Crohn's disease: a clinical investigation", Lancet (2006) vol. 367, pp. 668-678.

Marks, "Defective innate immunity in inflammatory bowel disease: a Crohn's disease exclusivity?" Current Opinion in Gastroenterology (2011) vol. 27, pp. 328-334.

Mastrangelo et al. Cancer increased after a reduction of infections in the first half of this century in Italy: etiologic and preventive implications. Eur J. Epidemiol 1998;14:749-54.

Mastrangelo et al. Reduced lung cancer mortality in dairy farmers: is endotoxin exposure they key factor? Am J Ind Med 1996;30:601-9.

Matzker et al. Tonsillectomy and leukemia in adults (author's transl). Laryngol Rhinol Otol (Stuttg). 1976; 55:721-5.

Maurya et al. (1991) Differential induction of glutathione transferase isoenzymes of mice stomach by diallyl sulfide, a natural occurring anticarcinogen. Cancer Lett. 57:121-9.

Meier et al. Association between acetaminophen or nonsteroidal anti-inflammatory drugs and risk of developing ovarian, breast, or colon cancer. Pharmacotherapy 2002;22:303-309.

Melbye et al. Human papillomavirus and the risk of anogenital cancer. Ugeskr Laeger 2002;164:5950-3.

Merchant et al. Mortality of employees of two cotton mills in North Carolina. Chest 1981;79:6s-11S.

Mihich et al. Necrotizing effects of *Staphyloccus aureus* extract on mouse sarcoma, Proc Soc Exp Bioi Med 106:97-101 (1961).

Moore et al. Interleukin-10 and the interleukin-10 receptor. Annu Rev Immunol 2001;19:683.

Morales et al. (1992b). Immunotherapy for superficial bladder cancer. A developmental and clinical overview. Urol Clin North Am 1992; 19:549-556.

Mukhtar et al., "Tumor-associated macrophages in breast cancer as potential biomarkers for new treatments and diagnostics", Expert Rev. Mol. Diagn. (2011) vol. 11, No. 1, pp. 91-100.

Munoz et al., "The role of defective clearance of apoptotic cells in systemic autoimmunity", Nat. Rev. Rheumatol. (2010) vol. 6, pp. 280-289.

Kempin et al., Combined modality therapy of advanced nodular lymphomas: the role of nonspecific immunotherapy (MBV) as an important determinant of response and survival, Proc Am Soc Clin Oncol 24:56 (1983).

Nagata, "Rheumatoid polyarthritis caused by a defect in DNA degradation", Cytokine & Growth Factor Reviews (2008) vol. 19, pp. 295-302.

Nardone et al. Helicobacter pylori and gastric malignancies. Helicobacter 2003;1(8 Suppl):44-52.

Nauts et al., "A review of the influence of bacterial infection and of bacterial products (Coley's toxins) on malignant tumors in man" Acta Med. Scand., (1953), 145 (Suppl. 276), 5-103.

Negus et al. Quantitative assessment of the leukocyte infiltrate in ovarian cancer and its relationship to the expression of C-C chemokines. Am J Pathol 1997;150:1723.

Niwa et al. Correlation of tissue and plasma RANTES levels with disease course in patients with breast or cervical cancer. Clin Cancer Res 2001;7:285.

O'Brien et al., "SRL172 (killed *Mycobacterium vaccae*) in addition of standard chemotherapy improves quality of life without affecting survival, in patients with advanced non-small-cell lung cancer: phase III results", Annals of Oncology (2004) 15: 906-914.

O'Byrne et al. Chronic immune activation and inflammation as the cause of malignancy. Br J Cancer 2001 ;85:473.

Ochiai et al. Postoperative adjuvant immunotherapy of gastric cancer with BCG-cell wall endoskeleton. Three- to six-year follow-up of a randomized clinical trial, Cancer Immunol Immunother 14:167-171 {1983).

Ogura. Immunotherapy of respectable lung cancer using Nocardia rubra cell wall skeleton, Gan To Kagaku Ryoho 10{2 Pt 2)366-372 (1983).

Ohno et al. Randomized controlled study of chemoimmunotherapy of acute myelogenous leukemia (AML) in adults with Nocardia rubra cell-wall skeleton and irradiated allogeneic AML cells, Cancer 57(8):1483-1488 (Apr. 1986).

Ohshima. Genetic and epigenetic damage induced by reactive nitrogen species: Implications in carcinogenesis. Toxicol Lett 2003;140-141:99-104.

Okamoto et al. Toll-like receptor signaling in anti-cancer immunity.J Med Invest 2003;50:9-24.

Okawa et al. Phase II randomized clinical trial of LC9018 concurrently used with radiation in the treatment of carcinoma of the uterine cervix. Its effect on tumor reduction and histology. Cancer Nov. 1, 1989;64[9]:1769-76.

Omata et al. Prevention and treatment of hepatocellular carcinoma. Liver Transpl 2004; 10:S111-4.

Pace et al., "Inactivated whole-cell bacterial vaccines: current status and novel strategies", Vaccine, vol. 16, No. 16, pp. 1563-1574 (1998).

Pack. Note on the experimental use of rabies vaccine for melanomatosis, Arch Dermatol 62:694-695 (1950).

Pajonk et al. The effects of tea extracts on proinflammatory signaling. BMC Med Dec. 1, 2006:(4)28.

Palmieri et al. Serum 25-hydroxyvitmain D levels in early and advanced breast cancer. J Clin Pathol 2006;0:1-3.

Papachristou et al. Effect of postoperative wound infection of the course of stage II melanoma. Cancer 1979;43:1106-1111.

Paterson et al. Listeria-based vaccines for cancer treatment. Curr. Opin. Mol. Ther 7(5):454-460 (Oct. 2005).

Pavia et al. Association between fruit and vegetable consumption and oral cancer: a meta-analysis of observational studies. Am J Clint Nutr May 2006:83(5)1126-34.

Pawelec. Tumour escape from the immune response. Cancer Immunol Immunother 2004:53:843.

Pawelec. Tumour escape: antitumour effectors too much of a good thing? Cancer Immunol Immunother 2004:53:262.

Pelner. Effects of concurrent infections and their toxins on the course of leukemia. Acta Medica Scand. 1958; 162: 4-47 Cancer Research Institute, Inc, New York. Monograph #2.

Pfahlberg et al., "Inverse Association Between Melanoma and Previous Vaccinations Against Tuberculosis and Smallpox: Results of the FEBIM Study" The Society for Investigative Dermatology, Inc. (2002) 119 (3): 570-575.

Pischon et al. Habitual dietary intake of n-3 and n-6 fatty acids in relation to inflammatory markers among US men and women. Circulation 2003;108:155-60.

Platsoucas et al. Immune responses to human tumors: development of tumor vaccines. Anticancer Res 2003;23:1969.

Pollard. Tumour-educated macrophages promote tumour progression and metastasis. Nat. Rev. Cancer (2004) 4,71-8.

Prasad et al. (1999) High doses of multiple antioxidant vitamins: essential ingredients in improving the efficacy of standard cancer therapy. J Am Coll Nutr. 18:13-25.

Pukkala et al. Time trends in socio-economic differences in incidence rates of cancers of the breast and female genital organs (Finland, 1971-1995). Int J Cancer 1999;81:56-61.

Pulaski et al., "Cooperativity of *Staphylococcal aureus* Enterotoxin B Superantigen, Major Histocompatibility Complex Class II, and

(56) References Cited

OTHER PUBLICATIONS

CD80 for Immunotherapy of Advanced Spontaneous Metastases in a Clinically Relevant Postoperative Mouse Breast Cancer Model" Cancer Research (2000) vol. 60, pp. 2710-2715.
Radford et al., "A recombinant *E. coli* vaccine to promote MHC class I-dependent antigen presentation: application to cancer immunotherapy", Gene Therapy, vol. 9, No. 21, pp. 1455-1463 (2002).
Rakel et al. Inflammation: Nutritional, Botanical, and Mind-Body Influences. Southern Medical Journal 98(3);302-10 Mar. 2005.
Ravindranath et al. Epicatechins purified from green tea (Camellia sinensis) differentially suppress growth of gender-dependent human cancer cell lines. Evid Based Complement Alternat Med Jun. 2006:3(2)237-247.
Reddy et al. Mechanisms of curcurmin- and EGF-receptor related protein (ERRP)-dependent growth inhibition of colon cancer cells. Nutr Cancer 2006:55(2)185-194.
Riboli et al. Epidemiologic evidence of the protective effect of fruit and vegetables on cancer risk. Am J Clint Nutr Sep. 2003;78(3 Suppl):5595-5695.
Rolny et al., "HRG Inhibits Tumor Growth and Metastasis by Inducing Macrophage Polarization and Vessel Normalization through Downregulation of PIGF", Cancer Cell (2011) vol. 19, pp. 31-44.
Ruckdeschel et al Postoperative empyema improves survival in lung cancer. New England Journal of Medicine. 1972; 287(20): 1013-1017.
Saemann et al. Anti-inflammatory effects of sodium butyrate on human monocytes: potent inhibition of IL-12 and up-regulation of IL-10 production. FASEB Journal Dec. 2000(14)2380-2.
Saji et al. Significant correlation of monocyte chemoattractant protein-1 expression with neovascularization and progression of breast carcinoma. Cancer 2001;92:1085.
Salvesen et al. Significance of tumor-associated macrophages, vascular endothelial growth factor and thrombospondin-1 expression for tumor angiogenesis and prognosis in endometrial carcinomas. Int J Cancer. 1999; 84:538-43.
Sandhu et al. Neutrophils, nitric oxide synthase, and mutations in the mutatect murine tumor model. Am J Pathol 2000;156:509-18.
Sapi. The role of CSF-1 in normal physiology of mammary gland and breast cancer: an update. Exp Biol Med (Maywood) 2004;229:1.
Schleithoff et al. Vitamin D supplementation improves cytokine profiles in patients with congestive heart failure: a double-blind, randomized, placebo-controlled trial. Am J Clin Nutr. Apr. 2006;83(4);754-9.
Schmid et al., "Myeloid Cells in the Tumor Microenvironment: Modulation of Tumor Angiogenesis and Tumor Inflammation", Journal of Oncology (2010) pp. 1-10.
Schwartsburd. Chronic inflammation as inductor of pro-cancer microenvironment: pathogenesis of dysregulated feedback control. Cancer Metastasis Rev 2003;22:95.
Schwartz et al. Vitamin D status and cancer: new insights. Curr Opin Clin Nutr Metab Care 2007:10(1)6-11.
Seely et al. The effects of green tea consumption on incidence of breast cancer and recurrence of breast cancer: a systemic review and meta-analysis. Integ Cancer Ther 2005:4(2)144-155.
Shepherd. Alternatives to chemotherapy and radiotherapy as adjuvant treatment for lung cancer. Lung Cancer 1997; 17 (suppl):S121-S136.
Sica et al. Tumour-associated macrophages: a molecular perspective. Int Immunopharmacol 2002;2:1045.
Siegel et al. Cytostatic and apoptotic actions of TGFβin homeostasis and cancer. Nat Rev Cancer 2003:3:807.
Smith et al. Randomized trial of adjuvant therapy in colon carcinoma: 10-Year results of NSABP protocol C-01, J. NCI96(15)1128-1132 (2004).
Smith et al. Recorded and expected mortality among Navajo, with special reference to cancer. J Natl Cancer Inst 1956;17:77-89.
Smith. Recorded and expected mortality among Indians in the United States with special reference to cancer. J Natl Cancer Inst 1957;18:385-96.
Smolen et al. 2010 (Treating rheumatoid arthritis to target: recommendations of an international task force; Ann Rheum Dis; 69:631-637).
Solinas et al., "Tumor-associated macrophages (TAM) as major players of the cancer-related inflammation", Journal of Leukocyte Biology (2009) vol. 86, pp. 1065-1073.
Standiford et al., "TGF-β-Induced IRAK-M expression in tumor-associated macrophages regulates lung tumor growth", Oncogene (2011) vol. 30, No. 21, pp. 1-10.
Stephenson et al. Host immunity and spontaneous regression of cancer evaluated by computerized data reduction study. Surg Gynecol Obstet. Oct. 1971;133(4):649-55.
Sumida et al., "Rheumatoid Arthritis and Apoptosis", Internal Medicine (1998) vol. 37, No. 2, pp. 184-188.
Sunderkotter et al. Macrophages and angiogenesis. J Leukoc Biol 1994(55)410-422.
Sur et al. Role of Mycobacterium was adjuvant treatment of lung cancer (non-small cell lung cancer), J. Indian Med Assoc 101 (2):118-120 (Feb. 2003).
Sylvester et al. Intravesical Bacillus Calmette-Guerin Reduces the Risk of Progression in Patients With Superficial Bladder Cancer: A Meta-Analysis of the Published Results of Randomized Clinical Trials, The Journal of Urology 168:1967-1970 (Nov. 2002).
Takahashi et al. Platelet-derived growth factor in human colon cancer angiogenesis: role of infiltrating cells. J Natl Cancer Inst 1996; 88: 1146±1151.
Takanami et al. Tumor-associated macrophage infiltration in pulmonary adenocarcinoma: association with angiogenesis and poor prognosis. Oncology 1999; 57: 138±142.
Takita. Effect of postoperative empyema on survival of patients with bronchogenic carcinoma. J Thorac Cardiovasc Surg. 1970; 59:642-44.
Tanaka et al. (1979) Vitamin E and immune response. Immunology 38:727.
Thangapazham et al. Multiple molecular targets in cancer chemoprevention by curcumin. AAPS J Jul. 7, 2006:8(3)E443-9.
Thompson et al. Dietary flaxseed alters tumor biological markers in postmenopausal breast cancer. Clin Cancer Res May 15, 2005:11(10)3828-3835.
Thun et al. Inflammation and cancer: an epidemiological perspective. Novartis Found Symp 2004;256:6.
Tilley et al. Mixed messages: modulation of inflammation and immune responses by prostaglandins and thromboxanes. J Clin Invest 2001;108:15.
Trampuz et al. 2005 (Prosthetic joint infections: update in diagnosis and treatment; Swiss Med Wkly; 135:243-251).
Ueno et al. Significance of macrophage chemoattractant protein-1 in macrophage recruitment, angiogenesis, and survival in human breast cancer. Clin Cancer Res 2000;6:3282.
Uyl-De Groot et al. Immunotherapy with autologous tumor ceii-BCG vaccine in patients with colon cancer: a prospective study of medical and economic benefits, Vaccine 23(17-18):2379-2387 (2005).
Van Netten et al. Macrophage tumor cell associations: a factor in metastasis of breast cancer? J Leukoc Biol 1993; 54: 360±362.
Van Netten et al. Macrophage-tumour cell associations in breast cancer. Lancet 1993;342:872-3.
Van Netten et al. Macrophages and their putative significance in human breast cancer. Br J Cancer. 1992; 66:220-1.
Velicer et al. Antibiotic use in relation to the risk of breast cancer. JAMA. 2004; 18;291(7):880-1.
Verdrengh et al. 2007 (Addition of bisphosphonate to antibiotic and anti-inflammatory treatment reduces bone resorption in experimental *Staphylococcus aureus*-induced Arthritis; Journal of Orthopaedic Research, 2007, pp. 304-31 0).
Viallard et al. Disseminated infection after bacilli Camille-Guerin instillation for treatment of bladder cancer. Clin Infect Dis 1999; 29:451-2.
Walker. "Considerations for development of whole cell bacterial vaccines to prevent diarrheal diseases in children in developing countries", Vaccine, vol. 23, pp. 3369-3385 (2005).
Wallace. Nutritional and botanical modulation of the inflammatory cascade—eicosanoids, cyclooxygenases, and lipoxygenases—as an adjunct in cancer therapy. Integr Cancer Ther. Mar. 2002;1(1):7-37.

(56) References Cited

OTHER PUBLICATIONS

Wang et al. Tumor cells caught in the act of invading: their strategy for enhanced cell motility. Trends Cell Biol 15(2005)138-145.
Warburton et al. Health benefits of physical activity: the evidence. CMAJ Mar. 14, 2006;174(6):801-9.
Watanabe et al. Urinary interleukin-2 may predict clinical outcome of intravesical bacillus Calmette-Guerin immunotherapy for carcinoma in-situ of the bladder. Cancer Immunol Immunother 2003;52:481-6.
Witzman et al. Phagocytes as carcinogens: malignant transformation produced by human neutrophils. Science 1985;227:1231-3.
Williams et al. The role of cyclooxygenases in inflammation, cancer and development. Oncogene 1999;18:7908.
Wojtowicz-Praga. Reversal of tumor-induced immunosuppression by TGFβinhibitors. Invest New Drugs 2003;21:21.
Woo et al. Cutting edge: regulatory T cells from lung cancer patients directly inhibit autologous T cell proliferation. J Immunol 2002;168:4272-4276.
Wyckoff et al. A paracrine loop between tumor cells and macrophages is required for tumor cell migration in mammary tumors. Cancer Res 64(2004)7022-7029.
Yasumoto et al. Randomized clinical trial of non-specific immunotherapy with cell-wall skeleton of Nocardia rubra, Biomed Pharmacother 38(1 ):48-54 (1984).
Yu et al. Host microenvironment in breast cancer development: inflammatory and immune cells in tumour angiogenesis and arteriogenesis. Breast Cancer Res 2003;5:83.
Yue et al. Interleukin 10 is a growth factor for human melanoma cells and down-regulates HLA class-I, HLA class-II and ICAM-1 molecules. Int J Cancer 1997;71:630.
Zhou et al. (1998) Mechanism for the suppression of the mammalian stress response by genisten, an anticancer phytoestrogen from soy. J Natl Cancer Inst. 90:381-8.
Boudeau et al. "Invasive Ability of an *Escherichia coli* Strain Isolated from the Ileal Mucosa of a Patient with Crohn's Disease" Infection and Immunity, 1999, vol. 67(9):4499-4509.
Caugant et al., "Genetic Diversity and Temporal Variation in the *E. coli* Population of a Human Host" Genetics, 1981, vol. 98:467-496.
Connor, "Sequelae of Travelers Diarrhea: Focus on Postinfectious Irritable Bowel Syndrome" CID, 2005, vol. 2005:41, supplement 8: S557-S586.
Kruis et al., "Double-blind comparison of an oral *Escherichia coli* preparation and mesalazine in maintaining remission of ulcerative colitis", Alimentary Pharmacology and Therapeutics, vol. 11, No. 5, pp. 853-858 (1997).
Lee et al. Evaluation of the acute and subchronic toxic effects in mice, rats, and monkeys of the genetically engineered and *Escherichia coli* cytosine deaminase gene-incorporated Salmonella strain, TAPET-CD, being developed as an antitumor agent, Int J Toxicol (2001), 20(4):207-217.
Martin et al., Enhanced *Escherichia coli* adherence and invasion in Crohn's disease and colon cancer, Gastroenterology (2004), 127(1):80-93.
Martinez-Medina et al. "Molecular diversity of *Escherichia coli* in the Human Gut: New Ecological Evidence Supporting the Role of Adherent-Invasive *E. coli* (AIEC) in Crohn's Disease" Inflamm Bowel Dis., 2009,vol. 15(6):872-882.
Savarino et al., "Safety and Immonogenicity of an Oral, Killed Enterotoxigenic *Escheria coli* —Cholera Toxing B Subunit B Vaccine in Egyptian Adults" The Journal of Infectious Diseases, 1998, vol. 177:796-799.
Torres et al., "Evaluation of Formalin-Inactivated Clostridium difficile Vaccines Administered by Parenteral and Mucosal Routes of Immunization in Hamsters", Infection and Immunity, vol. 63, No. 12, pp. 4619-4627 (1995).
Wolmark et al. Postoperative adjuvant chemotherapy or BCG for colon cancer: results from NSABP protocol C-01, J Natl Cancer Inst (1988), 80(1):30-36.
Kovats et al. Vaccina treatment in some hospital infections, Acta Physiol Hung (1991), 77(3-4):225-230.
Critchley et al. Genetically engineered *E. coli* as a protein delivery vehicle for killing cancer cells, Discov Med (2004), 4(22):194-197.
Jibu et al. Active components of intestinal bacteria for abdominal irradiation-induced inhibition of lung metastases, Clinical & Experimental Metastasis (1991), 9(6):529-540.
Sarmiento et al. Staging strategies for pancreatic adenocarcinoma: what the surgeon really wants to know, Curr Gastroenterol Rep (2003), 5(2):117-124.
Fujihara et al. Intratumoral injection of inactivated Sendai virus particles elicits strong antitumor activity by enhancing local CXCL10 expression and systemic NK cell activation, Cancer Immunol Immunother (2008), 57(1):73-84.
Kurooka et al. Inactivated Sendai virus particles eradicate tumors by inducing immune responses through blocking regulatory T cells, Cancer Res (2007), 67(1):227-236.
Smith et al. Disordered macrophage cytokine secretion underlies impaired acute inflammation and bacterial clearance in Crohn's disease, J Exp Med (2009), 206(9):1883-1897.
Guideline for the Care and Use of Mammals in Neuroscience and Behavioral Research, Published by National Research Council in 2003, pp. 111-113.
Cross et al. Active Immunization with a Detoxified *Escherichia coli* J5 Lipopolysaccharide Group B Meningococcal Outer Membrane Protein Complex Vaccine Protects Animals from Experimental Sepsis, J Infect Dis. (2001) 183 (7): 1079-1086.
Brockstedt et al. Listeria-based cancer vaccines that segregate immunogenicity from toxicity, PNAS (2004), 101(38):13832-13837.
Bischoff et al. An adenovirus mutant that replicates selectively in p53-deficient human tumor cells, Science. Oct. 18, 1996;274(5286):373-6.
Sznol et al. Use of preferentially replicating bacteria for the treatment of cancer, J Clin Invest. Apr. 15, 2000; 105(8): 1027-1030.
Moens et al., Cross-Protective Immunity against Heterologous *Streptococcus pneumoniae*, Infect Immun. May 2012; 80(5): 1944-1945.
Tang et al. Preliminary result of mixed bacterial vaccine as adjuvant treatment of hepatocellular carcinoma, Med Oncol Tumor Pharmacother. 1991;8(1):23-8.
Varghese et al. Oncolytic herpes simplex virus vectors for cancer virotherapy, Cancer Gene Ther. Dec. 2002;9(12):967-78.
Mackie et al. Intralesional injection of herpes simplex virus 1716 in metastatic melanoma, Lancet. Feb. 17, 2001;357(9255):525-6.
Markert et al. Conditionally replicating herpes simplex virus mutant, G207 for the treatment of malignant glioma: results of a phase I trial, Gene Ther. May 2000;7(10):867-74.
Fukiya et al. Extensive genomic diversity in pathogenic *Escherichia coli* and Shigella Strains revealed by comparative genomic hybridization microarray, J Bacteriol. Jun. 2004;186(12):3911-21.
McLellan et al. Genetic characterization of *Escherichia coli* populations from host sources of fecal pollution by using DNA fingerprinting, Appl Environ Microbiol. May 2003;69(5):2587-94.
Kochetkova et al. Vaccination without Autoantigen Protects against Collagen II-Induced Arthritis via Immune Deviation and Regulatory T Cells, J Immunol 2008; 181:2741-2752.
Dlugovitzky et al. Effect of *Staphylococcus aureus* on the development of a sarcoma in rats, Rev. Microbiol., Sao Paulo, 1990, 23(2):66-71.
Iannello et al. Effect of oral administration of different combinations of killed bacteria on some depressed macrophage functions in tumor-bearing rats, Immunopharmacology, 1985, 9(3):181-187.
Marchand et al. Tumor regressions observed in patients with metastatic melanoma treated with an antigenic peptide encoded by gene MAGE-3 and presented by HLA-A1, Int J Cancer. Jan, 18, 1999;80(2):219-30.
Mathews. Antitumor effects of a variety of non-viable bacteria against the murine EL-4 lymphoma, Cancer Immunology, Immunotherapy Dec. 1981, 12(1):81-85.
McLean. Cutaneous Manifestations of Internal Malignant Disease, Can Fam Physician. Oct. 1987; 33: 2357-2365.
Choi et al. CD206-positive M2 macrophages that express heme oxygenase-1 protect against diabetic gastroparesis in mice, Gastroenterology, Jun, 2010;138(7):2399-409.

(56) References Cited

OTHER PUBLICATIONS

Jernigan et al. Parasitic infections of the small intestine, Gut, Mar. 1994; 35(3): 289-293.

Laskin et al. Macrophages and tissue injury: agents of defense or destruction?, Annu Rev Pharmacol Toxicol. 2011;51:267-88.

Schafer et al. Parasites of the small intestine, Curr Gastroenterol Rep. Aug. 2006;8(4):312-20.

Wang et al., Pulmonary and Systemic Host Response to *Streptococcus pneumoniae* and *Klebsiella pneumoniae* Bacteremia in Normal and Immunosuppressed Mice, Infect Immun. Sep. 2001; 69(9): 5294-5304.

Behrouz et al., Immunization with Bivalent Flagellin Protects Mice against Fatal *Pseudomonas aeruginosa* Pneumonia, Journal of Immunology Research vol. 2017, Article ID 5689709, 17 pages.

Cripps et al., Mucosal and systemic immunizations with killed *Pseudomonas aeruginosa* protect against acute respiratory infection in rats, Infect Immun. Apr. 1994;62(4):1427-36.

Gilleland et al., Outer membrane protein F preparation of *Pseudomonas aeruginosa* as a vaccine against chronic pulmonary infection with heterologous immunotype strains in a rat model, Infect Immun. May 1988;56(5):1017-22.

Li et al., X-ray Irradiated Vaccine Confers protection against Pneumonia caused by *Pseudomonas aeruginosa*, Scientific Reports vol. 6, Article No. 18823 (2016).

Priebe et al., Protection against Fatal *Pseudomonas aeruginosa* Pneumonia in Mice after Nasal Immunization with a Live, Attenuated aroA Deletion Mutant, Infect Immun. Mar. 2003; 71(3): 1453-1461.

Staczek et al., Immunization with a chimeric tobacco mosaic virus containing an epitope of outer membrane protein F of *Pseudomonas aeruginosa* provides protection against challenge with *P. aeruginosa*, Vaccine. Apr. 28, 2000;18(21):2266-74.

Kassabov et al., "Inhibitory Effect of the Oral Vaccine Respivax on Pulmonary Metastases of Lewis Lung Carcinoma in Mice," Medecine Oncologie, pp. 117-119, Jun. 27, 1990.

Kisjova et al., "The Immunomodulants for Lung Cancer Under Experimental and Clinical Conditions," Probl. Inf. Parasit. Dis., 1999, pp. 25-28 ,vol. 27.

Mathur et al., "Immunomodulation of Intradermal Mammary Carcinoma using Staphage Lysate in a rat model," Journal Article, 1988, pp. 117-123, vol. 1(2).

Wang et al., "Characterization of TLR2, NOD2, and Related Cytokines in Mammary Glands Infected by *Staphylococcus aureus* in a Rat Model," Acta Veterinaria Scandinavica, 2015, pp. 1-6, 57:25.

Mueller et al., Hyposensitization with Bacterial Vaccine in Infectious Asthma: A Double-Blind Study and a Longitudinal Study, JAMA, May 26, 1969, vol. 208, No. 8, p. 1379-1383.

Jesenak et al., Recurrent Respiratory Infections in Children—Definition, Diagnostic Approach, Treatment and Prevention, Bronchitis, 2011, Retrieved from www.intechopen.com, p. 119-148.

* cited by examiner

ANTI-MICROBIAL IMMUNOMODULATION

CROSS-REFERENCE TO RELATED APPLICATIONS

This application is a continuation of U.S. patent application Ser. No. 15/308,302 filed Nov. 1, 2016, which application is a U.S. National Phase Application of PCT Application No. PCT/CA2015/050377 filed May 1, 2015, which application claims priority to U.S. Provisional Patent Application Ser. No. 61/988,117 filed May 2, 2014, the disclosure of which are herein incorporated by reference.

FIELD OF THE INVENTION

In various aspects, the invention relates to immunological therapies for treating or preventing pathologies associated with microbial infections in a vertebrate, including the use of microbial vaccines.

BACKGROUND OF THE INVENTION

The innate immune system and the adaptive immune system work in concert in vertebrates to provide, among many other things, protection from pathogenic infection by micro-organisms. Anti-microbial vaccines may be formulated to engage both the innate and adaptive immune systems, but an effective response to vaccination is generally understood to involve a specific adaptive response to one or more of the immunogens present in a vaccine. In this way, multivalent vaccines, such as some pneumococcal vaccines, may be used to elicit a specific adaptive response to more than one serovar. Vaccines have also been described that confer some degree of cross-protective immunity, in which cross-reactivity to an antigen other than the immunogen confers a degree of protective immunity to heterologous microorganisms.

SUMMARY OF THE INVENTION

In one aspect, the invention provides methods and compositions for treating a vertebrate subject for a condition characterized by pathologies associated with a microbial infection, involving the use of microbial vaccines derived from one pathogenic organism to treat infections caused by a heterologous pathogenic organism.

BRIEF DESCRIPTION OF THE DRAWINGS

FIG. 7A is a survival curve 5 days post-challenge. FIGS. 7B-7E illustrate *S. pneumoniae* quantified in nasal wash, lung and spleen homogenate. Megakaryocytes were counted in ten adjacent high power fields (400× magnification) of histological spleen sections. Statistical significance was determined by two-tailed Mann-Whitney test.

DETAILED DESCRIPTION OF THE INVENTION

Figure 1A:
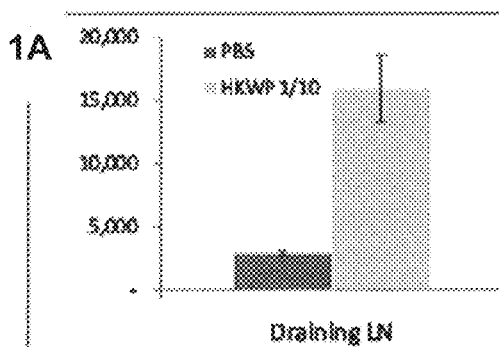
FIGS. 1A, 1B and 1C show the number of inflammatory monocytes and dendritic cells in the draining lymph node, lungs, and spleen of mice following treatment with either a *K. pneumoniae* antigenic composition or PBS, as described in Example 1A herein.

In various aspects, the invention relates to the surprising discovery that administration of formulations that include antigenic determinants of microbial pathogens that are pathogenic in a particular tissue or organ, is effective in treating pathologies associated with heterologous microbial infections in that specific tissue or organ. Compositions of the invention may for example be administered at a site that is distant from the site of infection. Accordingly, the invention provides antigenic compositions derived from these microbial pathogens, including whole killed bacterial, viral or fungal species, or components thereof, for the therapeutic or prophylactic treatment of heterologous microbial infections, and methods for using the same. The compositions may for example be derived from endogenous pathogens or exogenous pathogens, as described in more detail below.

Antigenic compositions of the invention may be produced that include antigenic determinants that together are specific for or characteristic of a microbial pathogen. In this context, by "specific", it is meant that the antigenic determinants are sufficiently characteristic of the pathogen that they could be used to raise an immune response, such as an adaptive immune response, against the pathogen in the patient, if the antigenic determinants were to be administered in an appropriate manner to have that effect. It will be recognized that the antigenic determinants need not be so specific that they are characteristic of only one particular strain or species of pathogen, since even a specific immune response against a particular pathogen may be cross reactive with other closely related organisms that are also naturally pathogenic in the tissue or organ in which the heterologous infection is situated and that the antigenic composition is formulated or selected to target.

A "cell" is the basic structural and functional unit of a living organism. In higher organisms, e.g., animals, cells having similar structure and function generally aggregate into "tissues" that perform particular functions. Thus, a tissue includes a collection of similar cells and surrounding intercellular substances, e.g., epithelial tissue, connective tissue, muscle, nerve. An "organ" is a fully differentiated structural and functional unit in a higher organism that may be composed of different types of tissues and is specialized for some particular function, e.g., kidney, heart, brain, liver, etc. Accordingly, by "specific organ, tissue, or cell" is meant herein to include any particular organ, and to include the cells and tissues found in that organ.

"Pathogenic" agents are agents, such as microbes, such as bacteria or viruses, which are known to cause infection in a host in nature, and in this sense, "pathogenic" is used in the context of the present invention to mean "naturally pathogenic". Although a wide variety of microbes may be capable of causing infection under artificial conditions, such as artificial inoculations of a microbe into a tissue, the range of microbes that naturally cause infection is necessarily limited, and well established by medical practice.

An "infection" is the state or condition in which the body or a part of it is invaded by a pathogenic agent (e.g., a microbe, such as a bacterium) which, under favorable conditions, multiplies and produces effects that are injurious (Taber's Cyclopedic Medical Dictionary, 14th Ed., C. L. Thomas, Ed., F. A. Davis Company, PA, USA). An infection may not always be apparent clinically and may result in only localized cellular injury. Infections may remain subclinical, and temporary if the body's defensive mechanisms are effective. Infections may spread locally to become clinically apparent as an acute, a subacute, or a chronic clinical infection or disease state. A local infection may also become systemic when the pathogenic agent gains access to the lymphatic or vascular system. Infection is usually accompanied by inflammation, but inflammation may occur without infection.

"Inflammation" is the characteristic tissue reaction to injury (marked by swelling, redness, heat, and pain), and includes the successive changes that occur in living tissue when it is injured. Infection and inflammation are different conditions, although one may arise from the other (Taber's Cyclopedic Medical Dictionary, supra). Accordingly, inflammation may occur without infection and infection may occur without inflammation (although inflammation typically results from infection by pathogenic bacteria or viruses). Inflammation is characterized by the following symptoms: redness (rubor), heat (calor), swelling (infection), pain (dolor). Localized visible inflammation on the skin may be apparent from a combination of these symptoms, particularly redness at a site of administration.

Various subjects may be treated in accordance with alternative aspects of the invention. As used herein, a "subject" is an animal, for e.g, a vertebrate such as a mammal, to whom the specific pathogenic bacteria, bacterial antigens, viruses, viral antigens or compositions thereof of the invention may be administered. Accordingly, a subject may be a patient, e.g., a human, suffering from microbial infection, or suspected of having a microbial infection, or at risk for developing a microbial infection. A subject may also be an experimental animal, e.g., an animal model of infection. In some embodiments, the terms "subject" and "patient" may be used interchangeably, and may include a human, a non-human mammal, a non-human primate, a rat, mouse, dog, etc. A healthy subject may be a human who is not suffering from an infection or suspected of having an infection, or who is not suffering from a chronic disorder or condition. A "healthy subject" may also be a subject who is not immunocompromised. By "immunocompromised" or "immunosuppressed" is meant any condition in which the immune system functions in an abnormal or incomplete manner, for example wherein the host is a patient who does not have the ability to respond normally to an infection due to an impaired or weakened immune system. Immunocompromisation or immunosuppression may be due to disease, certain medications (such as chemotherapeutics used in cancer treatment), or conditions present at birth. Immunocompromised subjects may be found more frequently among infants, the elderly, and individuals undergoing extensive drug or radiation therapy. Accordingly, aspects of the invention involve the treatment of pediatric and geriatric patients, or patients at risk of a nosocomial infection. Particular patient populations may for example include patients with compromised immune systems due to HIV infection or AIDS, cancer, solid organ transplantation, stem cell transplantation, sickle cell disease or asplenia, congenital immune deficiencies, chronic inflammatory conditions, cochlear implants, or cerebrospinal fluid leaks.

An "immune response" includes, but is not limited to, one or more of the following responses in a mammal: induction or activation of antibodies, neutrophils, monocytes, macrophages (including both M1-like macrophages and M2-like macrophages as described herein), B cells, T cells (including helper T cells, natural killer cells, cytotoxic T cells, γδ T cells), such as induction or activation by the antigen(s) in an antigenic composition, following administration of the composition. An immune response to a composition thus generally includes the development in the host animal of a cellular and/or antibody-mediated response to the composition of interest. In some embodiments, the immune response is such that it will also result in slowing or stopping the progression of an infection in the animal. An immune response includes both cellular immune responses and humoral immune responses, of both the innate and adaptive immune systems.

In selected embodiments, the methods of the invention may involve determining whether the individual has previously been infected with a pathogen that is pathogenic in the specific organ or tissue; and administering to the individual a therapeutic composition comprising antigenic determinants that are selected or formulated so that together they are specific for the at least one pathogen.

In another aspect, the invention provides methods of formulating compositions of the invention for treating an individual for a condition characterized by microbial disease or infection in a specific organ or tissue. The methods may involve determining whether the individual has previously been infected with at least one pathogen that is pathogenic in the specific organ or tissue; producing an antigenic composition comprising antigenic determinants that together are specific for the at least one pathogen; and formulating the antigenic composition for administration as a therapeutic or anti-microbial composition capable of eliciting an immunological or anti-microbial response in the specific organ or tissue to a heterologous micro-organism.

The methods detailed herein to determining whether a subject has previously been exposed to a pathogen may involve identifying the presence of at least one antibody that recognizes the pathogen. The methods may also or alternatively involve identifying at least one memory B cell that recognizes the pathogen. The methods may also or alternatively involve identifying at least one memory T cell that recognizes the pathogen. The methods may for example involve obtaining the antibody, the memory B cell, or the memory T cell from peripheral circulation or from the targeted specific organ or tissue of the individual.

In another aspect, the invention provides methods of prophylactically treating an individual for an infection in a specific organ or tissue, involving the administration of an infectious micro-organism to provoke a potentiating infection in that organ or tissue. The method may for example involve administering to the individual an infectious dose of at least one pathogen that is pathogenic in the specific organ or tissue, such as an attenuated pathogen; and administering to the individual an anti-microbial composition comprising antigenic determinants, the antigenic determinants selected or formulated so that together they are specific for the at least one pathogen, such as a composition comprising killed whole pathogens, so as to treat or prevent an infection by a heterologous micro-organism. The method may involve these two administration steps occurring simultaneously. The method may involve the second step occurring between 1 hour and 30 days after the first step.

Compositions of the invention may for example be formulated or used for administration at a site that is distinct from the specific organ or tissue that is targeted for treatment, for example by subcutaneous injection or intradermal injection. Compositions may for example be formulated for repeated administration, for example by subcutaneous or intradermal injection. In selected embodiments, compositions of the invention may be formulated or used so as to produce a localized immune response at a site of administration, for example at a site of injection in the skin.

In selected embodiments, pathogens may be selected for use in methods and compositions of the invention on the basis that the pathogen is endogenous to the specific organ or tissue that is targeted for treatment. Alternatively, the pathogen may be exogenous to the specific organ or tissue. The pathogen may be formulated as an attenuated or a killed pathogen, for example to provide an antigenic composition of whole attenuated or killed pathogens. For example, the pathogen may be a bacterium, a virus, a protozoa, a fungus, or a helminth.

In a further aspect, a method of formulating an anti-microbial composition for treating a condition characterized by an infection in a specific organ or tissue is provided. The method involves selecting at least one pathogen that is pathogenic in the specific organ or tissue; producing an antigenic composition comprising antigenic determinants that together are specific for the pathogen; and formulating the antigenic composition for administration as an anti-microbial composition capable of eliciting an anti-microbial response in the specific organ or tissue to a heterologous micro-organism.

The method may further involve a diagnostic step of identifying the specific organ or tissue within which the infection is symptomatic prior to producing the antigenic composition.

Optionally, the antigenic composition may be formulated for subcutaneous injection or intradermal injection. Optionally, the antigenic composition may be formulated for injection to produce a localized skin immune response at a site of administration. Optionally, the method detailed herein is provided such that when a specific tissue or organ is determined, the pathogen is selected from a particular group of pathogens as described herein. In one aspect the pathogen is one that is an endogenous organism, which is a natural cause of infection in the tissue or organ in question. Optionally, the pathogen is an exogenous organism that is a natural cause of infection in the tissue or organ is question, and may include, for example, a bacteria, virus, helminth, or fungus.

Optionally, the antigenic composition may be formulated for repeated subcutaneous or intradermal administration. Optionally, the antigenic composition may be formulated for administration by a route that is not enteric. Optionally, the pathogen detailed herein is a bacteria, a virus, a protozoa, a fungus or a helminth. Further, the method may involve killing or attenuating the pathogen to formulate the antigenic composition as a whole killed or attenuated pathogen composition. The pathogen may be a member of a species of the endogenous flora that is a natural cause of infection in the specific organ or tissue. The pathogen may be an exogenous species that is a natural cause of infection in the specific organ or tissue.

In another aspect, a method of treating an individual for a condition characterized by infection, or a pathology associated with a microbial infection, in a specific organ or tissue is provided. The method involves administering to the individual an anti-microbial composition comprising antigenic determinants. The antigenic determinants are selected or formulated so that together they are specific for at least one pathogen that is pathogenic in the specific organ or tissue. Optionally, the anti-microbial composition may be administered at an administration site in successive doses given at a dosage interval of between one hour and one month, over a dosage duration of at least two weeks. Further, and without limitation, the dosing may comprise two or more doses (or 10 or more, or 100 or more) over a period from, for example, 1, 2, 3, 4, 5 or 6 days to 1, 2, 3, 4, 5, or 6 weeks.

In another aspect, use of an anti-microbial composition for treating an individual for a condition characterized by inflammation in a specific organ or tissue is disclosed. The anti-microbial composition may for example contain antigenic determinants selected or formulated so that together they are specific for at least one microbial pathogen that is pathogenic in the specific organ or tissue.

In another aspect, use of an anti-microbial composition to formulate a medicament for treating an individual for a condition characterized by pathologies associated with an infection in a specific organ or tissue is disclosed. The anti-microbial composition may for example contain antigenic determinants selected or formulated so that together they are specific for at least one microbial pathogen that is pathogenic in the specific organ or tissue.

In one aspect, a method of comparing immune responses is provided. The method involves administering to an animal having an organ or tissue a medicament having an antigenic composition having antigenic determinants selected or formulated so that together the antigenic determinants are specific for at least one microbial pathogen that is pathogenic in the organ or tissue, extracting a quantifiable immune sample from the organ or tissue, measuring a characteristic of the immune response in the organ or tissue in the quantifiable immune sample following the administration of the medicament, and, comparing the characteristic of the immune response in the quantifiable immune sample to a corresponding characteristic of the immune response in a reference immune sample obtained from a corresponding organ or tissue. Optionally, the reference immune sample may be obtained from the corresponding organ or tissue in the animal prior to the step of administering the medicament. Optionally, the reference immune sample may be obtained from the corresponding organ or tissue in a second animal. Optionally, the animal may have an infection situated in the organ or tissue.

Comparing the characteristic of the immune response may involve comparing, in the quantifiable and reference immune samples, an indication of the numbers of any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Further, comparing the characteristic of the immune response may involve comparing a shift in an activation state of macrophages. Optionally, the macrophages may shift from being M2-like macrophages to being M1-like macrophages. Further and optionally, the macrophages may shift from being M1-like macrophages to being M2-like macrophages.

Optionally, comparing the characteristic of the immune response may involve identifying, in the quantifiable and reference immune samples, cellular markers on any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages.

Optionally, comparing the characteristic of the immune response may involve identifying, in the quantifiable and reference immune samples, cytokines produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. As detailed herein, the macrophages may include any one or more of the following: M1-like macrophages or M2-like macrophages. Optionally, the cytokines are produced as a result of a shift in an activation state of the macrophages. Optionally, the macrophages shift from being M2-like macrophages to being M1-like macrophages. Further and optionally, the macrophages shift from being M1-like macrophages to being M2-like macrophages.

Optionally, comparing the characteristic of the immune response may involve identifying, in the quantifiable and reference immune samples, differential gene expression produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, the differential gene expression is produced as a result of a shift in an activation state of the macrophages. Optionally, macrophages may shift from being M2-like macrophages to being M1-like macrophages. Further and optionally, the macrophages shift from being M1-like macrophages to being M2-like macrophages.

Optionally, the medicament may be administered at an administration site in successive doses given at a dosage interval of between one hour and one month, over a dosage duration of at least one week. Optionally, the medicament may be administered intradermally or subcutaneously. Optionally, the medicament may be administered in a dose so that each dose is effective to cause a visible localized inflammatory immune response at the administration site. Optionally, the medicament may be administered so that visible localized inflammation at the administration site occurs within 1 to 48 hours. Further and optionally, the animal may be a mammal. Optionally, the animal may be a human or a mouse.

In another aspect, a method of selecting a therapeutic preparation suitable for treating an individual for an infection in a specific organ or tissue is provided. The method involves providing an animal having an infection situated in a specific organ or tissue, providing a test preparation having one or more antigenic determinants of a microbial pathogen which is pathogenic in the corresponding specific organ or tissue in a healthy individual, measuring a characteristic of the immune response in a reference immune sample obtained from the organ or tissue of the animal, administering the test preparation to the animal, measuring a characteristic of the immune response in a quantifiable immune sample obtained from a corresponding organ or tissue of the animal, comparing the characteristic of the immune response in the in the reference and quantifiable immune samples, and treating an enhanced characteristic of the immune response in the quantifiable immune sample compared to the reference immune sample as an indication of the suitability of the test preparation as a therapeutic preparation. Optionally, the animal is sacrificed before the quantifiable immune sample has been obtained.

Optionally, comparing the characteristic of the immune response may involve comparing, in the quantifiable and reference immune samples, an indication of the numbers of any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Optionally, comparing the characteristic of the immune response may involve comparing a shift in an activation state of macrophages. Optionally, the macrophages may shift from being M2-like macrophages to being M1-like macrophages. Further and optionally, the macrophages may shift from being M1-like macrophages to being M2-like macrophages.

Optionally, comparing the characteristic of the immune response may involve identifying, in the quantifiable and reference immune samples, cellular markers on any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages.

Optionally, comparing the characteristic of the immune response may involve identifying, in the quantifiable and reference immune samples, cytokines produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, the cytokines are produced as a result of a shift in an activate state of the macrophages. Optionally, the macrophages may shift from being M2-like macrophages to being M1-like macrophages. Further, the macrophages may shift from being M1-like macrophages to being M2-like macrophages.

Further and optionally, comparing the characteristic of the immune response may involve identifying, in the quantifiable and reference immune samples, differential gene expression produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Optionally, the differential gene expression may be produced as a result of a shift in an activation state of the macrophages. Optionally, the macrophages may shift from being M2-like macrophages to being M1-like macrophages. Further and optionally, the macrophages may shift from being M1-like macrophages to being M2-like macrophages.

In another aspect, a method of selectively targeting an immune response to an infected tissue or an organ in a human subject is provided. The method involves administering to the subject a medicament having an effective amount of a microbial pathogen antigenic composition, wherein the microbial pathogen may be pathogenic in the specific organ or tissue of the subject in which there is an infection caused by a heterologous micro-organism, and the antigenic composition comprises antigenic determinants that together are specific for the microbial pathogen. Optionally, the antigenic composition may include a whole killed bacterial cell composition. Optionally, the medicament may be administered to the subject in an amount and for a time that is effective to up-regulate an anti-microbial immune response in the organ or tissue of the subject in which there is an infection caused by a heterologous micro-organism. Optionally, the method may further involve measuring a characteristic of the immune response. The method also includes prophylactic treatment of infections, by immuneprotective vaccination.

In another aspect, a method for treating a human subject for an infection, or a pathology associated with a microbial infection, situated in a tissue or an organ is provided. The method involves administering to the subject a medicament having an effective amount of an antigenic composition comprising a microbial pathogen, such as whole killed bacterial cell or viral compositions, wherein the microbial pathogen is pathogenic in the specific organ or tissue of the subject within which the heterologous microbial infection is situated or within which the future infection is to be prevented. The medicament may be administered to the subject in an amount and for a time that is effective to modulate an immune response in the target organ or tissue. In this way, the invention provides site specific immunomodulators (SSTs), which elicit an immunological response in a target organ or tissue. In select embodiments, the target organ or tissue may be distinct or distant from the site of administration. Optionally, the modulation of the immune response may involve a shift in the activation state of macrophages. Optionally, the modulation of the immune response may involve shifting from a M2-like macrophage response to a M1-like macrophage response. The modulation of the immune response may involve a shift from M1-like macrophages to M2-like macrophages, as those terms are defined herein. Optionally and without limitation, the method may further involve measuring a characteristic of the immune response.

Optionally, comparing the characteristic of the immune response may involve comparing, in the quantifiable and reference immune samples, an indication of the numbers of any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Optionally, comparing the characteristic of the immune response may involve comparing a shift in an activation state of macrophages. Further and optionally, the macrophages may shift from being M2-like macrophages to being M1-like macrophages. Optionally, the macrophages may shift from being M1-like macrophages to being M2-like macrophages.

Further and without limitation, comparing the characteristic of the immune response may involve identifying, in the quantifiable and reference immune samples, cellular markers on any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, comparing the characteristic of the immune response may involve identifying, in the quantifiable and reference immune samples, cytokines produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Further, cytokines may be produced as a result of a shift in an activation state of the macrophages. The macrophages may shift from being M2-like macrophages to being M1-like macrophages. Optionally, the macrophages may shift from being M1-like macrophages to being M2-like macrophages.

Further and optionally, comparing the characteristic of the immune response may involve identifying, in the quantifiable and reference immune samples, differential gene expression produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, the differential gene expression may be produced as a result of a shift in an activation state of the macrophages. Further and optionally, the macrophages may shift from being M2-like macrophages to being M1-like macrophages. The macrophages may shift from being M1-like macrophages to being M2-like macrophages.

In another aspect, a method of monitoring efficacy of a treatment regime in an individual being treated for an infection in a specific organ or tissue is provided. The method involves measuring a characteristic of an immune response in a post-treatment immune sample obtained from the specific organ or tissue after the individual has been subject to the treatment regime for a period of time, wherein the presence of a characteristic of the immune response which is greater in magnitude than would be expected had the individual not been subject to the treatment regime, is indicative of the efficacy of the treatment regime; and the treatment regime involves administering a preparation comprising one or more antigenic determinants of a microbial pathogen which is pathogenic in the corresponding specific organ or tissue in a healthy subject.

The method detailed herein may further involve measuring the characteristic of the immune response in a pre-treatment reference sample, wherein the pre-treatment reference sample was obtained from the specific organ or tissue before, at the same time as or after commencement of the treatment regime, but prior to obtaining the post-treatment immune sample, and comparing the characteristic of the immune response in the pre-treatment and post-treatment samples, wherein an increase in the magnitude of the immune response in the post-treatment immune sample compared to the pre-treatment reference sample is indicative of the efficacy of the treatment regime. Optionally, measuring the characteristic of the immune response may involve determining an indication of the number of inflammatory monocytes in a sample of the organ or tissue. Optionally, measuring the characteristic of the immune response may involve determining an indication of the number of macrophages in a sample of the organ or tissue. The macrophages may include any one or more of the following: M1-like macrophages or M2-like macrophages.

As detailed herein in another aspect, the invention also provides methods for formulating an immunogenic composition for treating an infection situated in a specific organ or tissue in a mammal, such as human patient. The method may include selecting at least one microbial pathogen that is naturally pathogenic in the organ or tissue of the mammal within which the heterologous microbial infection is situated. An antigenic composition may be produced that includes antigenic determinants that together are specific for or characteristic of the microbial pathogen.

A diagnostic step may be used to identify the specific organ or tissue within which the infection is situated, prior to producing the antigenic composition targeted to the site of the infection. The site of the infection may be a primary site, or a secondary site of metastasis. The antigenic composition may be sufficiently specific that it would be capable of eliciting an immune response in the mammal specific to the microbial pathogen. The antigenic composition may be a bacterial composition, for example derived from a bacterial species or species that are endogenous to the flora of the patient or from an exogenous species or species. In alternative embodiments, the antigenic composition may be derived from a virus or viruses. Accordingly, the microbial pathogen from which the antigenic composition is derived may be a virus. The microbial pathogen may be killed. In alternative embodiments, the microbial pathogen may be live or attenuated. Immunogenic compositions of the invention may also be formulated or administered with antimicrobial modalities, such as an NSAID. The site of administration may be at a site distant from the site of the infection, for example in an organ or tissue that is not the organ or tissue within which the heterologous infection is situated, for example the skin or subcutaneous tissue.

The antigenic composition may for example be formulated for subcutaneous injection, intradermal injection or oral administration. In embodiments for subcutaneous or intradermal injection, the dosing or formulation of the antigenic composition may be adjusted in order to produce a localized immune reaction visible in the skin at the site of administration, for example an area of inflammation from 2 mm to 100 mm in diameter appearing, for example, 2-48 hours after administration and lasting, for example, 2-72 hours or longer. The antigenic composition may be formulated for repeated subcutaneous or intradermal administration, for example at alternating successive sites.

In some embodiments, the invention involves methods of treating a mammal for an infection situated in a tissue or an organ. In alternative embodiments, the treatment may anticipate the development of the heterologous infection in the tissue, for example if the site of a primary infection suggests the likelihood of the spread of the infection to a particular tissue or organ, then the patient may be prophylactically treated to prevent or ameliorate metastasis to that tissue or organ. The method may include administering to the subject an effective amount of an antigenic composition comprising antigenic determinants that together are specific for at least one microbial pathogen. An aspect of the invention involves the use of a microbial pathogen that is pathogenic in the specific organ or tissue of the mammal within which the heterologous infection is situated. The antigenic composition may be administered, for example by subcutaneous or intradermal injection at an administration site, in successive doses given at a dosage interval, for example of between one hour and one month, over a dosage duration, for example of at least 1 week, 2 weeks, 2 months, 6 months, 1, 2, 3, 4, or 5 years or longer. Each injection dose may for example be metered so that it is effective to cause visible localized inflammation at the administration site, appearing, for example, 1-48 hours after injection.

In another aspect, methods are provided for treating heterologous infections of a specific organ or tissue in a subject by administering one or more antigens of one or more microbial pathogens, such as bacterial, viral or fungal species that are pathogenic in the specific organ or tissue.

In alternative embodiments, the pathogenic microbial species may be capable of causing infection naturally, (i.e., without human intervention) in the specific organ or tissue in a healthy subject, or may have caused an infection in the specific organ or tissue in a healthy subject. In alternative embodiments, the antigen may be administered by administering preparations derived from whole cells of a microbial species. In alternative embodiments, the method may, for example, include administering at least two or more microbial species, or administering at least three or more microbial species, and the microbes may be bacteria or viruses. In alternative embodiments, the method may further include administering a supplement or an adjuvant. An aspect of the invention involves administering antigenic compositions so as to elicit an immune response in said subject.

In alternative embodiments, the microbial pathogen in the antigenic composition may be killed, and thus rendered non-infectious. In some embodiments, the antigenic composition is administered at a site distant from the heterologous infection site, and in selected embodiments of this kind, methods of the invention may be carried out so that they do not produce infection at the heterologous infection site.

As detailed herein, various aspects of the invention involve treating heterologous infections. In this context, treatment may be carried out so as to provide a variety of outcomes. For example, treatment may: provoke an immune reaction that is effective to inhibit or ameliorate the growth or proliferation of an infection; inhibit the growth or proliferation of heterologous micro-organisms; cause remission of an infection; improve quality of life; reduce the risk of recurrence of an infection; inhibit spread of an infection; or, improve patient survival rates in a patient population. In this context, extending the life expectancy of a patient, or patient population, means to increase the number of patients who survive for a given period of time following a particular diagnosis. In some embodiments, treatment may be of patients who have not responded to other treatments, such as patients for whom a chemotherapy or surgery has not been an effective treatment. Treatment in alternative embodiments may for example be before or after onset of heterologous infection. For example prophylactic treatment may be undertaken, for example of patients diagnosed as being at risk of a particular heterologous infection.

Bacteria and Bacterial Colonizations and Infections

Most animals are colonized to some degree by other organisms, such as bacteria, which generally exist in symbiotic or commensal relationships with the host animal. Thus, many species of normally harmless bacteria are found in healthy animals, and are usually localized to the surface of specific organs and tissues. Often, these bacteria aid in the normal functioning of the body. For example, in humans, symbiotic *Escherichia coli* bacteria may be found in the intestine, where they promote immunity and reduce the risk of infection with more virulent pathogens.

Bacteria that are generally harmless, such as *Escherichia coli*, can cause infection in healthy subjects, with results ranging from mild to severe infection to death. Whether or not a bacterium is pathogenic (i.e., causes infection) depends to some extent on factors such as the route of entry and access to specific host cells, tissues, or organs; the intrinsic virulence of the bacterium; the amount of the bacteria present at the site of potential infection; or the health of the host animal. Thus, bacteria that are normally harmless can become pathogenic given favorable conditions for infection, and even the most virulent bacterium requires specific circumstances to cause infection. Accordingly, microbial species that are members of the normal flora can be pathogens when they move beyond their normal ecological role in the endogenous flora. For example, endogenous species can cause infection outside of their ecological niche in regions of anatomical proximity, for example by contiguous spread. When this occurs, these normally harmless endogenous bacteria are considered pathogenic.

Specific bacterial species and viruses are known to cause infections in specific cells, tissues, or organs in otherwise healthy subjects. Examples of bacteria and viruses that commonly cause infections in specific organs and tissues of the body are listed below; it will be understood that these examples are not intended to be limiting and that a skilled person would be able to readily recognize and identify infectious or pathogenic bacteria that cause infections, or commonly cause infections, in various organs and tissues in healthy adults (and recognize the relative frequency of infection with each bacterial species) based on the knowledge in the field as represented, for example, by the following publications: Manual of Clinical Microbiology 8th Edition, Patrick Murray, Ed., 2003, ASM Press American Society for Microbiology, Washington D.C., USA; Mandell, Douglas, and Bennett's Principles and Practice of Infectious Diseases 5th Edition, G. L. Mandell, J. E. Bennett, R. Dolin, Eds., 2000, Churchill Livingstone, Philadelphia, Pa., USA, all of which are incorporated by reference herein.

Infections of the skin are commonly caused by the following bacterial species: *Staphylococcus aureus*, Beta hemolytic streptococci group A, B, C or G, *Corynebacterium diptheriae, Corynebacterium ulcerans*, or *Pseudomonas aeruginosa*; or viral pathogens: rubeola, rubella, varicella-zoster, echoviruses, coxsackieviruses, adenovirus, vaccinia, herpes simplex, or parvo B19.

Infections of the soft tissue (e.g., fat and muscle) are commonly caused by the following bacterial species: *Streptococcus pyogenes, Staphylococcus aureus, Clostridium perfringens*, or other *Clostridium* spp.; or viral pathogens: influenza, or coxsackieviruses.

Infections of the breast are commonly caused by the following bacterial species: *Staphylococcus aureus*, or *Streptococcus pyogenes*.

Infections of the lymph nodes of the head and neck are commonly caused by the following bacterial species: *Staphylococcus aureus*, or *Streptococcus pyogenes*; or viral pathogens: Epstein-Barr, cytomegalovirus, adenovirus, measles, rubella, herpes simplex, coxsackieviruses, or varicella-zoster.

Infections of the lymph nodes of the arm/axillae are commonly caused by the following bacterial species: *Staphylococcus aureus*, or *Streptococcus pyogenes*; or viral pathogens: measles, rubella, Epstein-Barr, cytomegalovirus, adenovirus, or varicella-zoster.

Infections of the lymph nodes of the mediastinum are commonly caused by the following bacterial species: viridans streptococci, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, cytomegalovirus, varicella-zoster, or adenovirus.

Infections of the pulmonary hilar lymph nodes are commonly caused by the following bacterial species: *Streptococcus pneumoniae, Moraxella catarrhalis, Mycoplasma pneumoniae, Klebsiella pneumoniae, Haemophilus influenza, Chlamydophila pneumoniae, Bordetella pertussis* or

*Mycobacterium tuberculosis*; or viral pathogens: influenza, adenovirus, rhinovirus, coronavirus, parainfluenza, respiratory syncytial virus, human metapneumovirus, or coxsackievirus.

Infections of the intra-abdominal lymph nodes are commonly caused by the following bacterial species: *Yersinia enterocolitica, Yersinia pseudotuberculosis, Salmonella* spp., *Streptococcus pyogenes, Escherichia coli, Staphylococcus aureus,* or *Mycobacterium tuberculosis*; or viral pathogens: measles, rubella, Epstein-Barr, cytomegalovirus, varicella-zoster, adenovirus, influenza, or coxsackieviruses.

Infections of the lymph nodes of the leg/inguinal region are commonly caused by the following bacterial species: *Staphylococcus aureus,* or *Streptococcus pyogenes*; or viral pathogens: measles, rubella, Epstein-Barr, cytomegalovirus, or herpes simplex.

Infections of the blood (i.e., septicemia) are commonly caused by the following bacterial species: *Staphylococcus aureus, Streptococcus pyogenes,* coagulase-negative staphylococci, *Enterococcus* spp., *Escherichia coli, Klebsiella* spp., *Enterobacter* spp., *Proteus* spp., *Pseudomonas aeruginosa, Bacteroides fragilis, Streptococcus pneumoniae,* or group B streptococci; or viral pathogens: rubeola, rubella, varicella-zoster, echoviruses, coxsackieviruses, adenovirus, Epstein-Barr, herpes simplex, or cytomegalovirus.

Infections of the bone are commonly caused by the following bacterial species: *Staphylococcus aureus,* coagulase-negative staphylococci, *Streptococcus pyogenes, Streptococcus pneumoniae, Streptococcus agalactiae,* other streptococci spp., *Escherichia coli, Pseudomonas* spp., *Enterobacter* spp., *Proteus* spp., or *Serratia* spp.; or viral pathogens: parvovirus B19, rubella, or hepatitis B.

Infections of the joint are commonly caused by the following bacterial species: *Staphylococcus aureus,* coagulase-negative staphylococci, *Streptococcus pyogenes, Streptococcus pneumoniae, Streptococcus agalactiae,* other streptococci spp., *Escherichia coli, Pseudomonas* spp., *Enterobacter* spp., *Proteus* spp., *Serratia* spp., *Neisseria gonorrhea, salmonella* species, *Mycobacterim tuberculosis, Hemophilus influenza*; or viral pathogens: parvovirus B19, rubella, hepatitis B; or fungal pathogen: *Scedosporium prolificans*

Infections of the meninges are commonly caused by the following bacterial species: *Haemophilus influenzae, Neisseria meningitidis, Streptococcus pneumoniae, Streptococcus agalactiae,* or *Listeria monocytogenes*; or viral pathogens: echoviruses, coxsackieviruses, other enteroviruses, or mumps.

Infections of the brain are commonly caused by the following bacterial species: *Streptococcus* spp. (including *S. anginosus, S. constellatus, S. intermedius*), *Staphylococcus aureus, Bacteroides* spp., *Prevotella* spp., *Proteus* spp., *Escherichia coli, Klebsiella* spp., *Pseudomonas* spp., *Enterobacter* spp., or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the spinal cord are commonly caused by the following bacterial species: *Haemophilus influenzae, Neisseria meningitidis, Streptococcus pneumoniae, Streptococcus agalactiae, Listeria monocytogenes,* or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the eye/orbit are commonly caused by the following bacterial species: *Staphylococcus aureus, Streptococcus pyogenes, Streptococcus pneumoniae, Streptococcus milleri, Escherichia coli, Bacillus cereus, Chlamydia trachomatis, Haemophilus influenza, Pseudomonas* spp., *Klebsiella* spp., or *Treponema pallidum*; or viral pathogens: adenoviruses, herpes simplex, varicella-zoster, or cytomegalovirus.

Infections of the salivary glands are commonly caused by the following bacterial species: *Staphylococcus aureus,* viridans streptococci (e.g., *Streptococcus salivarius, Streptococcus sanguis, Streptococcus mutans*), *Peptostreptococcus* spp., or *Bacteroides* spp., or other oral anaerobes; or viral pathogens: mumps, influenza, enteroviruses, or rabies.

Infections of the mouth are commonly caused by the following bacterial species: *Prevotella melaninogenicus,* anaerobic streptococci, viridans streptococci, *Actinomyces* spp., *Peptostreptococcus* spp., or *Bacteroides* spp., or other oral anaerobes; or viral pathogens: herpes simplex, coxsackieviruses, or Epstein-Barr.

Infections of the tonsils are commonly caused by the following bacterial species: *Streptococcus pyogenes,* or Group C or G B-hemolytic streptococci; or viral pathogens: rhinoviruses, influenza, coronavirus, adenovirus, parainfluenza, respiratory syncytial virus, or herpes simplex.

Infections of the sinuses are commonly caused by the following bacterial species: *Streptococcus pneumoniae, Haemophilus influenza, Moraxella catarrhalis,* α-streptococci, anaerobic bacteria (e.g., *Prevotella* spp.), or *Staphylococcus aureus*; or viral pathogens: rhinoviruses, influenza, adenovirus, or parainfluenza.

Infections of the nasopharynx are commonly caused by the following bacterial species: *Streptococcus pyogenes,* or Group C or G B-hemolytic streptococci; or viral pathogens: rhinoviruses, influenza, coronavirus, adenovirus, parainfluenza, respiratory syncytial virus, or herpes simplex.

Infections of the thyroid are commonly caused by the following bacterial species: *Staphylococcus aureus, Streptococcus pyogenes,* or *Streptococcus pneumoniae*; or viral pathogens: mumps, or influenza.

Infections of the larynx are commonly caused by the following bacterial species: *Mycoplasma pneumoniae, Chlamydophila pneumoniae,* or *Streptococcus pyogenes*; or viral pathogens: rhinovirus, influenza, parainfluenza, adenovirus, corona virus, or human metapneumovirus.

Infections of the trachea are commonly caused by the following bacterial species: *Mycoplasma pneumoniae*; or viral pathogens: parainfluenza, influenza, respiratory syncytial virus, or adenovirus.

Infections of the bronchi are commonly caused by the following bacterial species: *Mycoplasma pneumoniae, Chlamydophila pneumoniae, Bordetella pertussis, Streptococcus pneumoniae,* or *Haemophilus influenzae*; or viral pathogens: influenza, adenovirus, rhinovirus, coronavirus, parainfluenza, respiratory syncytial virus, human metapneumovirus, or coxsackievirus.

Infections of the lung are commonly caused by the following bacterial species: *Streptococcus pneumoniae, Moraxella catarrhalis, Mycoplasma pneumoniae, Klebsiella pneumoniae,* or *Haemophilus influenza*; or viral pathogens: influenza, adenovirus, respiratory syncytial virus, or parainfluenza.

Infections of the pleura are commonly caused by the following bacterial species: *Staphylococcus aureus, Streptococcus pyogenes, Streptococcus pneumoniae, Haemophilus influenzae, Bacteroides fragilis, Prevotella* spp., *Fusobacterium nucleatum, peptostreptococcus* spp., or *Mycobacterium tuberculosis*; or viral pathogens: influenza, adenovirus, respiratory syncytial virus, or parainfluenza.

Infections of the mediastinum are commonly caused by the following bacterial species: viridans streptococci, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, or cytomegalovirus.

Infections of the heart are commonly caused by the following bacterial species: *Streptococcus* spp. (including *S. mitior, S. bovis, S. sanguis, S. mutans, S. anginosus*), *Enterococcus* spp., *Staphylococcus* spp., *Corynebacterium diptheriae, Clostridium perfringens, Neisseria meningitidis*, or *Salmonella* spp.; or viral pathogens: enteroviruses, coxsackieviruses, echoviruses, poliovirus, adenovirus, mumps, rubeola, or influenza.

Infections of the esophagus are commonly caused by the following bacterial species: *Actinomyces* spp., *Mycobacterium avium, Mycobacterium tuberculosis*, or *Streptococcus* spp.; or viral pathogens: cytomegalovirus, herpes simplex, or varicella-zoster.

Infections of the stomach are commonly caused by the following bacterial species: *Streptococcus pyogenes* or *Helicobacter pylori*; or viral pathogens: cytomegalovirus, herpes simplex, Epstein-Barr, rotaviruses, noroviruses, or adenoviruses.

Infections of the small bowel are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the colon/rectum are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the anus are commonly caused by the following bacterial species: *Streptococcus pyogenes, Bacteroides* spp., *Fusobacterium* spp., anaerobic streptococci, *Clostridium* spp., *Escherichia coli, Enterobacter* spp., *Pseudomonas aeruginosa*, or *Treponema pallidum*; or viral pathogens: herpes simplex.

Infections of the perineum are commonly caused by the following bacterial species: *Escherichia coli, Klebsiella* spp., *Enterococcus* spp., *Bacteroides* spp., *Fusobacterium* spp., *Clostridium* spp., *Pseudomonas aeruginosa*, anaerobic streptococci, *Clostridium* spp., or *Enterobacter* spp.; or viral pathogens: herpes simplex.

Infections of the liver are commonly caused by the following bacterial species: *Escherichia coli, Klebsiella* spp., *Streptococcus* (anginosus group), *Enterococcus*, spp. other viridans streptococci, or *Bacteroides* spp.; or viral pathogens: hepatitis A, Epstein-Barr, herpes simplex, mumps, rubella, rubeola, varicella-zoster, coxsackieviruses, or adenovirus.

Infections of the gallbladder are commonly caused by the following bacterial species: *Escherichia coli, Klebsiella* spp., *Enterobacter* spp., enterococci, *Bacteroides* spp., *Fusobacterium* spp., *Clostridium* spp., *Salmonella enteriditis, Yersinia enterocolitica*, or *Shigella flexneri*.

Infections of the biliary tract are commonly caused by the following bacterial species: *Escherichia coli, Klebsiella* spp., *Enterobacter* spp., enterococci, *Bacteroides* spp., *Fusobacterium* spp., *Clostridium* spp., *Salmonella enteriditis, Yersinia enterocolitica*, or *Shigella flexneri*; or viral pathogens: hepatitis A, Epstein-Barr, herpes simplex, mumps, rubella, rubeola, varicella-zoster, cocsackieviruses, or adenovirus.

Infections of the pancreas are commonly caused by the following bacterial species: *Escherichia coli, Klebsiella* spp., *Enterococcus* spp., *Pseudomonas* spp., *Staphylococcal* spp., *Mycoplasma* spp., *Salmonella typhi, Leptospirosis* spp., or *Legionella* spp.; or viral pathogens: mumps, coxsackievirus, hepatitis B, cytomegalovirus, herpes simplex 2, or varicella-zoster.

Infections of the spleen are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: Epstein-Barr, cytomegalovirus, adenovirus, measles, rubella, coxsackieviruses, or varicella-zoster.

Infections of the adrenal gland are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: varicella-zoster.

Infections of the kidney are commonly caused by the following bacterial species: *Escherichia coli, Proteus mirabilis, Proteus vulgatus, Providentia* spp., *Morganella* spp., *Enterococcus faecalis*, or *Pseudomonas aeruginosa*; or viral pathogens: BK virus, or mumps.

Infections of the ureter are commonly caused by the following bacterial species: *Escherichia coli, Proteus mirabilis, Proteus vulgatus, Providentia* spp., *Morganella* spp., or *Enterococcus* spp.

Infections of the bladder are commonly caused by the following bacterial species: *Escherichia coli, Proteus mirabilis, Proteus vulgatus, Providentia* spp., *Morganella* spp., *Enterococcus faecalis*, or *Corynebacterium jekeum*; or viral pathogens: adenovirus, or cytomegalovirus.

Infections of the peritoneum are commonly caused by the following bacterial species: *Staphylococcus aureus, Streptococcus pyogenes, Streptococcus pneumonia, Escherichia coli, Klebsiella* spp., *Proteus* spp., enterococci, *Bacteroides fragilis, Prevotella melaninogenica, Peptococcus* spp., *Peptostreptococcus* spp., *Fusobacterium* spp., or *Clostridium* spp.

Infections of the retroperitoneal area are commonly caused by the following bacterial species: *Escherichia coli*, or *Staphylococcus aureus*.

Infections of the prostate are commonly caused by the following bacterial species: *Escherichia coli, Klebsiella* spp., *Enterobacter* spp., *Proteus mirabilis*, enterococci spp., *Pseudomonas* spp., *Corynebacterium* spp., or *Neisseria gonorrhoeae*; or viral pathogens: herpes simplex.

Infections of the testicle are commonly caused by the following bacterial species: *Escherichia coli, Klebsiella pneumoniae, Pseudomonas aeruginosa, Staphylococcus* spp., *Streptococcus* spp., or *Salmonella enteriditis*; or viral pathogens: mumps, coxsackievirus, or lymphocytic choriomeningitis virus.

Infections of the penis are commonly caused by the following bacterial species: *Staphylococcus aureus, Streptococcus pyogenes, Neisseria gonorrhoeae*, or *Treponema pallidum*; or viral pathogens: herpes simplex.

Infections of the ovary/adnexae are commonly caused by the following bacterial species: *Neisseria gonorrhoeae, Chlamydia trachomatis, Gardenerella vaginalis, Prevotella* spp., *Bacteroides* spp., *Peptococcus* spp. *Streptococcus* spp., or *Escherichia coli*.

Infections of the uterus are commonly caused by the following bacterial species: *Neisseria gonorrhoeae, Chlamydia trachomatis, Gardenerella vaginalis, Prevotella* spp., *Bacteroides* spp., *Peptococcus* spp., *Streptococcus* spp., or *Escherichia coli*.

Infections of the cervix are commonly caused by the following bacterial species: *Neisseria gonorrhoeae, Chlamydia trachomatis,* or *Treponema pallidum*; or viral pathogens: herpes simplex.

Infections of the vagina are commonly caused by the following bacterial species: *Gardenerella vaginalis, Prevotella* spp., *Bacteroides* spp., peptococci spp., *Escherichia coli, Neisseria gonorrhoeae, Chlamydia Trachomatis,* or *Treponema pallidum*; or viral pathogens: herpes simplex.

Infections of the vulva are commonly caused by the following bacterial species: *Staphylococcus aureus, Streptococcus pyogenes,* or *Treponema pallidum*; or viral pathogens: herpes simplex.

Bacterial Strains/Viral Subtypes

It will be understood by a skilled person in the art that bacterial species are classified operationally as collections of similar strains (which generally refers to groups of presumed common ancestry with identifiable physiological but usually not morphological distinctions, and which may be identified using serological techniques against bacterial surface antigens). Thus, each bacterial species (e.g., *Streptococcus pneumoniae*) has numerous strains (or serotypes), which may differ in their ability to cause infection or differ in their ability to cause infection in a particular organ/site. For example, although there are at least 90 serotypes of *Streptococcus pneumoniae*, serotypes 1, 3, 4, 7, 8, and 12 are most frequently responsible for pneumococcal disease in humans.

As a second example, certain strains of *Escherichia coli*, referred to as extraintestinal pathogenic *E. coli* (ExPEC), are more likely to cause urinary tract infection or other extraintestinal infections such as neonatal meningitis, whereas other strains, including enterotoxigenic *E. coli* (ETEC), enteropathogenic *E. coli* (EPEC), enterohemorrhagic *E. coli* (EHEC), Shiga toxin-producing *E. coli* (STEC), enteroaggregative *E. coli* (EAEC), enteroinvasive *E. coli* (EIEC) and diffuse adhering *E. coli* (DAEC) are more likely to cause gastrointestinal infection/diarrhea. Even among the subcategory of ExPEC strains, specific virulence factors (e.g., production of type-1 fimbriae) enable certain strains to be more capable of causing infection of the bladder, while other virulence factors (e.g., production of P fimbriae) enable other strains to be more capable of causing infection in the kidneys. In accordance with the present invention, an ExPEC strain(s) that is more likely to cause infection in the bladder may be chosen for a formulation to target bladder infection, whereas an ExPEC strain(s) that is more likely to cause infection in the kidney may be chosen for a formulation to target kidney infection. Likewise, one or more of an ETEC, EPEC, EHEC, STEC, EAEC, EIEC or DAEC strains of *E. coli* (i.e., strains that cause colon infection), may be chosen for a formulation to treat colon infections.

Similarly, there may be numerous subtypes of specific viruses. For example, there are three types of influenza viruses, influenza A, influenza B and influenza C, which differ in epidemiology, host range and clinical characteristics. For example, influenza A is more likely to be associated with viral lung infection, whereas influenza B is more likely to be associated with myositis (i.e., muscle infection). Furthermore, each of these three types of influenza virus have numerous subtypes, which also may differ in epidemiology, host range and clinical characteristics. In accordance with the present invention, one may choose an influenza A subtype most commonly associated with lung infection to target heterologous lung infections, whereas one may choose an influenza B strain most commonly associated with myositis to treat infections of the muscle/soft tissues.

It is understood that a clinical microbiologist skilled in the art would therefore be able to select, based on the present disclosure and the body of art relating to bacterial strains for each species of bacteria (and viral subtypes for each type of virus), the strains of a particular bacterial species (or subtype of a particular virus) to target a specific organ or tissue. In this way, the invention provides site specific immunomodulators (SSTs), in the sense that the formulations and treatments of the invention elicit an immunological response in a target organ or tissue, and that target may be distinct or distant from the site of administration.

Microbial Compositions, Dosages, and Administration

The compositions of the invention include antigens of pathogenic microbial (bacterial or viral) species that are pathogenic in a specific tissue or organ. The compositions may include whole bacterial species, or may include extracts or preparations of the pathogenic bacterial species of the invention, such as cell wall or cell membrane extracts, or whole cells, or exotoxins, or whole cells and exotoxins. The compositions may also include one or more isolated antigens from one or more of the pathogenic bacterial species of the invention; in some embodiments, such compositions may be useful in situations where it may be necessary to precisely administer a specific dose of a particular antigen, or may be useful if administering a whole bacterial species or components thereof (e.g., toxins) may be harmful. Pathogenic bacterial species may be available commercially (from, for example, ATCC (Manassas, Va., USA), or may be clinical isolates from subjects having a bacterial infection of a tissue or organ (e.g., pneumonia).

The microbial compositions of the invention can be provided alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans. As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration, including subcutaneous, intradermal, intravenous, parenteral, intraperitoneal, intramuscular, sublingual, inhalational, intratumoral or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound (i.e., the specific bacteria, bacterial antigens, or compositions thereof of the invention), use thereof in the pharmaceutical compositions of the invention is contemplated. Supplementary active compounds can also be incorporated into the compositions.

Conventional pharmaceutical practice may be employed to provide suitable formulations or compositions to administer the compounds to subjects suffering from an infection. Any appropriate route of administration may be employed, for example, parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, intratumoral, sublingual or oral administration. Therapeutic formulations may be in the form of liquid solutions or suspensions; for oral administration, formulations may be in the form of tablets or capsules; for intranasal formulations, in the form of powders, nasal drops, or aerosols; and for sublingual formulations, in the form of drops, aerosols or tablets.

Methods well known in the art for making formulations are found in, for example, "Remington's Pharmaceutical Sciences" (20th edition), ed. A. Gennaro, 2000, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the pathogenic bacterial species are administered to an individual in an amount effective to stop or slow progression of the infection, or to increase survival of the subject.

An "effective amount" of a pathogenic microbial species or antigen thereof according to the invention includes a therapeutically effective amount or a prophylactically effective amount. A "therapeutically effective amount" refers to an amount effective, at dosages and for periods of time necessary, to achieve the desired therapeutic result, such as reduction or elimination of the heterologous infection, prevention of microbial infection processes, slowing the growth of the tumour, or an increase in survival time beyond that which is expected using for example the SEER database. A therapeutically effective amount of a pathogenic microbial (bacterial or viral) species or antigen(s) thereof may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the pathogenic bacterial species or virus or antigen thereof are outweighed by the therapeutically beneficial effects. A "prophylactically effective amount" refers to an amount effective, at dosages and for periods of time necessary, to achieve the desired prophylactic result, such as prevention of infection, slowing the progress of the infection, reduction or elimination of the heterologous microbial cells.

For administration by subcutaneous or intradermal injection, an exemplary range for therapeutically or prophylactically effective amounts of one or more pathogenic bacterial species may be about 1 million to 100,000 million organisms per ml, or may be 100 million to 7000 million organisms per ml, or may be 500 million to 6000 million organisms per ml, or may be 1000 million to 5000 million organisms per ml, or may be 2000 million to 4000 million organisms per ml, or any integer within these ranges. The total concentration of bacteria per ml may range from 1 million to 100,000 million organisms per ml, or may be 50 million to 7000 million organisms per ml, or may be 100 million to 6000 million organisms per ml, or may be 500 million to 5000 million organisms per ml, or may be 1000 million to 4000 million organisms per ml, or any integer within these ranges. The range for therapeutically or prophylactically effective amounts of antigens of a pathogenic bacterial species may be any integer from 0.1 nM-0.1 M, 0.1 nM-0.05M, 0.05 nM-15 µM or 0.01 nM-10 µM.

It is to be noted that dosage concentrations and ranges may vary with the severity of the condition to be alleviated, or may vary with the subject's immune response. In general, the goal is to achieve an adequate immune response. For administration by subcutaneous or intradermal infection, the extent of an immune response may be determined, for example, by size of delayed local immune skin reaction at the site of injection (e.g., from 0.25 inch to 4 inch diameter). The dose required to achieve an appropriate immune response may vary depending on the individual (and their immune system) and the response desired. Standardized dosages may also be used. In the context of subcutaneous or intradermal administration, if the goal is to achieve a 2 inch local skin reaction, the total bacterial composition dose may, for example, range from 2 million bacteria (e.g., 0.001 ml of a composition with a concentration of 2,000 million organisms per ml) to more than 20,000 million bacteria (e.g., 1 ml of a composition with a concentration of 20,000 million organisms per ml). The concentrations of individual bacterial species or antigens thereof within a composition may also be considered. For example, if the concentration of one particular pathogenic bacterial species, cell size of that species or antigenic load thereof is much higher relative to the other pathogenic bacterial species in the composition, then the local immune skin reaction of an individual may be likely due to its response to this specific bacterial species. In some embodiments, the immune system of an individual may respond more strongly to one bacterial species within a composition than another, depending for example on past history of exposure to infection by a particular species, so the dosage or composition may be adjusted accordingly for that individual. However, in some embodiments detailed herein, an immune response will not be monitored by way of a skin reaction. For example, in some mouse models utilized herein, the effective treatment of such animals with antigenic compositions may not result in corresponding skin reactions. A person skilled in the art will understand that there are alternate ways in which an immune response can be monitored beside relying on the presence or absence of a skin reaction.

For any particular subject, the timing and dose of treatments may be adjusted over time (e.g., timing may be daily, every other day, weekly, monthly) according to the individual need and the professional judgment of the person administering or supervising the administration of the compositions. For example, in the context of subcutaneous or intradermal administration, the compositions may be administered every second day. An initial dose of approximately 0.05 ml may be administered subcutaneously, followed by increases from 0.01-0.02 ml every second day until an adequate skin reaction is achieved at the injection site (for example, a 1 inch to 2 inch diameter delayed reaction of visible redness at the injection site). Once this adequate immune reaction is achieved, this dosing is continued as a maintenance dose. The maintenance dose may be adjusted from time to time to achieve the desired visible skin reaction (inflammation) at the injection site. Dosing may be for a dosage duration, for example of at least 1 week, 2 weeks, 2 months, 6 months, 1, 2, 3, 4, or 5 years or longer.

Oral dosages may for example range from 10 million to 1,000,000 million organisms per dose, comprising antigenic determinants of one or more species. Oral dosages may be given, for example, from 4 times per day, daily or weekly. Dosing may be for a dosage duration, for example of at least 1 week, 2 weeks, 2 months, 6 months, 1, 2, 3, 4, or 5 years or longer.

In some embodiments, the invention may include antigenic compositions administered sublingually or by inhalation, or administered to one or more epithelial tissues (i.e., skin by intradermal or subcutaneous injection; lung epithelium by inhalation; gastrointestinal mucosa by oral ingestion; mouth mucosa by sublingual administration) simultaneously or sequentially. Accordingly, in some embodiments the antigenic compositions of the invention are administered so as to provoke an immune response in an epithelial tissue. In some embodiments, one or more epithelial routes of administration may be combined with one or more additional routes of administration, such as intratumoral, intramuscular or intravenous administration.

In various aspects of the invention, the antigenic compositions that are administered to a patient may be characterized as having an antigenic signature, i.e., a combination of antigens or epitopes that are sufficiently specific that the antigenic composition is capable of eliciting an immune response that is specific to a particular pathogen, such as an adaptive immune response. A surprising and unexpected aspect of the invention is that the non-adaptive or non-specific activation of the immune response that is mediated by these specific antigenic compositions is effective to treat heterologous infections situated in the tissues in which the particular pathogen is pathogenic.

Routes of administration and dosage ranges set forth herein are exemplary only and do not limit the route of administration and dosage ranges that may be selected by medical practitioners. The amount of active compound (e.g., pathogenic bacterial species or viruses or antigens thereof) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of antigenic formulations (i.e. formulations that provoke an immune response), an immunogenically effective amount of a compound or composition of the invention can be provided, alone or in combination with other compounds, such as an immunological adjuvant. The compound may also be linked with a carrier molecule, such as bovine serum albumin or keyhole limpet hemocyanin to enhance immunogenicity. An antigenic composition is a composition that includes materials that elicit a desired immune response. An antigenic composition may select, activate or expand, without limitation: memory B, T cells, neutrophils, monocytes or macrophages of the immune system to, for example, reduce or eliminate the growth or proliferation of heterologous micro-organisms. In some embodiments, the specific pathogenic microbe, virus, viral antigens, bacteria, bacterial antigens, or compositions thereof of the invention are capable of eliciting the desired immune response in the absence of any other agent, and may therefore be considered to be an antigenic composition. In some embodiments, an antigenic composition includes a suitable carrier, such as an adjuvant, which is an agent that acts in a non-specific manner to increase the immune response to a specific antigen, or to a group of antigens, enabling the reduction of the quantity of antigen in any given dose, or the reduction of the frequency of dosage required to generate the desired immune response. A bacterial antigenic composition may include live or dead bacteria capable of inducing an immune response against antigenic determinants normally associated with the bacteria. In some embodiments, an antigenic composition may include live bacteria that are of less virulent strains (attenuated), and therefore cause a less severe infection. In some embodiments the antigenic composition may include live, attenuated or dead viruses capable of inducing an immune response against antigenic determinants normally associated with the virus.

An antigenic composition comprising killed bacteria for administration by injection may be made as follows. The bacteria may be grown in suitable media, and washed with physiological salt solution. The bacteria may then be centrifuged, resuspended in saline solution, and killed with heat. The suspensions may be standardized by direct microscopic count, mixed in required amounts, and stored in appropriate containers, which may be tested for safety, shelf life, and sterility in an approved manner. In addition to the pathogenic bacterial species and/or antigens thereof, a killed bacterial composition suitable for administration to humans may include 0.4% phenol preservative and/or 0.9% sodium chloride. The bacterial composition may also include trace amounts of brain heart infusion (beef), peptones, yeast extract, agar, sheep blood, dextrose, sodium phosphate and/or other media components.

In some embodiments, the bacterial or microbial composition may be used in tablet or capsule form or drops for oral ingestion, as an aerosol for inhalation, or as drops, aerosol or tablet form for sublingual administration.

In antigenic compositions comprising bacteria, the concentrations of specific bacterial species in compositions for subcutaneous or intradermal injection may be about 1 million to 100,000 million organisms per ml, or may be 100 million to 7000 million organisms per ml, or may be 500 million to 6000 million organisms per ml, or may be 1000 million to 5000 million organisms per ml, or may be 2000 million to 4000 million organisms per ml, or any integer within these ranges. The total concentration of bacteria per ml may range from 1 million to 100,000 million organisms per ml, or may be 50 million to 7000 million organisms per ml, or may be 100 million to 6000 million organisms per ml, or may be 500 million to 5000 million organisms per ml, or may be 1000 million to 4000 million organisms per ml, or any integer within these ranges.

In some embodiments, an antigenic microbial composition for treating an infection at a particular site (e.g., an infection of the lung tissue) may include pathogenic microbes that commonly, more commonly, or most commonly cause infection in that tissue or organ (e.g., infection in the lung tissue i.e., pneumonia).

In general, the pathogenic bacterial species and antigens thereof of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population).

As detailed herein and in an aspect of the invention, a method of comparing or provoking specific immune responses is provided. The method involves administering to an animal having an organ or tissue a medicament having an antigenic composition, as defined herein. The antigenic composition may have antigenic determinants selected or formulated so that together the antigenic determinants are specific for at least one microbial pathogen that is pathogenic in the organ or tissue, extracting a quantifiable immune sample from the organ or tissue, measuring a characteristic of the immune response in the organ or tissue in the quantifiable immune sample following the administration of the medicament, and, comparing the characteristic of the immune response in the quantifiable immune sample to a corresponding characteristic of the immune response in a reference immune sample obtained from a corresponding organ or tissue. As used herein, an immune sample would contain sufficient biological material to determine a characteristic of an immune response. As used herein, a "characteristic" of an immune response can include, without limitation, the particular number of a particular immune cell type (e.g., macrophage), or a particular cellular marker (e.g., upregulation of an integrin) or gene product (e.g., a cytokine). The foregoing is provided as an example and is non-limiting.

Optionally, the reference immune sample may be obtained from the corresponding organ or tissue in the animal prior to the step of administering the medicament. In another aspect, the reference immune sample may be obtained from the corresponding organ or tissue in a second animal such that it is specifically contemplated that at least two animals (i.e., an animal from which a reference immune sample is obtained and a second animal from which a quantifiable immune sample) could be used in the methods described herein. Optionally, the animal may have an infection situated in the organ or tissue.

Comparing the characteristic of the immune response may involve comparing, in the quantifiable and reference immune samples, an indication of the numbers of any one or more of the following cells as these cells are known to those skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages.

Macrophages can be defined as either "M1-like macrophages" or "M2-like macrophages". For example, M1-like macrophages are generally understood by those persons skilled in the art to promote a Th1 CD4+ T cell-mediated response (see, for e.g., Biswas and Mantovani (2010), *Nature Immunology* 10:889-96). Moreover, M1-like macrophages are generally understood to have efficient antigen presentation capacity, and to be proficient at killing intracellular pathogens (for e.g., viruses). Moreover, M1-like macrophages are generally understood to be proficient, at least as compared with M2-like macrophages, in playing an immunological role in tumour destruction. Those skilled in the art will appreciate that there are numerous biological markers which can be employed to differentiate between M1-like macrophages and M2-like macrophages. For example, and as detailed herein, the expression of Nos2 is generally understood to correlate with an M1-like macrophage as compared with an M2-like macrophage (see, for e.g., Laskin et al. (2010) *Annual Rev. Pharmacol. Toxicol.* 51: 267-288). Further, and for example, M1-like macrophages are generally understood to produce IL-12 and to be effectively activated by IFN-γ through the IFN-γR (Biswas and Mantovain, supra).

In contrast to M1-like macrophages, M2-like macrophages promote a Th2 CD4+ T cell-mediated response (see, generally: Biswas and Mantovani (2010), *Nature Immunology* 10:889-96). Moreover, M2-like macrophages are generally understood to be effective and encapsulating and clearing extracellular parasites etc. Further, and in comparison to M1-like macrophages, M2-like macrophages are generally understood by those persons skilled in the art as playing a more significant role in immunoregulation both with respect to $T_{reg}$ and B cells (Biswas and Mantovain, supra). Those persons skilled in the art will appreciate that there are numerous biological markers which can be employed to differentiate between M2-like macrophages and M1-like macrophages. For example, and as described herein, a diminished expression of Nos2 will generally be understood to correlate with M2-like macrophages as compared with higher expression being generally found in M1-like macrophages. Further, and as detailed in experiments herein, the expression of CD206 is generally understood as correlating with M2-like macrophages (see, for e.g., Choi et al. (2010) *Gastroenterology* 138(7) 2399-409). Further, and as detailed in experiments herein, the expression of F4/80 is generally understood to correlate with M2-like macrophages. Further, and for example, M2-like macrophages are generally understood to be effectively activated by IL-4 or by IL-13 through IL-4Rα (Biswas and Mantovain, supra).

Further, comparing the characteristic of the immune response may involve comparing a shift in an activation state of macrophages. The shift in the activation state of macrophages may optionally be characterized as a shift from M2-like macrophages to M1-like macrophages or vice versa. Those persons skilled in the art will appreciate that there are numerous biological markers that can be employed to monitor the activation of macrophages. As detailed herein, those skilled in the art will appreciate that defining a macrophage as being activated towards either a M1-like phenotype or a M2-like phenotype can be accomplished by choosing markers that are known to associate with either of the respective phenotypes described herein.

Optionally, comparing the characteristic of the immune response may involve identifying, in the quantifiable and reference immune samples, cellular markers on any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. A person skilled in the art will appreciate that there are numerous cell markers (both extracellular and intracellular) that can be selected which can identify an immune response. For example, as described herein, the marker CD206 is generally understood as correlating with M2-like macrophages (see, for e.g., Choi et al. (2010) *Gastroenterology* 138(7) 2399-409).

Optionally, comparing the characteristic of the immune response may involve identifying, in the quantifiable and reference immune samples, cytokines produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Those persons skilled in the art will appreciate that cytokines refer to small cell-signalling protein molecules and that there are numerous cytokines known in the art. For example, cytokines have been grouped into type 1 and type 2 classifications based on their role in immunological responses. Common type 1 cytokines include IFN-γ and TGF-β. Common type 2 cytokines include, but are not limited to IL-4 and IL-13. Cytokines can be detected by numerous methodologies known to those persons skilled in the art. For example, and as detailed herein, ELISA experiments were utilized to determine cytokine production from lung tissue.

As detailed herein, the macrophages may include any one or more of the following: M1-like macrophages or M2-like macrophages as has been defined herein. Optionally, the cytokines are produced as a result of a shift in an activation state of the macrophages. Optionally, the macrophages shift from being M2-like macrophages to being M1-like macrophages. Further and optionally, the macrophages shift from being M1-like macrophages to being M2-like macrophages.

Optionally, comparing the characteristic of the immune response may involve identifying, in the quantifiable and reference immune samples, differential gene expression produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. The term "differential gene expression" is understood to mean an appreciable difference between the expression of a particular gene of interest from at least two experimental conditions. For example, if under a first experimental condition a particular gene has a defined expression level as defined by gene expression methods used by those persons skilled in the art and if under a second experimental condition the same gene has an appreciable difference in its expression level, then there is differential expression of the gene of interest. Those persons skilled in the art will understand that there are numerous methodologies with which to detect differential gene expression. For example, commercially available quantitative PCR techniques can be used as detailed herein with respect to determining the relative Nos2/Arg1 ratios. Optionally, the differential gene expression is produced as a result of a shift in an activation state of the macrophages. Optionally, macrophages may shift from being M2-like macrophages to being M1-like macrophages as those terms have been defined herein.

In another embodiment, the medicament may be administered at an administration site in successive doses given at a dosage interval of between one hour and one month, over a dosage duration of at least one week. Optionally, the medicament may be administered intradermally or subcutaneously. Optionally, the medicament may be administered in a dose so that each dose is effective to cause a visible localized inflammatory immune response at the administration site. Optionally, the medicament may be administered so that visible localized inflammation at the administration site occurs within 1 to 48 hours. However, a visible localized inflammatory immune response may not always be present in all circumstances despite an immune response being initiated. Those skilled in the art will appreciate that there are other methods by which the mounting of an immune response can be monitored. For example, the profile (and relative change in characterization) of immune cells from a subject undergoing an immune reaction can be compared with those from a subject that is not undergoing an immune reaction.

Further and optionally with respect to the methods disclosed herein, the animal may be a vertebrate, such as a mammal. Optionally, the animal may be a human or a mouse.

In another aspect, a method of selecting a therapeutic preparation suitable for treating an individual for an infection in a specific organ or tissue is provided. The method involves providing an animal having an infection situated in a specific organ or tissue, providing a test preparation having one or more antigenic determinants of a microbial pathogen which is pathogenic in the corresponding specific organ or tissue in a healthy individual, measuring a characteristic of the immune response in a reference immune sample obtained from the organ or tissue of the animal, administering the test preparation to the animal, measuring a characteristic of the immune response in a quantifiable immune sample obtained from a corresponding organ or tissue of the animal, comparing the characteristic of the immune response in the in the reference and quantifiable immune samples, and treating an enhanced characteristic of the immune response in the quantifiable immune sample compared to the reference immune sample as an indication of the suitability of the test preparation as a therapeutic preparation. Optionally, the animal is sacrificed before the quantifiable immune sample has been obtained.

Optionally, comparing the characteristic of the immune response may involve comparing, in the quantifiable and reference immune samples, an indication of the numbers of any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages as those terms have been defined herein. Optionally, comparing the characteristic of the immune response may involve comparing a shift in an activation state of macrophages. Optionally, the macrophages may shift from being M2-like macrophages to being M1-like macrophages. Further and optionally, the macrophages may shift from being M1-like macrophages to being M2-like macrophages.

Optionally, comparing the characteristic of the immune response may involve identifying, in the quantifiable and reference immune samples, cellular markers on any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages as those terms have been defined herein.

Optionally, comparing the characteristic of the immune response may involve identifying, in the quantifiable and reference immune samples, cytokines produced by any one or more of the following cells: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages as those terms have been defined herein. Optionally, the cytokines are produced as a result of a shift in an activate state of the macrophages. Optionally, the macrophages may shift from being M2-like macrophages to being M1-like macrophages.

Further and optionally, comparing the characteristic of the immune response may involve identifying, in the quantifiable and reference immune samples, differential gene expression produced by any one or more of the following cells: inflammatory monocytes, macrophages, CD11b+

Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages as those terms have been defined herein. Optionally, the differential gene expression may be produced as a result of a shift in an activation state of the macrophages. Optionally, the macrophages may shift from being M2-like macrophages to being M1-like macrophages. Further and optionally, the macrophages may shift from being M1-like macrophages to being M2-like macrophages.

In another aspect, a method of selectively targeting an immune response to an infected tissue or an organ in a human subject is provided. The method involves administering to the subject a medicament having an effective amount of a microbial pathogen antigenic composition, wherein the microbial pathogen may be pathogenic in the specific infected organ or tissue of the subject and the antigenic composition comprises antigenic determinants that together are specific for the microbial pathogen. Optionally, the antigenic composition may include a whole killed bacterial cell composition. Optionally, the medicament may be administered to the subject in an amount and for a time that is effective to up-regulate an immune response in the infected organ or tissue of the subject. Optionally, the method may further involve measuring a characteristic of the immune response.

In another aspect, a method for treating a human subject for an infection situated in a tissue or an organ is provided. The method involves administering to the subject a medicament having an effective amount of a microbial pathogen antigenic composition comprising a whole killed bacterial cell composition, wherein the microbial pathogen is pathogenic in the specific organ or tissue of the subject within which the infection is situated. The medicament may be administered to the subject in an amount and for a time that is effective to modulate an immune response. Optionally, the modulation of the immune response may involve a shift in the activation state of macrophages. Optionally, the modulation of the immune response may involve shifting from a M2-like macrophage response to a M1-like macrophage response. The modulation of the immune responses may involve shifting from a M1-like macrophage response to a M2-like macrophage response. Optionally, the method may further involve measuring a characteristic of the immune response.

Optionally, comparing the characteristic of the immune response may involve comparing, in the quantifiable and reference immune samples, an indication of the numbers of any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages as those terms have been defined herein. Optionally, comparing the characteristic of the immune response may involve comparing a shift in an activation state of macrophages. Further and optionally, the macrophages may shift from being M2-like macrophages to being M1-like macrophages. Optionally, the macrophages may shift from being M1-like macrophages to being M2-like macrophages.

Further and optionally, comparing the characteristic of the immune response may involve identifying, in the quantifiable and reference immune samples, cellular markers on any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages as those terms have been defined herein. Optionally, comparing the characteristic of the immune response may involve identifying, in the quantifiable and reference immune samples, cytokines produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages. Further, cytokines may be produced as a result of a shift in an activation state of the macrophages. The macrophages may shift from being M2-like macrophages to being M1-like macrophages. Optionally, the macrophages may shift from being M1-like macrophages to being M2-like macrophages.

Further and optionally, comparing the characteristic of the immune response may involve identifying, in the quantifiable and reference immune samples, differential gene expression produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, the differential gene expression may be produced as a result of a shift in an activation state of the macrophages. Further and optionally, the macrophages may shift from being M2-like macrophages to being M1-like macrophages. The macrophages may shift from being M1-like macrophages to being M2-like macrophages.

In another aspect, a method of monitoring efficacy of a treatment regime in an individual being treated for an infection in a specific organ or tissue is provided. The method involves measuring a characteristic of an immune response in a post-treatment immune sample obtained from the specific organ or tissue after the individual has been subject to the treatment regime for a period of time, wherein the presence of a characteristic of the immune response which is greater in magnitude than would be expected had the individual not been subject to the treatment regime, is indicative of the efficacy of the treatment regime; and the treatment regime involves administering a preparation comprising one or more antigenic determinants of a microbial pathogen which is pathogenic in the corresponding specific organ or tissue in a healthy subject.

The method detailed herein may further involve measuring the characteristic of the immune response in a pre-treatment reference sample, wherein the pre-treatment reference sample was obtained from the specific organ or tissue before, at the same time as or after commencement of the treatment regime, but prior to obtaining the post-treatment immune sample, and comparing the characteristic of the immune response in the pre-treatment and post-treatment samples, wherein an increase in the magnitude of the immune response in the post-treatment immune sample compared to the pre-treatment reference sample is indicative of the efficacy of the treatment regime. Optionally, measuring the characteristic of the immune response may involve determining an indication of the number of inflammatory monocytes in a sample of the organ or tissue. Optionally, measuring the characteristic of the immune response may involve determining an indication of the number of macrophages in a sample of the organ or tissue. The macrophages may include any one or more of the following: M1-like macrophages or M2-like macrophages.

Optionally, measuring the characteristic of the immune response may involve determining an indication of the number of CD11b+ Gr-1+ cells in a sample of the organ or tissue or determining an indication of the number of dendritic cells in a sample of the organ or tissue. Further and optionally, measuring the characteristic of the immune response may involve determining an indication of the number of CD11c+ MHC class II+ cells in a sample of the organ or tissue or determining an indication of the number of CD4+ T cells in a sample of the organ or tissue or determining an indication of the number of CD8+ T cells in a sample of the organ or tissue.

Optionally, measuring the magnitude of the immune response may involve determining an indication of the number of NK cells in a sample of the organ or tissue. Further and optionally, comparing the characteristic of the immune response may involve identifying, in the reference and immune samples, cellular markers on any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. Optionally, the macrophages may include any one or more of the following: M1-like macrophages or M2-like macrophages.

Further and optionally, comparing the characteristic of the immune response may involve identifying, in the reference and immune samples, cytokines produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. Optionally, the cytokines may be produced as a result of a shift in an activation state of the macrophages. The macrophages may shift from being M2-like macrophages to being M1-like macrophages. Further and optionally, the macrophages may shift from being M1-like macrophages to being M2-like macrophages.

Optionally, comparing the characteristic of the immune response may involve identifying, in the reference and immune samples, differential gene expression produced by any one or more of the following cells as they are commonly understood to those persons skilled in the art: inflammatory monocytes, macrophages, CD11b+ Gr-1+ cells, dendritic cells, CD11c+ MHC class II+ cells, CD4+ T cells, CD8+ T cells, or NK cells. The macrophages may include any one or more of the following: M1-like macrophages or M2-like macrophages. The differential gene expression may be produced as a result of a shift in an activation state of the macrophages. The macrophages may shift from being M2-like macrophages to being M1-like macrophages. Optionally, the macrophages may shift from being M1-like macrophages to being M2-like macrophages.

The viral pathogen utilized herein may be, without limitation: influenza, adenovirus, respiratory syncytial virus, parainfluenza, monkeypox, herpes simplex virus (1 and 2), Varicella zoster, cytomegalovirus, Epstein-Barr virus, coronavirus, human metapneumovirus, Hendra virus, Nipah virus, Hantavirus, Lassa virus, human T-cell lymphotrophic virus, cocksackievirus, echovirus, enterovirus, or rhinovirus, or any virus that is pathogenic in the lung.

The bacterial pathogen utilized herein may be, without limitation: *Streptococcus pneumoniae, Moraxella catarrhalis, Mycoplasma pneumoniae, Klebsiella pneumoniae, Haemophilus influenza, Staphylococcus aureus, Chlamydia pneumoniae, Legionella pneumophila,* or *Bordatella pertussis* or any bacterium that is pathogenic in the lung.

The fungal pathogen utilized herein may be, without limitation: *Aspergillus fumigatus, Blastomyces* sp., *Coccidiodes immitis, Coccidiodes posadasii, Cryptococcus neoformans, Cryptococcus gattii, Fusarium* sp., *Histoplasma capsulatum, Paecilomyces* sp., *Paracoccidioides brasiliensis, Penicillium mameffei, Pneumocystis jiroveci, Pseudallescheria boydii, Scedosporium apiospermum, Rhizopus* sp., *Mucor* sp., *Absidia* sp., *Cunninghamella* sp., *Scedosporium prolificans, Stachybotrys chartarum, Trichoderma longibrachiatium, Trichosporon* sp., or any fungus that is pathogenic in the lung.

In various aspects, embodiments of the invention relate to compositions comprising components of organisms that may cause infections of the gastrointestinal tract, so that the organism may be characterized as a pathogen. However, an organism that is in some cases pathogenic may not always cause disease. Most animals are colonized to some degree by other organisms, such as bacteria, which generally exist in symbiotic or commensal relationships with the host animal. Thus, many species of normally harmless bacteria are found in healthy animals, and are usually localized to the surface of specific organs and tissues. Often, these bacteria aid in the normal functioning of the body. For example, in humans, symbiotic *Escherichia coli* bacteria may be found in the intestine, where they promote immunity and reduce the risk of infection with more virulent pathogens.

Bacteria that are generally harmless, such as *Escherichia coli*, can cause infection in healthy subjects, with results ranging from mild to severe infection to death. Whether or not an organism, such as a bacterium, is pathogenic (i.e., causes infection) depends to some extent on factors such as the route of entry and access to specific host cells, tissues, or organs; the intrinsic virulence of the bacterium; the amount of the bacteria present at the site of potential infection; or the health of the host animal. Thus, organisms that are normally harmless can become pathogenic given favorable conditions for infection, and even virulent organisms may require specific circumstances to cause infection. Accordingly, organisms that are members of the normal flora can be pathogens when they move beyond their normal ecological role in the endogenous flora. For example, endogenous species can cause infection outside of their ecological niche in regions of anatomical proximity, for example by contiguous spread. When this occurs, and in the context of the present invention, these normally harmless endogenous organisms are considered pathogenic.

Specific organisms, such as bacterial species, viruses, worms, and protozoa are known to cause infections in specific regions of the GIT in otherwise healthy subjects. Examples of organisms that commonly cause infections in specific regions of the GIT are listed below; it will be understood that these examples are not intended to be limiting and that a skilled person would be able to readily recognize and identify infectious or pathogenic organisms that cause infections, or commonly cause infections, in various regions of the GIT in healthy adults, based for example on knowledge about particular patient populations, as represented for example by the following publications: Manual of Clinical Microbiology 8th Edition, Patrick Murray, Ed., 2003, ASM Press American Society for Microbiology, Washington D.C., USA; Mandell, Douglas, and Bennett's Principles and Practice of Infectious Diseases 5th Edition, G. L. Mandell, J. E. Bennett, R. Dolin, Eds., 2000, Churchill Livingstone, Philadelphia, Pa., USA, all of which are incorporated by reference herein.

Infections of the mouth are commonly caused by the following bacterial species: *Prevotella melaninogenicus*, anaerobic streptococci, viridans streptococci, *Actinomyces* spp., *Peptostreptococcus* spp., or *Bacteroides* spp., or other oral anaerobes; or viral pathogens: herpes simplex, coxsackieviruses, or Epstein-Barr.

Infections of the esophagus are commonly caused by the following bacterial species: *Actinomyces* spp., *Mycobacterium avium, Mycobacterium tuberculosis*, or *Streptococcus* spp.; or viral pathogens: cytomegalovirus, herpes simplex, or varicella-zoster.

Infections of the stomach are commonly caused by the following bacterial species: *Streptococcus pyogenes* or *Helicobacter pylori*; or viral pathogens: cytomegalovirus, herpes simplex, Epstein-Barr, rotaviruses, noroviruses, or adenoviruses.

Infections of the small bowel are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the colon/rectum are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the anus are commonly caused by the following bacterial species: *Streptococcus pyogenes, Bacteroides* spp., *Fusobacterium* spp., anaerobic streptococci, *Clostridium* spp., *Escherichia coli, Enterobacter* spp., *Pseudomonas aeruginosa*, or *Treponema pallidum*; or viral pathogens: herpes simplex.

Organisms such as bacteria are often classified operationally as collections of similar strains (which generally refer to groups of presumed common ancestry with identifiable physiological but usually not morphological distinctions, and which may be identified using serological techniques against bacterial surface antigens). Thus, each bacterial species (e.g., *Escherichia coli*) has numerous strains (or serotypes), which may differ in their ability to cause infection or differ in their ability to cause infection in a particular organ/site. Certain strains of *Escherichia coli* are more likely to cause gastrointestinal infection/diarrhea, including enterotoxigenic *E. coli* (ETEC), enteropathogenic *E. coli* (EPEC), enterohemorrhagic *E. coli* (EHEC), Shiga toxin-producing *E. coli* (STEC), enteroaggregative *E. coli* (EAEC), enteroinvasive *E. coli* (EIEC) and diffuse adhering *E. coli* (DAEC). In accordance with the present invention, one or more of an ETEC, EPEC, EHEC, STEC, EAEC, EIEC or DAEC strains of *E. coli* (i.e., strains that cause colon infection), may be chosen for a formulation to treat a heterologous microbial infection, such as an infection of the GIT, for example an IBD-related microbial infection. For example, a non-ETEC strain of *E. coli* may be used to prepare an antigenic formulation for treating an infection by an ETEC strain of *E. coli*. Similarly, non-EPEC, non-EHEC, non-STEC, non-EAEC, non-EIEC or non-DAEC strains of *E. coli* may be used to formulate an antigenic formulation for treating an infection by, respectively, an EPEC, EHEC, STEC, EAEC, EIEC or DAEC strain of *E. coli*.

Similarly, there may be numerous subtypes of specific viruses, worms, or protozoa, which are associated with disease in a particular population, and are therefore amenable for use in the present invention.

The compositions of the invention include antigens of organisms that are pathogenic in a specific region of the body, such as the GIT. The compositions may include the components of whole organisms, whole cells or whole virions, or may include extracts or preparations of the organisms, such as cell wall or cell membrane extracts, or exotoxins. The compositions may also include one or more isolated antigens from these organisms. Pathogenic organisms may be available commercially (for example from the American Type Culture Collection, Manassas, Va., USA), or may be clinical isolates from subjects having an infection.

The compositions of the invention derived from pathogens can be provided alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans. As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration, including subcutaneous, intradermal, intravenous, parenteral, intraperitoneal, intramuscular, sublingual, inhalational, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound (i.e., the specific bacteria, bacterial antigens, or compositions thereof of the invention), use thereof in the pharmaceutical compositions of the invention is contemplated. Supplementary active compounds can also be incorporated into the compositions.

Methods well known in the art for making formulations are found in, for example, "Remington's Pharmaceutical Sciences" (20th edition), ed. A. Gennaro, 2000, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the formulations may be administered to an individual in an amount effective to prevent, stop or slow progression of a microbial infection.

An "effective amount" of a pathogenic species or antigen thereof according to the invention includes a therapeutically effective amount or a prophylactically effective amount. A "therapeutically effective amount" refers to an amount effective, at dosages and for periods of time necessary, to achieve the desired therapeutic result, such as reduction or elimination of symptoms of a microbial infection. A therapeutically effective amount of a pathogenic species or antigen(s) thereof may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the pathogenic species or antigen thereof are outweighed by the therapeutically beneficial effects. A "prophylactically effective amount" refers to an amount effective, at dosages and for periods of time necessary, to achieve the desired prophylactic result, such as prevention of a microbial infection. Typically, a prophylactic dose is used in subjects prior to or at an earlier stage of a microbial infection, so that a prophylactically effective amount may be less than a therapeutically effective amount.

For administration by subcutaneous or intradermal injection, an exemplary range for therapeutically or prophylactically effective amounts of one or more pathogenic bacterial species may be about 1 million to 100,000 million organisms per ml, or may be 100 million to 7000 million organisms per ml, or may be 500 million to 6000 million organisms per ml, or may be 1000 million to 5000 million organisms per ml, or may be 2000 million to 4000 million organisms per ml, or any integer within these ranges. The total concentration of bacteria per ml may range from 1 million to 100,000 million organisms per ml, or may be 50 million to 7000 million organisms per ml, or may be 100 million to 6000 million organisms per ml, or may be 500 million to 5000 million organisms per ml, or may be 1000 million to 4000 million organisms per ml, or any integer within these ranges. The range for therapeutically or prophylactically effective amounts of antigens of a pathogenic bacterial species may be any integer from 0.1 nM-0.1 M, 0.1 nM-0.05M, 0.05 nM-15 µM or 0.01 nM-10 µM.

It is to be noted that dosage concentrations and ranges may vary with the severity of the condition to be alleviated, or may vary with the subject's immune response. In general, the goal is to achieve an adequate immune response. For administration by subcutaneous or intradermal infection, the extent of an immune response may be determined, for example, by size of delayed local immune skin reaction at the site of injection (e.g., from 0.25 inch to 4 inch diameter). The dose required to achieve an appropriate immune response may vary depending on the individual (and their immune system) and the response desired. Standardized dosages may also be used.

In the context of subcutaneous or intradermal administration, if the goal is to achieve a 2 inch local skin reaction, using a bacterial composition, the total dose may, for example, range from 2 million bacteria (e.g., 0.001 ml of a composition with a concentration of 2,000 million organisms per ml) to more than 20,000 million bacteria (e.g., 1 ml of an antigenic composition with a concentration of 20,000 million organisms per ml). The concentrations of individual bacterial species or antigens thereof within a composition may also be considered. For example, if the concentration of one particular pathogenic bacterial species, cell size of that species or antigenic load thereof is much higher relative to the other pathogenic bacterial species in the antigenic composition, then the local immune skin reaction of an individual may be likely due to its response to this specific bacterial species. In some embodiments, the immune system of an individual may respond more strongly to one bacterial species within a composition than another, depending for example on past history of exposure to infection by a particular species, so the dosage or composition may be adjusted accordingly for that individual.

For any particular subject, the timing and dose of treatments may be adjusted over time (e.g., timing may be daily, every other day, weekly, monthly) according to the individual need and the professional judgement of the person administering or supervising the administration of the compositions. For example, in the context of subcutaneous or intradermal administration, the compositions may be administered every second day. An initial dose of approximately 0.05 ml may be administered subcutaneously, followed by increases from 0.01-0.02 ml every second day until an adequate skin reaction is achieved at the injection site (for example, a 1 inch to 2 inch diameter delayed reaction of visible redness at the injection site). Once this adequate immune reaction is achieved, this dosing is continued as a maintenance dose. The maintenance dose may be adjusted from time to time to achieve the desired visible skin reaction (inflammation) at the injection site. Dosing may be for a dosage duration, for example of at least 2 weeks, 2 months, 6 months, 1, 2, 3, 4, or 5 years or longer.

In some embodiments, the invention may include antigenic compositions administered to one or more epithelial tissues by a non-enteric route. For example: to skin by intradermal or subcutaneous injection; to lung epithelium by inhalation. Accordingly, in some embodiments the antigenic compositions of the invention are administered so as to provoke an immune response in a non-enteric tissue, such as an epithelial tissue. In some embodiments, one or more non-enteric routes of administration may be combined with one or more additional routes of administration, such as intramuscular or intravenous administration.

In various aspects of the invention, the antigenic compositions that are administered to a patient may be characterized as having an antigenic signature, i.e., a combination of antigens or epitopes that is sufficiently specific that the antigenic composition is capable of eliciting an immune response that is specific to a particular pathogen, such as an adaptive immune response.

The amount of active compound (e.g., bacterial species, viruses, protozoa or helminths, or antigens thereof) in compositions of the invention may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of antigenic formulations, an immunogenically effective amount of a compound of the invention can be provided, alone or in combination with other compounds, with an immunological adjuvant. The compound may also be linked with a carrier molecule, such as bovine serum albumin or keyhole limpet hemocyanin to enhance immunogenicity. An antigenic composition is a composition that includes materials that elicit a desired immune response. An antigenic composition may select, activate or expand memory B, T cells, neutrophils, monocytes or macrophages of the immune system to, for example, reduce or eliminate the symptoms of the microbial infection. In some embodiments, the specific pathogenic microbe, virus, viral antigens, bacteria, bacterial antigens, or compositions thereof of the invention are capable of eliciting the desired immune response in the absence of any other agent, and may therefore be considered to be an antigenic composition. In some embodiments, an antigenic composition includes a suitable carrier, such as an adjuvant, which is an agent that acts in a non-specific manner to increase the immune response to a specific antigen, or to a group of antigens, enabling the reduction of the quantity of antigen in any given dose, or the reduction of the frequency of dosage required to generate the desired immune response. A bacterial antigenic composition may include live or dead bacteria capable of inducing an immune response against antigenic determinants normally associated with the bacteria. In some embodiments, an antigenic composition may include live bacteria that are of less virulent strains (attenuated), and therefore cause a less severe infection. In some embodiments the antigenic composition may include live, attenuated or dead viruses capable of inducing an immune response against antigenic determinants normally associated with the virus.

An antigenic composition comprising killed organisms for administration by injection may be made as follows. The organism may be grown in suitable media, and washed with physiological salt solution. The organism may then be centrifuged, resuspended in saline solution, and killed with heat. The suspensions may be standardized by direct microscopic count, mixed in required amounts, and stored in appropriate containers, which may be tested for safety, shelf life, and sterility in an approved manner. In addition to the organism and/or antigens thereof, a killed preparation suitable for administration to humans may include phenol preservative (for example 0.4%) and/or sodium chloride (for example on the order of 0.9%). The composition may also for example include trace amounts of brain heart infusion (beef), peptones, yeast extract, agar, sheep blood, dextrose, sodium phosphate and/or other media components.

In some embodiments, the antigenic composition may be used as an aerosol for inhalation.

In general, the compositions of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population).

In some embodiments, bacteria that are members of the endogenous flora of a particular region of the GIT may be used to formulate antigenic compositions of the invention. The rows of Table 1 list a number of bacterial species, together with the biological regions in which each species may form a part of the endogenous flora. For example, *Abiotrophia* spp. are typically members of the endogenous flora of the mouth.

TABLE 1

Human Bacterial Normal Flora
(Endogenous Bacterial Human Pathogens)

| Bacterial species | Mouth | Stomach | Duodenum/Jejunum | Ileum | Colon |
|---|---|---|---|---|---|
| CFU/mL | $10^5$ | $10^2$ | $10^5$ | $10^8$ | $10^{11}$ |
| *Abiotrophia* spp | + | | | | |
| *Acholeplasma laidlawii* | + | | | | |

TABLE 1-continued

Human Bacterial Normal Flora
(Endogenous Bacterial Human Pathogens)

| Bacterial species | Mouth | Stomach | Duodenum/Jejunum | Ileum | Colon |
|---|---|---|---|---|---|
| *Acidaminococcus fermentans* | + | | + | + | + |
| *Acinetobacter* spp. | + | | + | + | + |
| *Actinobacillus* spp. | + | | | | |
| *Actinobaculum* spp. | + | | + | + | + |
| *Actinomyces* spp. | + | | + | + | + |
| *Aeromonas* spp. | | | + | + | + |
| *Anaerorhabdus furcosus* | | | | + | + |
| *Anaerococcus hydrogenalis* | | | | + | + |
| *Anaerococcus lactolyticus* | | | | + | + |
| *Anaerococcus prevotii* | | | | + | + |
| *Atopobium* spp. | + | | + | + | + |
| *Bacillus* spp. | | | | + | + |
| *Bacteroides caccae* | | | | + | + |
| *Bacteroides distasonis* | | | | + | + |
| *Bacteroides eggerthii* | | | | + | + |
| *Bacteroides fragilis* | | | | + | + |
| *Bacteroides merdae* | | | | + | + |
| *Bacteroides ovatus* | | | | + | + |
| *Bacteroides splanchnicus* | | | | + | + |
| *Bacteroides thetaiotaomicron* | | | | + | + |
| *Bacteroides vulgatus* | | | | + | + |
| *Bifidobacterium adolescentis* | | | + | + | + |
| *Bifidobacterium bifidum* | | | + | + | + |
| *Bifidobacterium breve* | | | + | + | + |
| *Bifidobacterium catenulatum* | | | + | + | + |
| *Bifidobacterium dentium* | + | | + | + | + |
| *Bifidobacterium longum* | | | + | + | + |
| *Bilophila wadsworthia* | + | | + | + | + |
| *Burkholderia cepacia* | | | + | + | + |
| *Butyrivibrio fibrisolvens* | | | + | + | + |
| *Campylobacter concisus* | | | + | + | + |
| *Campylobacter curvus* | | | + | + | + |
| *Campylobacter gracilis* | | | + | + | + |
| *Campylobacter jejuni* | | | + | + | + |
| *Campylobacter rectus* | | | + | + | + |
| *Campylobacter showae* | + | | + | + | + |
| *Campylobacter sputorum* | + | | | | |
| *Capnocytophaga granulosum* | + | | | | |
| *Capnocytophaga gingivalis* | + | | | | |
| *Campylobacter haemolytica* | + | | | | |
| *Capnocytophaga ochracea* | + | | + | + | + |
| *Capnocytophaga sputigena* | + | | | | |

TABLE 1-continued

Human Bacterial Normal Flora
(Endogenous Bacterial Human Pathogens)

| Bacterial species | Mouth | Stomach | Duodenum/Jejunum | Ileum | Colon |
|---|---|---|---|---|---|
| Cardiobacterium hominis | + | | | | |
| Cedecea spp | | | | | + |
| Centipeda periodontii | + | | | | |
| Citrobacter freundii | | | + | + | + |
| Citrobacter koseri | | | + | + | + |
| Clostridium spp. | | | + | + | + |
| Corynebacterium accolens | + | | | | |
| Corynebacterium afermentans | + | | | | |
| Desulfomonas pigra | | | + | + | + |
| Dysgonomonas spp. | | | + | + | + |
| Eikenella corrodens | + | | + | + | + |
| Enterobacter aerogenes | | | + | + | + |
| Enterobacter cloacae | | | + | + | + |
| Enterobacter gergoviae | | | + | + | + |
| Enterobacter sakazakii | | | + | + | + |
| Enterobacter taylorae | | | + | + | + |
| Enterococcus spp. | | | + | + | + |
| Escherichia coli | | | + | + | + |
| Escherichia fergusonii | | | + | + | + |
| Escherichia hermannii | | | + | + | + |
| Escherichia vulneris | | | + | + | + |
| Eubacterium spp. | + | | + | + | + |
| Ewingella americana | + | | | | |
| Finegoldia magnus | | | + | + | + |
| Fusobacterium alocis | + | | | | |
| Fusobacterium gonidiaformans | | | + | + | + |
| Fusobacterium mortiferum | | | + | + | + |
| Fusobacterium naviforme | | | + | + | + |
| Fusobacterium necrophorum | + | | + | + | + |
| Fusobacterium nucleatum | + | | | | + |
| Fusobacterium sulci | + | | | | |
| Fusobacterium russii | | | + | + | + |
| Fusobacterium varium | | | + | + | + |
| Gardnerella vaginalis | | | + | + | + |
| Gemella haemolysans | + | | | | |
| Gemella morbillorum | + | | + | + | + |
| Globicatella spp. | + | | | | + |
| Granulicatella spp. | + | | | | |
| Haemophilus spp. | + | | | | |
| Hafnia alvei | | | + | + | + |
| Helcococcus kunzii | + | | | | |
| Helicobacter spp. | | + | + | + | + |
| Kingella spp. | + | | | | |
| Klebsiella spp. | | | + | + | + |
| Lactobacillus acidophilus | + | + | + | + | + |
| Lactobacillus breve | + | | | | |
| Lactobacillus casei | + | | | | |
| Lactobacillus fermentum | + | + | + | + | + |
| Lactobacillus reuteri | | + | + | + | + |
| Lactobacillus salivarius | + | + | + | + | + |
| Leclercia adecarboxylata | | | + | + | |
| Leminorella spp. | | | + | + | + |
| Leptotrichia buccalis | + | | | | |
| Megasphaera elsdenii | | | + | + | + |
| Micrococcus luteus | + | | | | |
| Micrococcus lylae | + | | | | |
| Micromonas micros | + | | | | |
| Mitsuokella multiacidus | | | + | + | + |
| Mobiluncus curisii | | | + | + | + |
| Mobiluncus mulieris | | | + | + | + |
| Moellerella wisconsensis | | | + | + | + |
| Moraxella catarrhalis | + | | | | |
| other Moraxella spp. | + | | | | |
| Morganella morganii | | | + | + | + |
| Mycoplasma buccale | + | | | | |
| Mycoplasma fermentans | + | | | | |
| Mycoplasma hominis | + | | | | |
| Mycoplasma lipophilum | + | | | | |
| Mycoplasma orale | + | | | | |
| Mycoplasma pneumoniae | + | | | | |
| Mycoplasma salivarium | + | | | | |
| Pantoea agglomerans | | | + | + | + |
| Pasteurella multocida | + | | | | |
| Pediococcus spp. | + | | | | + |
| Peptoniphilus asaccharolyticus | | | + | + | + |
| Peptostreptococcus anaerobus | + | | + | + | + |
| Peptostreptococcus productus | | | + | + | + |
| Porphyromonas asaccharolytica | + | | + | | + |
| Porphyromonas catoniae | + | | + | | |
| Porphyromonas endodontalis | + | | + | | |
| Porphyromonas gingivalis | + | | + | | |
| Prevotella buccae | + | | + | | |
| Prevotella buccalis | + | | + | | |
| Prevotella corporis | + | | + | | |
| Prevotella dentalis | + | | + | | |
| Prevotella denticola | + | | + | | |
| Prevotella enoeca | + | | + | | |
| Prevotella heparinolytica | + | | + | | |
| Prevotella intermedia | + | | + | | |
| Prevotella loescheii | + | | + | | |
| Prevotella melaninogenica | + | | + | | |

TABLE 1-continued

Human Bacterial Normal Flora
(Endogenous Bacterial Human Pathogens)

| Bacterial species | Mouth | Stomach | Duodenum/Jejunum | Ileum | Colon |
|---|---|---|---|---|---|
| Prevotella nigrescens | + | | + | | |
| Prevotella oralis | + | | + | | |
| Prevotella oris | + | | + | | |
| Prevotella oulorum | + | | + | | |
| Prevotella tannerae | + | | + | | |
| Prevotella veroralis | + | | + | | |
| Prevotella zoogleoformans | + | | + | | |
| Propionibacterium propionicum | + | | | | |
| Proteus mirabilis | | | | + | + |
| Proteus penneri | | | | + | + |
| Proteus vulgaris | | | | + | + |
| Providencia rettgeri | | | | + | + |
| Providencia stuartii | | | + | + | + |
| Pseudomonas aeruginosa | | | + | + | + |
| Retortamonas intestinalis | | | + | + | + |
| Rothia dentocariosa | + | | | | |
| Rothia mucilaginosa | + | | | | |
| Ruminococcus productus | | | + | + | + |
| Selenomonas spp. | + | | | | |
| Serratia liquefaciens | | | | + | + |
| Serratia marcescens | | | | + | + |
| Serratia odorifera | | | | + | + |
| Staphylococcus aureus | + | | | | |
| Staphylococcus epidermidis | + | | | | |
| Streptococcus agalactiae | | | + | + | + |
| Streptococcus anginosus | + | | + | + | + |
| Streptococcus bovis | | | + | + | + |
| Streptococcus constellatus | + | | + | + | + |
| Streptococcus criceti | + | | | | |
| Streptococcus crista | + | | | | |
| Streptococcus equisimilis | + | | | | |
| Streptococcus gordonii | + | | | | |
| Streptococcus intermedius | + | | | + | + |
| Streptococcus mitis | + | + | | | |
| Streptococcus mutans | + | | | | |
| Streptococcus oralis | + | | | | |
| Streptococcus parasanguis | + | | | | |
| Streptococcus pyogenes | + | + | | | |
| Streptococcus salivarius | + | + | | | |
| Streptococcus sanguis | + | + | | | |
| Streptococcus sobrinus | + | | | | |
| Streptococcus vestibularis | + | | | | |
| Group C + G Streptococci | + | | | | + |
| Succinivibrio dextrinosolvens | | | + | + | + |
| Sutterella spp. | + | | | + | + |
| Suttonella indologenes | + | | | | |
| Tissierella praeacuta | | | + | + | + |
| Treponema denticola | + | | | | |
| Treponema maltophilum | + | | | | |
| Treponema socranskii | + | | | | |
| Treponema vincentii | + | | | | |
| Ureaplasma urealyticum | + | | | | |
| Veillonella spp. | + | | + | + | + |

Endogenous microbial flora, such as bacteria, have access to tissues for pathogenesis either through contiguous spread or bacteremic spread. Under favorable conditions, all endogenous organisms can become pathogenic and invade locally and spread by contiguous spread to adjacent tissues and organs. Endogenous bacterial flora of the skin, mouth and colon are the species that are understood to also be amenable to bacteremic spread. Bacteria that are members of a particular endogenous flora domain may therefore cause infection in tissues or organs to which these bacteria may spread. Accordingly, one aspect of the invention involves the use of endogenous microbial pathogens to treat a microbial infection having symptoms localized to a region of the GIT in which the endogenous bacteria may spread to cause infection. The columns of Table 2 list domains for endogenous flora. The rows of Table 2 list regions of the GIT within which a microbial infection may be situated. Accordingly, one aspect of the invention involves the use of endogenous microbial pathogens to formulate antigenic compositions, or the selection of existing formulations having the pathogens, for treating a microbial infection situated in the region of the GIT to which the pathogen may spread to cause an infection. Accordingly, in alternative embodiments, a microbial infection that is symptomatic in the region listed in the first column of Table 2 may be treated with antigenic compositions comprising antigenic determinants that are specific for microbial pathogens that are members of the endogenous flora of one or more of the endogenous flora domains listed in the first row of Table 2 and indicated with an X or a check mark in the appropriate row.

TABLE 2

Tissue/Organ Pathogenicity of Endogenous Flora

| Tissue/organ site | Mouth | Stomach | Duo-denum/Jejunum | Ileum | Colon |
|---|---|---|---|---|---|
| Oral | × | | | | |
| Tonsil | × | | | | |
| Nasopharynx/Sinus | × | | | | |
| Esophagus | | × | | | |
| Stomach | | × | | | |
| Small bowel | | | × | × | |
| Colon/Rectum | | | | | × |
| Anus | | | | | × |

In accordance with the combined information in Tables 1 and 2, a microbial infection manifest in a particular region of the GIT set out in column 1 of Table 2 may be treated with antigenic compositions comprising antigenic determinants of the corresponding bacterial species of Table 1, so that the column headings in Table 2 are in effect replaced with the bacterial species of Table 1.

In some embodiments, pathogens for use in the invention may be exogenous bacterial pathogens. For example, the organisms listed in Table 3 may be used as microbial pathogens to formulate antigenic compositions, or antigenic compositions having those pathogens may selected, for use to treat a microbial infection situated in the region of the GIT listed with the relevant organism in Table 3. In some embodiments, antigenic determinants of both endogenous and exogenous bacterial species targeted to a specific tissue or organ may be used in combination. For example, an antigenic composition derived from, or specific for, *Clostridium difficile*, may be used to treat a microbial infection situated in the colon.

TABLE 3

Exogenous Bacterial Human Pathogens, and their Sites of Infection in the GIT

| Bacterial Species | Region of the GIT |
|---|---|
| *Aerobacter* spp. | small bowel, colon, |
| *Bacillus anthracis* | oral, small bowel, colon, hematological |
| *Bacillus cereus* | colon, |
| other *Bacillus* spp. | colon, stomach, small bowel |
| *Brucella* spp. | small bowel, colon |
| *Campylobacter coli* | small bowel, colon |
| *Campylobacter jejuni* | colon |
| *Campylobacter sputorum* | small bowel, colon |
| *Clostridium bifermentans* | small bowel, colon, stomach |
| *Clostridium botulinum* | colon, small bowel |
| *Clostridium difficile* | colon |
| *Clostridium indolis* | small bowel, colon, stomach, |
| *Clostridium mangenolii* | small bowel, colon, stomach |
| *Clostridium perfringens* | small bowel, colon, stomach |
| *Clostridium sordellii* | small bowel, colon, stomach |
| *Clostridium sporogenes* | small bowel, colon, stomach |
| *Clostridium subterminale* | small bowel, colon, stomach |
| *Edwarsiella tarda* | small bowel, colon |
| *Francisella tularensis* | small bowel |
| *Helicobacter pylori* | stomach |
| *Leptospirosis* spp. | oral |
| *Listeria monocytogenes* | small bowel, colon |
| *Mycobacterium bovis* | colon, small bowel |
| *Mycobacterium tuberculosis* | small bowel, colon |
| *Pediococcus* spp. | colon |
| *Plesiomonas shigelloides* | small bowel, colon |
| *Rickettsia rickettsiae* | small bowel |
| *Salmonella* spp. | stomach, small bowel, colon |
| *Shigella boydii* | colon |
| *Shigella dysenteriae* | colon |
| *Shigella flexneri* | colon |
| *Shigella sonnei* | colon |
| other *Spirillum* spp. | colon |
| *Streptococcus zooepidemicus* | small bowel |
| *Treponema pallidum* | oral, anus |
| *Tropheryma whipplei* | small bowel, colon |
| *Vibrio cholerae* | colon, small bowel |
| *Vibrio fluvialis* | small bowel, colon |
| *Vibrio furnissii* | small bowel, colon |
| *Vibrio hollisae* | small bowel, colon |
| *Vibrio parahaemolyticus* | colon, small bowel |
| *Yersinia enterocolitica* | small bowel, colon |
| *Yersinia pseudotuberculosis* | small bowel, colon |

In some embodiments, pathogens for use in the invention may be viral pathogens. Table 4 provides an exemplary list of viral pathogens together with the tissue and organ sites for which each viral species is reportedly a pathogen. Accordingly, one aspect of the invention involves utilizing immunogenic compositions that are specific for the named viruses to treat a pathology associated with a heterologous infection situated in the region of the GIT that is identified adjacent to the name of the virus in Table 4.

TABLE 4

Viral Human Pathogens and Their Sites of Infection

| Virus | Region of the GIT |
|---|---|
| Herpes Simplex virus (1 and 2) | rectum, anus |
| Cytomegalovirus | small bowel, colon/rectum |
| Epstein-Barr virus | oral |
| Adenovirus | oral, small bowel, colon |
| Human papillomavirus | anus, oral |
| Orthoreoviruses | small bowel, colon, oral |
| Coltiviruses | oral |
| Rotaviruses | small bowel, colon |
| Alphaviruses | small bowel, colon, |
| Coronaviruses | oral, small bowel, colon |
| Toroviruses | small bowel, colon |
| Parainfluenza viruses | oral |
| Respiratory syncytial virus | oral |
| Human metapneumovirus | oral, small bowel, colon |
| Vesicular stomatitis virus | oral, small bowel, colon |
| Rabies virus | oral |
| Influenza virus | oral |
| Hantaviruses | oral |
| Machupo virus | small bowel, colon |
| Junin virus | small bowel, colon |
| Poliovirus | small bowel, colon |
| Coxsackieviruses | small bowel, colon |
| Echoviruses | oral, small bowel, colon |
| Hepatitis A virus | small bowel, colon |
| Rhinoviruses | oral |
| Noroviruses and other Caliciviruses | small bowel, colon |
| Astroviruses | small bowel, colon |
| Picobirnaviruses | small bowel, colon |
| Hepatitis E virus | small bowel, colon |

The cumulative information in Tables 1 through 4 provides an extensive identification of pathogens that may be used in the formulation of antigenic compositions of the invention, together with an identification of the region of the GIT in which these organisms are pathogenic, and accordingly identifies the region of the GIT in which an infection is situated that may be treated with an antigenic antimicrobial formulation of the invention. Pathogens may be selected from endogenous pathogens or exogenous pathogens.

In some embodiments, the pathogen selected for use in antigenic compositions of the invention may be one that is a common cause of acute infection in the region of the GIT in which the microbial infection to be treated is situated. Table 5 identifies bacterial and viral pathogens of this kind, together with the region of the GIT in which they commonly cause infection. Accordingly, in selected embodiments, a microbial infection, such as an IBD-related infection, residing in a region of the GIT identified in the first column of Table 5 may be treated with an antigenic composition that comprises antigenic determinants for one or more of the pathogenic organisms listed in the second column of Table 5.

TABLE 5

Common causes of acute infection (bacteria and viruses) for selected regions of the GIT

| Selected regions of the GIT | Common Bacterial or Viral Pathogens |
|---|---|
| Oral | *Prevotella melaninogenicus*, anaerobic streptococci, viridans streptococci, *Actinomyces* spp., *Peptostreptococcus* spp., *Bacteroides* spp., and other oral anaerobes |
| | herpes simplex, coxsackie viruses, Epstein-Barr |
| Stomach | *Streptococcus pyogenes*, *Helicobacter pylori* |
| | cytomegalovirus, herpes simplex, Epstein-Barr, rotaviruses, noroviruses, adenoviruses |
| Small bowel | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |
| Colon/Rectum | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |
| Anus | *Streptococcus pyogenes*, *Bacteroides* spp., *Fusobacterium* spp., anaerobic streptococci, *Clostridium* spp., *E. coli*, *Enterobacter* spp., *Pseudomonas aeruginosa*, *Treponema pallidum* |
| | herpes simplex |

The specific organisms which commonly cause infection in a specific region of the GIT may vary by geographical location. Table 5 is thus not an exhaustive list of common pathogens for all geographic locations and population groups. It is understood that a clinical microbiologist skilled in the art could determine the common pathogenic species in a particular geographic area or population group for a specific region of the GIT in accordance with the invention.

Humans are hosts to a wide range of gastrointestinal parasites, including various protozoa and helminths, which for purposes of the present invention constitute pathogens of the GIT (Schafer, T. W., Skopic, A. Parasites of the small intestine. Curr Gastroenterol Reports 2006; 8:312-20; Jernigan, J., Guerrant, R. L., Pearson, R. D. Parasitic infections of the small intestine. Gut 1994; 35:289-93; Sleisenger & Fordtran's Gastrointestinal and liver disease. 8th ed. 2006; Garcia, L. S. Diagnostic medical parasitology. 5th ed. 2007). Compositions of the invention may accordingly include antigenic components of various protozoa, including for example: *Giardia lamblia*, *Cryptosporidium parvum*, *Cryptosporidium hominus*, *Isospora belli*, *Sarcocystis* species, Coccidian like bodies (*Cyclospora* species), *Enterocytozoon bieneusi*, *Entamoeba histolytica*, *Entamoeba dispar*, *Entamoeba coli*, *Entamoeba hartmanni*, *Endolimax nana*, *Iodamoeba bütschlii*, *Dientameoba fragilis*, *Blastocystis hominus*, *Cyclospora cayetanensis*, Microsporidia, *Trypanosoma cruzi*, *Chilomastix mesnili*, *Pentatrichomonas hominis*, *Balantidium coli*. Similarly, compositions of the invention may include antigenic components of various helminths, including for example: Cestodes (tapeworms), *Taenia saginata*, *Taenia solium*, *Diphyllobothrium* species, *Hymenolepis nana*, *Hymenolepis diminuta*, *Dipylidium caninum*, Nematodes (round worms), *Ascaris lumbricoides*, *Strongyloides stercoralis*, *Necator americanus*, *Ancylostoma duodenale*, *Ancylostoma caninum*, *Tichuris trichiura*, *Capillaria philippinensis*, *Trichostrongylus* species, *Trichinella* species, *Necator americanus*, *Anisakis* and related species, *Angiostrongylus costaricensis*, *Enterobius vermicularis*, Trematodes (flukes), *Fasciolopsis buski*, *Heterophyes* species, *Echinostoma* species, *Clonorchis sinensis*, *Opisthorchis* species, *Fasciola* species, *Metagonimus yokogawi*, *Schistosoma mansoni*, *Schistosoma japonicum*, *Schistosoma mekongi*, *Schistosoma intercalatum*, *Echinostoma* species and *Paragonimus* species.

In accordance with the foregoing, in various aspects, the invention may involve the treatment of a microbial infection, such as a microbial infection of the GIT, or an IBD-related microbial infection, with formulations of a pathogen is selected from the group consisting of: *Acidaminococcus fermentans*; *Acinetobacter* spp.; *Actinobaculum* spp.; *Actinomyces* spp.; *Aeromonas* spp.; *Anaerorhabdus furcosus*; *Anaerococcus hydrogenalis*; *Anaerococcus lactolyticus*; *Anaerococcus prevotii*; *Atopobium* spp.; *Bacillus* spp.; *Bacteroides caccae*; *Bacteroides distasonis*; *Bacteroides eggerthii*; *Bacteroides fragilis*; *Bacteroides merdae*; *Bacteroides ovatus*; *Bacteroides splanchnicus*; *Bacteroides thetaiotaomicron*; *Bacteroides vulgatus*; *Bifidobacterium adolescentis*; *Bifidobacterium bifidum*; *Bifidobacterium breve*; *Bifidobacterium catenulatum*; *Bifidobacterium dentium*; *Bifidobacterium longum*; *Bilophila wadsworthia*; *Burkholderia cepacia*; *Butyrivibrio fibrisolvens*; *Campylobacter concisus*; *Campylobacter curvus*; *Campylobacter gracilis*; *Campylobacter jejuni*; *Campylobacter rectus*; *Campylobacter showae*; *Capnocytophaga ochracea*; *Cedecea* spp; *Citrobacter freundii*; *Citrobacter koseri*; *Clostridium* spp.; *Desulfomonas pigra*; *Dysgonomonas* spp.; *Eikenella corrodens*; *Enterobacter aerogenes*; *Enterobacter cloacae*; *Enterobacter gergoviae*; *Enterobacter sakazakii*; *Enterobacter taylorae*; *Enterococcus* spp.; *Escherichia coli*; *Escherichia fergusonii*; *Escherichia hermannii*; *Escherichia vulneris*; *Eubacterium* spp.; *Finegoldia magnus*; *Fusobacterium gonidiaformans*; *Fusobacterium mortiferum*; *Fusobacterium naviforme*; *Fusobacterium necrophorum*; *Fusobacterium nucleatum*; *Fusobacterium russii*; *Fusobacterium varium*; *Gardnerella vaginalis*; *Gemella morbillorum*; *Globicatella* spp.; *Hafnia alvei*; *Helicobacter* spp.; *Klebsiella* spp.; *Lactobacillus acidophilus*; *Lactobacillus fermentum*; *Lactobacillus reuteri*; *Lactobacillus salivarius*; *Leclercia adecarboxylata*; *Leminorella* spp.; *Megasphaera elsdenii*; *Mitsuokella multiacidus*; *Mobiluncus curisii*; *Mobiluncus mulieris*; *Moellerella wisconsensis*; *Morganella morganii*; *Pantoea agglomerans*; *Pediococcus* spp.; *Peptoniphilus asaccharolyticus*; *Peptostreptococcus anaerobus*; *Peptostreptococcus productus*; *Porphyromonas asaccharolytica*; *Proteus mirabilis*; *Proteus penneri*; *Proteus vulgaris*; *Providencia rettgeri*; *Providencia stuartii*; *Pseudomonas aeruginosa*; *Retortamonas intestinalis*; *Ruminococcus productus*; *Serratia liquefaciens*; *Serratia marcescens*; *Serratia odorifera*; *Streptococcus agalactiae*; *Streptococcus anginosus*; *Streptococcus bovis*; *Streptococcus constellatus*; *Streptococcus intermedius*; Group C+G Streptococci; *Succinivibrio dextrinosolvens*; *Sutterella* spp.; *Tissierella praeacuta*; *Veillonella* spp.; *Aerobacter* spp.; *Bacillus anthracis*; *Bacillus cereus*; other *Bacillus* spp.; *Borrelia recurrentis*; *Brucella* spp.; *Campylobacter coli*; *Campylobacter fetus*; *Campylobacter jejuni*; *Campylobacter sputorum*; *Clostridium bifermentans*; *Clostridium botulinum*; *Clostridium difficile*; *Clostridium indolis*; *Clostridium mangenolii*; *Clostridium perfringens*; *Clostridium sordellii*; *Clostridium sporogenes*; *Clostridium subterminale*; *Edwarsiella tarda*; *Francisella tularensis*; *Listeria monocytogenes*; *Mycobacterium bovis*; *Mycobacterium tuberculosis*; *Pediococcus* spp.; *Plesiomonas shigelloides*; *Rickettsia rickettsiae*; *Salmonella* spp.; *Shigella boydii*; *Shigella dysenteriae*; *Shigella flexneri*; *Shigella sonnei*; other *Spiril-*

*lum* spp.; *Streptococcus zooepidemicus; Tropheryma whipplei; Vibrio cholerae; Vibrio fluvialis; Vibrio furnissii; Vibrio hollisae; Vibrio parahaemolyticus; Yersinia enterocolitica; Yersinia pseudotuberculosis*; Herpes Simplex virus (1 and 2); Cytomegalovirus; Adenovirus; Orthoreoviruses; Rotaviruses; Alphaviruses; Coronaviruses; Toroviruses; Human metapneumovirus; Vesicular stomatitis virus; Machupo virus; Junin virus; Poliovirus; Coxsackieviruses; Echoviruses; Hepatitis A virus; Noroviruses and other Caliciviruses; Astroviruses; Picobirnaviruses; and Hepatitis E virus.

In alternative aspects, the invention may involve the treatment of a microbial infection, such as an infection of the GIT, for example an IBD-related infection, with formulations wherein the pathogen is selected from the group of common small and larger bowel pathogens, for example the group consisting of: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri*; adenoviruses, astroviruses, caliciviruses, noroviruses, rotaviruses, and cytomegalovirus.

In selected embodiments, the invention involves diagnostic steps to assess a patient's previous exposure to an organism. For example, the diagnostic steps may include taking a medical history of exposure to selected pathogens, and/or evaluating a patient's immune response to a selected pathogen. For example, a serology test may be conducted to detect antibodies to selected pathogens in a patient's sera. In connection with this aspect of the invention, antigenic determinants of a selected pathogen may be chosen for use in an immunogenic composition on a selected patient based on a diagnostic indication that the patient has had one or more prior exposure(s) to the pathogen, for example by virtue of the presence of antibodies to antigenic determinants of that pathogen in the patient's sera.

In further selected embodiments, the invention involves diagnostic steps to assess a patient's immunological response to treatment with a selected immunogenic composition. For example, the diagnostic steps may include evaluating a patient's immune response to the antigenic determinants of that immunogenic composition, for example using a serological test to detect antibodies to those antigenic determinants. In connection with this aspect of the invention a treatment with a selected immunogenic composition may be continued if the evaluation indicates that there is an active immunological response to the antigenic determinants of that composition, and the treatment may be discontinued, and an alternative treatment with a different immunogenic composition may be initiated, if the evaluation indicates that there is not a sufficiently active immunological response to the antigenic determinants of the immunogenic composition.

One aspect of the invention involves the treatment of pathologies associated with microbial lung infections with antigenic compositions that comprise antigenic determinants of microbial pathogens that are known to be lung pathogens, such as exogenous lung pathogens or pathogens that are members of the endogenous flora of the respiratory system. For example, antigenic determinants of the endogenous bacterial respiratory flora species that most commonly cause infection in the lung (see Table 5) may be used to treat infections situated in the lung: *Streptococcus pneumoniae, Moraxella catarrhalis, Mycoplasma pneumoniae, Klebsiella pneumoniae, Haemophilus influenza*. Similarly, common viral lung pathogens from Table 5 may be selected for use in some embodiments. Alternatively, a more exhaustive list of endogenous lung pathogens may be selected from Table 1, based on the pathogenicity information provided in Table 2. In further alternative embodiments, viral lung pathogens listed in Table 4 may be used. And in further alternative embodiments, exogenous bacterial lung pathogens from Table 3 may be used in formulating antigenic compositions of the invention, i.e. selected from the group consisting of: *Achromobacter* spp., *Actinomadura* spp., *Alcaligenes* spp., *Anaplasma* spp., *Bacillus anthracis*, other *Bacillus* spp., *Balneatrix* spp., *Bartonella henselae, Bergeyella zoohelcum, Bordetella holmesii, Bordetella parapertussis, Bordetella pertussis, Borrelia burgdorferi, Borrelia recurrentis, Brucella* spp., *Burkholderia gladioli, Burkholderia mallei, Burkholderia pseudomallei, Campylobacter fetus, Capnocytophaga canimorsus, Capnoctyophaga cynodegmi, Chlamydia pneumoniae, Chlamydia psittaci, Chlamydophila pneumoniae, Chromobacterium violaceum, Chlamydophila psittaci, Chryseobacterium* spp., *Corynebacterium pseudotuberculosis, Coxiella bumetii, Francisella tularensis, Gordonia* spp., *Legionella* spp., *Leptospirosis* spp., *Mycobacterium avium, Mycobacterium kansasii, Mycobacterium tuberculosis*, other *Mycobacterium* spp., *Nocardia* spp., *Orientia tsutsugamushi, Pandoraea* spp., *Pseudomonas aeruginosa*, other *Pseudomonas* spp., *Rhodococcus* spp., *Rickettsia conorii, Rickettsia prowazekii, Rickettsia rickettsiae, Rickettsia typhi*.

Infections may also arise in bronchial tissue and therefore, in some embodiments, antigenic compositions that comprise antigenic determinants of microbial pathogens that are known to cause bronchial infection may be used to treat patients with infections situated in the bronchial tissue, including, for example, the following common causes of bronchial infection: *Mycoplasma pneumoniae, Chlamydophila pneumoniae, Bordetella pertussis, Streptococcus pneumoniae, Haemophilus influenzae*, influenza virus, adenovirus, rhinovirus, coronavirus, parainfluenza, respiratory syncytial virus, human metapneumovirus, or coxsackievirus. Infections that are located in both lung and bronchial tissue may be treated with antigenic compositions that comprise antigenic determinants of microbial pathogens that are known to cause both lung and bronchial infection (for example, *Streptococcus pneumoniae, Haemophilus influenza* and *Mycoplasma pneumoniae* are all common lung and bronchial pathogens) or alternatively, with antigenic compositions that comprise antigenic determinants of microbial pathogens that are known to cause lung infection and antigenic determinants of microbial pathogens that are known to cause bronchial infection.

One aspect of the invention involves the treatment of pathologies associated with microbial infections of the colon with antigenic compositions that comprise antigenic determinants of heterologous microbial pathogens that are known to be colon pathogens, such as pathogens that are members of the endogenous flora of the colon or exogenous colonic pathogens. For example, antigenic determinants of the following microbial species may be used to treat heterologous infections situated in the colon: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri*; adenoviruses, astroviruses, caliciviruses, noroviruses, rotaviruses, or cytomegalovirus. In selected embodiments, antigenic determinants of *E. coli*, the most common bacterial cause of colon infection, may be used alone or with antigenic determinants of other common pathogens of the colon to treat pathologies associated with infections of the colon, such as pathologies associated with infections caused by heterologous strains of *E. coli*.

In alternative aspects, the invention utilizes microbial antigens, such as bacterial or viral antigens, to formulate antigenic compositions, where the microbial species is selected on the basis of the tissue or organ within which the microbe is known to cause infections. Bacterial resident flora are the most common bacterial pathogens, accounting for the vast majority of bacterial infections in most animals, including humans. Resident flora can for example infect through primary attachment, or attachment and invasion following mucosa damage, resulting for example from vascular, trauma, chemical insult, or damage resulting from primary infection.

For microbial pathogens, virulence and infection potential is a combination of the ability of the microbe to adhere, to produce enzymes, to survive immunoproducts (complement, antibody) and to survive the microbiocidal activity of macrophage and neutrophils. Some bacteria, including endogenous bacteria, may be sufficiently virulent as to cause monomicrobial infections, while others are more effective with the synergy of polymicrobial infection. In general, it is often not possible to be precise about the specific role of individual microbes within the milieu of mixed infection. As acute infection may, in some cases, provide more optimal immune stimulation, accordingly, in some embodiments, the invention utilizes microbial species that are involved in acute infection.

In some embodiments, bacteria that are members of the endogenous flora of a particular region may be used to formulate antigenic compositions of the invention. The rows of Table 6 list a number of bacterial species, together with the biological regions in which each species may form a part of the endogenous flora. For example, *Abiotrophia* spp. are typically members of the endogenous flora of the respiratory tract and the mouth. Further and for example, the organisms listed in Table 6 may be used as microbial pathogens to formulate antigenic compositions, or antigenic compositions having those pathogens may be selected, for use to treat heterologous infections, for example as an anti-microbial treatment for heterologous infections situated in the tissues or organs listed with the relevant organism in Table 6.

TABLE 6

Human Bacterial Normal Flora (Endogenous Bacterial Human Pathogens)

| Bacterial species | Respiratory | Mouth | Stomach | Duodenum/Jejunum | Ileum | Colon | GU System | Genital | Skin |
|---|---|---|---|---|---|---|---|---|---|
| CFU/mL | | $10^5$ | $10^2$ | $10^5$ | $10^8$ | $10^{11}$ | | | |
| *Abiotrophia* spp | + | + | | | | | | | |
| *Acholeplasma laidlawii* | + | + | | | | | | | |
| *Acidaminococcus fermentans* | + | + | | + | + | + | | | |
| *Acinetobacter* spp. | + | + | | + | + | + | + | + | + |
| *Actinobacillus* spp. | + | + | | | | | | | |
| *Actinobaculum* spp. | + | | | + | + | + | | | |
| *Actinomyces* spp. | + | + | | + | + | + | + | + | |
| *Aerococcus christensenii* | | | | | | | + | | |
| *Aerococcus viridans* | | | | | | | | | + |
| *Aerococcus urinae* | | | | | | | + | | |
| *Aeromonas* spp. | | | | + | + | + | | | |
| *Alloiococcus otitis* | | | | | | | | | + |
| *Anaerorhabdus furcosus* | | | | | + | + | | | |
| *Anaerococcus hydrogenalis* | | | | | + | + | + | | + |
| *Anaerococcus lactolyticus* | | | | | + | + | + | | |
| *Anaerococcus prevotii* | | | | | + | + | + | | |
| *Arcanobacterium* spp. | + | | | | | | | | + |
| *Atopobium* spp. | + | + | | + | + | + | | | |
| *Bacillus* spp. | | | | | + | + | | | + |
| *Bacteroides caccae* | | | | | + | + | | | |
| *Bacteroides distasonis* | | | | | + | + | | | |
| *Bacteroides eggerthii* | | | | | + | + | | | |
| *Bacteroides fragilis* | | | | | + | + | + | + | |
| *Bacteroides merdae* | | | | | + | + | | | |
| *Bacteroides ovatus* | | | | | + | + | | | |
| *Bacteroides splanchnicus* | | | | | + | + | | | |
| *Bacteroides thetaiotaomicron* | | | | | + | + | | | |
| *Bacteroides vulgatus* | | | | | + | + | | | |
| *Bifidobacterium adolescentis* | | | | + | + | + | | | |
| *Bifidobacterium bifidum* | | | | + | + | + | + | + | |
| *Bifidobacterium breve* | | | | + | + | + | + | + | |
| *Bifidobacterium catenulatum* | | | | + | + | + | + | + | |
| *Bifidobacterium dentium* | + | + | | + | + | + | + | + | |

TABLE 6-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Bifidobacterium longum* | | | | + | + | + | + | + | |
| *Bilophila wadsworthia* | + | + | | + | + | + | + | + | |
| *Brevibacterium casei* | | | | | | | | | + |
| *Brevibacterium epidermidis* | | | | | | | | | + |
| *Burkholderia cepacia* | + | | | + | + | + | | | |
| *Butyrivibrio fibrisolvens* | | | | + | + | + | | | |
| *Campylobacter concisus* | + | | | + | + | + | | | |
| *Campylobacter curvus* | + | | | + | + | + | | | |
| *Campylobacter gracilis* | + | | | + | + | + | | | |
| *Campylobacter jejuni* | | | | + | + | + | | | |
| *Campylobacter rectus* | | | | + | + | + | | | |
| *Campylobacter showae* | + | + | | + | + | + | | | |
| *Campylobacter sputorum* | + | + | | | | | | | |
| *Capnocytophaga granulosum* | + | + | | | | | | | |
| *Capnocytophaga gingivalis* | + | + | | | | | | | |
| *Campylobacter haemolytica* | + | + | | | | | | | |
| *Capnocytophaga ochracea* | + | + | | + | + | + | + | + | |
| *Capnocytophaga sputigena* | + | + | | | | | | | |
| *Cardiobacterium hominis* | + | + | | | | | | | |
| *Cedecea* spp | | | | | | | + | | |
| *Centipeda periodontii* | + | + | | | | | | | |
| *Citrobacter freundii* | | | | + | + | + | | | |
| *Citrobacter koseri* | | | | + | + | + | | | |
| *Clostridium* spp. | | | | + | + | + | | | |
| *Corynebacterium accolens* | + | + | | | | | | | + |
| *Corynebacterium afermentans* | + | + | | | | | | | + |
| *Corynebacterium amycolatum* | | | | | | | | | + |
| *Corynebacterium auris* | | | | | | | | | + |
| *Corynebacterium diphtheriae* | + | | | | | | | | + |
| *Corynebacterium durum* | + | | | | | | | | |
| *Corynebacterium glucuronolyticum* | | | | | | | + | | |
| *Corynebacterium jeikeium* | | | | | | | | | + |
| *Corynebacterium macginleyi* | | | | | | | | | + |
| *Corynebacterium matruchotii* | + | | | | | | | | |
| *Corynebacterium minutissimum* | | | | | | | | | + |
| *Corynebacterium propinquum* | + | | | | | | | | |
| *Corynebacterium pseudodiphtheriticum* | + | | | | | | | | |
| *Corynebacterium riegelii* | | | | | | | + | | |
| *Corynebacterium simulans* | | | | | | | | | + |
| *Corynebacterium striatum* | + | | | | | | | | + |
| *Corynebacterium ulcerans* | + | | | | | | | | |

TABLE 6-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Corynebacterium urealyticum* | | | | | | | + | | + |
| *Dermabacter hominis* | | | | | | | | | + |
| *Dermacoccus nishinomiyaensis* | | | | | | | | | + |
| *Desulfomonas pigra* | | | | + | + | + | | | |
| *Dysgonomonas* spp. | | | | + | + | + | | | |
| *Eikenella corrodens* | + | + | | + | + | + | | | |
| *Enterobacter aerogenes* | | | | + | + | + | | | |
| *Enterobacter cloacae* | | | | + | + | + | | | |
| *Enterobacter gergoviae* | | | | + | + | + | | | |
| *Enterobacter sakazakii* | | | | + | + | + | | | |
| *Enterobacter taylorae* | | | | + | + | + | | | |
| *Enterococcus* spp. | | | | + | + | + | | | |
| *Escherichia coli* | | | | + | + | + | + | + | |
| *Escherichia fergusonii* | | | | + | + | + | | | |
| *Escherichia hermannii* | | | | + | + | + | | | |
| *Escherichia vulneris* | | | | + | + | + | | | |
| *Eubacterium* spp. | + | + | | + | + | + | | | |
| *Ewingella americana* | + | + | | | | | | | |
| *Finegoldia magnus* | | | | + | + | + | + | | + |
| *Fusobacterium alocis* | + | + | | | | | | | |
| *Fusobacterium gonidiaformans* | | | | + | + | + | + | + | |
| *Fusobacterium mortiferum* | | | | + | + | + | | | |
| *Fusobacterium naviforme* | | | | + | + | + | + | + | |
| *Fusobacterium necrophorum* | + | + | | + | + | + | | | |
| *Fusobacterium nucleatum* | + | + | | | | + | | | |
| *Fusobacterium sulci* | + | + | | | | | | | |
| *Fusobacterium russii* | | | | + | + | + | | | |
| *Fusobacterium varium* | | | | + | + | + | | | |
| *Gardnerella vaginalis* | | | | + | + | + | + | + | |
| *Gemella haemolysans* | + | + | | | | | | | |
| *Gemella morbillorum* | + | + | | + | + | + | | | |
| *Globicatella* spp. | | + | | | | + | | | |
| *Granulicatella* spp. | + | + | | | | | | | |
| *Haemophilus* spp. | + | + | | | | | | + | |
| *Hafnia alvei* | | | | + | + | + | | | |
| *Helcococcus kunzii* | | | | | | | | | + |
| *Helicobacter* spp. | | | | + | + | + | | | |
| *Kingella* spp. | + | + | | | | | | | |
| *Klebsiella* spp. | + | + | | + | + | + | | | |
| *Kocuria* spp. | | | | | | | | | + |
| *Kytococcus sedentarius* | | | | | | | | | + |
| *Lactobacillus acidophilus* | + | + | + | + | + | + | + | + | |
| *Lactobacillus breve* | + | + | | | | | | | |
| *Lactobacillus casei* | + | + | | | | | | + | + |
| *Lactobacillus cellobiosus* | | | | | | | | + | + |
| *Lactobacillus fermentum* | + | + | + | + | + | + | + | + | |
| *Lactobacillus reuteri* | | | + | + | + | + | | | |
| *Lactobacillus salivarius* | + | + | + | + | + | + | | | |
| *Lactococcus* spp. | | | | | | | + | + | |
| *Leclercia adecarboxylata* | | | | + | + | + | | | |
| *Leminorella* spp. | | | | + | + | + | | | |
| *Leptotrichia buccalis* | + | + | | | | | | + | + |
| *Leuconostoc* spp. | | | | | | | | + | + |

TABLE 6-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Megasphaera elsdenii* | | | | + | + | + | | | |
| *Micrococcus luteus* | + | + | | | | | | | + |
| *Micrococcus lylae* | + | + | | | | | | | + |
| *Micromonas micros* | + | + | | | | | | | |
| *Mitsuokella multiacidus* | | | | + | + | + | | | |
| *Mobiluncus curisii* | | | | + | + | + | | + | |
| *Mobiluncus mulieris* | | | | + | + | + | | + | |
| *Moellerella wisconsensis* | | | | + | + | + | | | |
| *Moraxella catarrhalis* | + | + | | | | | | | |
| other *Moraxella* spp. | + | + | | | | | + | | + |
| *Morganella morganii* | | | | + | + | + | | | |
| *Mycoplasma buccale* | + | + | | | | | | | |
| *Mycoplasma faucium* | + | | | | | | | | |
| *Mycoplasma fermentans* | + | + | | | | | + | | |
| *Mycoplasma genitalium* | + | | | | | | + | | |
| *Mycoplasmaa hominis* | + | + | | | | | + | | |
| *Mycoplasma lipophilum* | + | + | | | | | | | |
| *Mycoplasma orale* | + | + | | | | | | | |
| *Mycoplasma penetrans* | | | | | | | + | | |
| *Mycoplasma pneumoniae* | + | + | | | | | | | |
| *Mycoplasma primatum* | | | | | | | + | | |
| *Mycoplasma salivarium* | + | + | | | | | | | |
| *Mycoplasma spermatophilum* | | | | | | | + | | |
| *Neisseria cinerea* | + | | | | | | | | |
| *Neisseria flavescens* | + | | | | | | | | |
| *Neisseria lactamica* | + | | | | | | | | |
| *Neisseria meningitidis* | + | | | | | | | + | |
| *Neisseria mucosa* | + | | | | | | | | |
| *Neisseria polysaccharea* | + | | | | | | | | |
| *Neisseria sicca* | + | | | | | | | | |
| *Neisseria subflava* | + | | | | | | | | |
| *Oligella ureolytica* | | | | | | | + | + | |
| *Oligella urethralis* | | | | | | | + | + | |
| *Pantoea agglomerans* | | | | + | + | + | | | |
| *Pastuerella bettyae* | | | | | | | + | + | |
| *Pasteurella multocida* | + | + | | | | | | | |
| *Pediococcus* spp. | | + | | | | + | | | |
| *Peptococcus niger* | | | | | | | + | + | + |
| *Peptoniphilus asaccharolyticus* | | | | + | + | + | + | + | + |
| *Peptoniphilus lacrimalis* | + | | | | | | | | |
| *Peptostreptococcus anaerobus* | + | + | | + | + | + | | | |
| *Peptostreptococcus productus* | | | | + | + | + | | | |
| *Peptostreptococcus vaginalis* | | | | | | | + | + | + |
| *Porphyromonas asaccharolytica* | | + | | + | + | + | + | + | |
| *Porphyromonas catoniae* | + | + | | + | | | | | |
| *Porphyromonas endodontalis* | + | + | | + | | | | | |
| *Porphyromonas gingivalis* | + | + | | + | | | | | |
| *Prevotella bivia* | | | | | | | + | + | |
| *Prevotella buccae* | + | + | | + | | | | | |
| *Prevotella buccalis* | + | + | | + | | | | + | + |
| *Prevotella corporis* | + | + | | + | | | | | |
| *Prevotella dentalis* | + | + | | + | | | | | |

TABLE 6-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Prevotella denticola* | + | + |  | + |  |  |  |  |  |
| *Prevotella disiens* |  |  |  |  |  |  | + | + |  |
| *Prevotella enoeca* | + | + |  | + |  |  |  |  |  |
| *Prevotella heparinolytica* | + | + |  | + |  |  |  |  |  |
| *Prevotella intermedia* | + | + |  | + |  |  |  |  |  |
| *Prevotella loescheii* | + | + |  | + |  |  | + | + |  |
| *Prevotella melaninogenica* | + | + |  | + |  |  | + | + |  |
| *Prevotella nigrescens* | + | + |  | + |  |  |  |  |  |
| *Prevotella oralis* | + | + |  | + |  |  | + | + |  |
| *Prevotella oris* | + | + |  | + |  |  |  |  |  |
| *Prevotella oulorum* | + | + |  | + |  |  |  |  |  |
| *Prevotella tannerae* | + | + |  | + |  |  |  |  |  |
| *Prevotella veroralis* | + | + |  | + |  |  | + | + |  |
| *Prevotella zoogleoformans* | + | + |  | + |  |  |  |  |  |
| *Propionibacterium acnes* |  |  |  |  |  |  |  |  | + |
| *Propionibacterium avidum* |  |  |  |  |  |  |  |  | + |
| *Propionibacterium granulosum* |  |  |  |  |  |  |  |  | + |
| *Propionibacterium propionicum* | + | + |  |  |  |  |  |  |  |
| *Propionferax innocuum* |  |  |  |  |  |  |  |  | + |
| *Proteus mirabilis* |  |  |  |  | + | + | + |  |  |
| *Proteus penneri* |  |  |  |  | + | + | + |  |  |
| *Proteus vulgaris* |  |  |  |  | + | + | + |  |  |
| *Providencia rettgeri* |  |  |  |  | + | + |  |  |  |
| *Providencia stuartii* |  |  |  | + | + | + |  |  |  |
| *Pseudomonas aeruginosa* |  |  |  | + | + | + |  |  |  |
| *Retortamonas intestinalis* |  |  |  | + | + | + |  |  |  |
| *Rothia dentocariosa* | + | + |  |  |  |  |  |  |  |
| *Rothia mucilaginosa* | + | + |  |  |  |  |  |  |  |
| *Ruminococcus productus* |  |  |  | + | + | + |  |  |  |
| *Selenomonas* spp. | + | + |  |  |  |  |  |  |  |
| *Serratia liquefaciens* |  |  |  |  | + | + |  |  |  |
| *Serratia marcescens* |  |  |  |  | + | + |  |  |  |
| *Serratia odorifera* |  |  |  |  | + | + |  |  |  |
| *Staphylococcus aureus* | + | + |  |  |  |  | + | + | + |
| *Staphylococcus auricularis* |  |  |  |  |  |  |  |  | + |
| *Staphylococcus capitis* |  |  |  |  |  |  |  |  | + |
| *Staphylococcus caprae* |  |  |  |  |  |  |  |  | + |
| *Staphylococcus cohnii* |  |  |  |  |  |  |  |  | + |
| *Staphylococcus epidermidis* | + | + |  |  |  |  | + | + | + |
| *Staphylococcus haemolyticus* |  |  |  |  |  |  |  |  | + |
| *Staphylococcus hominis* |  |  |  |  |  |  |  |  | + |
| *Staphylococcus lugdunensis* |  |  |  |  |  |  |  |  | + |
| *Staphylococcus pasteuri* |  |  |  |  |  |  |  |  | + |
| *Staphylococcus saccharolyticus* |  |  |  |  |  |  |  |  | + |
| *Staphylococcus saprophyticus* |  |  |  |  |  |  | + |  | + |
| *Staphylococcus schleiferia* |  |  |  |  |  |  |  |  | + |
| *Staphylococcus simulans* |  |  |  |  |  |  |  |  | + |
| *Staphylococcus xylosus* |  |  |  |  |  |  |  |  | + |

TABLE 6-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| Staphylococcus warneri | | | | | | | | | + |
| Streptococcus agalactiae | | | | + | + | + | + | + | |
| Streptococcus anginosus | + | + | | + | + | + | + | + | |
| Streptococcus bovis | | | | + | + | + | | | |
| Streptococcus constellatus | + | + | | + | + | + | + | + | |
| Streptococcus criceti | + | + | | | | | | | |
| Streptococcus crista | + | + | | | | | | | |
| Streptococcus equisimilis | + | + | | | | | | | |
| Streptococcus gordonii | + | + | | | | | | | |
| Streptococcus intermedius | + | + | | | + | + | + | + | |
| Streptococcus mitis | + | + | + | | | | | | |
| Streptococcus mutans | + | + | | | | | | | |
| Streptococcus oralis | + | + | | | | | | | |
| Streptococcus parasanguis | + | + | | | | | | | |
| Streptococcus pneumoniae | + | | | | | | | | |
| Streptococcus pyogenes | + | + | + | | | | | | + |
| Streptococcus salivarius | + | + | + | | | | | | |
| Streptococcus sanguis | + | + | + | | | | | | |
| Streptococcus sobrinus | + | + | | | | | | | |
| Streptococcus vestibularis | + | + | | | | | | | |
| Group C + G Streptococci | | + | | | | + | | | |
| Succinivibrio dextrinosolvens | | | | + | + | + | | | |
| Sutterella spp. | + | + | | | + | + | + | | |
| Suttonella indologenes | + | + | | | | | | | |
| Tissierella praeacuta | | | | + | + | + | | | |
| Treponema denticola | + | + | | | | | | | |
| Treponema maltophilum | + | + | | | | | | | |
| Treponema minutum | | | | | | | + | | |
| Treponema phagedenis | | | | | | | + | | |
| Treponema refringens | | | | | | | + | | |
| Treponema socranskii | + | + | | | | | | | |
| Treponema vincentii | + | + | | | | | | | |
| Turicella otitidis | | | | | | | | | + |
| Ureaplasma urealyticum | + | + | | | | | + | | |
| Veillonella spp. | + | + | | + | + | + | | | |
| Weeksella virosa | | | | | | | + | + | |

Endogenous microbial flora, such as bacteria, have access to tissues for pathogenesis either through contiguous spread or bacteremic spread. Under favorable conditions, all endogenous organisms can become pathogenic and invade locally and spread by contiguous spread to adjacent tissues and organs. Endogenous bacterial flora of the skin, mouth and colon are the species that are understood to also be amenable to bacteremic spread. Bacteria that are members of a particular endogenous flora domain may therefore cause infection in tissues or organs to which these bacteria may spread. Accordingly, one aspect of the invention involves the use of endogenous microbial pathogens to treat an infection of a tissue or organ to which the endogenous bacteria may spread to cause infection. The columns of Table 7 list 9 domains for endogenous flora, the: skin, respiratory system, genitals, GU system, mouth, stomach, duodenum/jejunum, ileum and colon. The rows of Table 7 list organs or tissues within which heterologous microbial infections may be situated. Accordingly, one aspect of the invention involves the use of endogenous microbial pathogens to formulate antigenic compositions, or the selection of existing formulations having the pathogens, for treating heterologous microbial infections situated in tissues or organs to which the pathogen may spread to cause an infection. Accordingly, in alternative embodiments, infections situated in the tissues or organs listed in the first column of Table 7 may be treated with antigenic compositions comprising antigenic determinants that are specific for microbial pathogens that are members of the endogenous flora of one or more of the endogenous flora domains listed in the first row of Table 7 and indicated with an X or a check mark in the appropriate row. For example, infections situated in the prostate may be treated with an antigenic composition having antigenic determinants specific for a microbial pathogen or pathogens endogenous to the GU system and/or genital system. A number of the bacterial species that are endogenous to the endogenous flora domains listed in Table 7 are listed, with the corresponding endogenous flora domains, in Table 6. Accordingly, one aspect of the invention involves the treatment of an infection situated in a tissue listed in Table 7 with an antigenic composition comprising antigenic determinants of the bacterial species that are listed in Table 6, where the regions of endogenous flora linked to the site of the infection in Table 7 match the regions of endogenous flora linked to the bacterial species in Table 6. The examples provided in Tables 6 and 7 may be used to formulate antigenic compositions for use in treating heterologous microbial infections, for example as an anti-microbial treatment for heterologous microbial infections in the organs identified in Tables 6 and 7.

TABLE 7

Tissue/Organ Pathogenicity of Endogenous Flora

| Tissue/organ site | Skin | Respiratory | Genital | GU System | Mouth | Stomach | Duodenum/Jejunum | Ileum | Colon |
|---|---|---|---|---|---|---|---|---|---|
| Skin | × | | | | | × | | | |
| Soft tissue (i.e. fat and muscle) (e.g., sarcoma) | × | | | | | | | | |
| Breast | × | | | | × | | | | |
| Lymph nodes: head and neck | × | × | | | × | | | | |
| Lymph nodes: axillae/arm | × | | | | ✓ | | | | ✓ |
| Lymph nodes: mediastinal | | × | | | ✓ | | | | ✓ |
| Lymph nodes: pulmonary hilum | | × | | | | | | | |
| Lymph nodes: intra-abdominal | | | | × | ✓ | × | × | × | × |
| Lymph nodes: inguinal/leg | × | | × | | ✓ | | | | ✓ |
| Hematological (e.g. leukemias, multiple myeloma) | ✓ | | | | ✓ | | | | ✓ |
| Bone | × | | | | ✓ | | | | ✓ |
| Joints | × | ✓ | | | ✓ | | | | ✓ |
| Meninges | | × | | | × | | | | |
| Brain | ✓ | | | | ✓ | | | | ✓ |
| Spinal cord | ✓ | | | | ✓ | | | | ✓ |
| Eye/Orbit | × | × | × | | × | | | | |
| Salivary glands | | | | | × | | | | |
| Oral | | | | | × | | | | |
| Tonsil | | × | | | × | | | | |
| Nasopharynx/Sinus | | × | | | × | | | | |
| Thyroid | ✓ | | | | ✓ | | | | ✓ |
| Larynx | | × | | | × | | | | |
| Lung/Trachea/Bronchi | | × | | | | | | | |
| Pleura | ✓ | × | | | ✓ | | | | ✓ |
| Mediastinum | | × | | | | | | | |
| Heart | ✓ | | | | ✓ | | | | □ |
| Esophagus | | | | | | × | | | |
| Stomach | | | | | | × | | | |
| Small bowel | | | | | | | × | × | |
| Colon/Rectum | | | | | | | | | × |

TABLE 7-continued

Tissue/Organ Pathogenicity of Endogenous Flora

| Tissue/organ site | Skin | Respiratory | Genital | GU System | Mouth | Stomach | Duodenum/Jejunum | Ileum | Colon |
|---|---|---|---|---|---|---|---|---|---|
| Anus | × | | | | | | | | × |
| Perineum | × | | | | | | | | × |
| Liver | ✓ | | | | ✓ | | | | ✓ |
| Gallbladder | | | | | | | × | | |
| Biliary tract | | | | | | | × | | |
| Pancreas | | | | | | | × | | |
| Spleen | ✓ | | | | ✓ | | | | ✓ |
| Adrenal gland | ✓ | | | | ✓ | | | | ✓ |
| Kidney | ✓ | | | × | ✓ | | | | ✓ |
| Ureter | | | | × | | | | | |
| Bladder | ✓ | | × | × | | | | | |
| Peritoneum | | | | | | × | × | × | × |
| Retroperitoneal area | | | | × | | × | × | × | × |
| Prostate | | | × | × | | | | | |
| Testicle | | | × | × | | | | | |
| Penis | × | | × | × | | | | | |
| Ovary/Adnexae | | | × | × | | | | | × |
| Uterus | | | × | × | | | | | × |
| Cervix | | | × | × | | | | | × |
| Vagina | | | × | | | | | | × |
| Vulva | | | × | | | | | | × |

* Bacteria have access to tissues/organs either through: Contiguous spread (×) or Bacteremic spread: (✓).

In accordance with the combined information in Tables 6 and 7, infections located in the tissues or organs set out in column 1 of Table 7 may be treated with antigenic compositions comprising antigenic determinants of the corresponding but heterologous bacterial species of Table 6, so that the column headings in Table 7 are in effect replaced with the bacterial species of Table 6.

In some embodiments, microbial pathogens for use in the invention may be exongenous bacterial pathogens. For example, the organisms listed in Table 8 may be used as microbial pathogens to formulate antigenic compositions, or antigenic compositions having those pathogens may be selected, for use to treat pathologies associated with heterologous infections situated in the tissues or organs listed with the relevant organism in Table 8. In some embodiments, antigenic determinants of both endogenous and exogenous bacterial species targeted to a specific tissue or organ may be used in combination. For example, an antigenic composition derived from, or specific for, *Clostridium difficile*, may be used to treat pathologies associated with heterologous microbial infections in the colon.

TABLE 8

Exogenous Bacterial Human Pathogens, and their Sites of Infection

| bacterial species | tissue/organ sites |
|---|---|
| *Achromobacter* spp. | hematological, skin, soft tissue, lung/trachea/bronchi, peritoneum, meninges, bile duct, gallbladder, kidney, bladder, ureter |
| *Actinomadura* spp. | skin, soft tissue, lung/trachea/bronchi, mediastinum, brain, spinal cord, hematological, meninges, joints |
| *Aerobacter* spp. | small bowel, colon, hematological, peritoneum |
| *Aerococcus* spp. | hematological, heart, bone, kidney, bladder, ureter, meninges |
| *Alcaligenes* spp. | lung/trachea/bronchi |
| *Anaplasma* spp. | meninges, hematological, liver, spleen, bone, lung/trachea/bronchi |
| *Bacillus anthracis* | lung/trachea/bronchi, lymph nodes pulmonary hilum, mediastinum, meninges, skin, nasopharynx, tonsil, oral, small bowel, colon, hematological |
| *Bacillus cereus* | colon, eye, hematological |
| other *Bacillus* spp. | hematological, bone, meninges, brain, heart, lung/trachea/bronchi, mediastinum, skin, soft tissue, colon, stomach, small bowel, eye |
| *Balneatrix* spp. | lung/trachea/bronchi, meninges, hematological |
| *Bartonella bacilliformis* | skin, hematological, liver, muscle, lymph nodes, joints |
| *Bartonella henselae* | brain, spinal cord, hematological, skin, liver, bone, pleura, lung/trachea/bronchi, mediastinum, axillary and inguinal lymph nodes, eye, joints |

TABLE 8-continued

Exogenous Bacterial Human Pathogens, and their Sites of Infection

| bacterial species | tissue/organ sites |
|---|---|
| *Bartonella quintana* | skin, hematological, liver, spleen, joints |
| *Bergeyella zoohelcum* | skin, soft tissue, meninges, hematological, lung/trachea/bronchi |
| *Bordetella holmesii* | lung/trachea/bronchi, hematological |
| *Bordetella parapertussis* | nasopharynx, tonsil, lung/trachea/bronchi |
| *Bordetella pertussis* | nasopharynx, tonsil, lung/trachea/bronchi |
| *Borrelia burgdorferi* | meninges, brain, spinal cord, skin, eye, hematological, inguinal/axillary/cervical lymph nodes, muscle, liver, spleen, nasopharynx, lung/trachea/bronchi, testes, joints |
| *Borrelia recurrentis* | brain, spinal cord, hematological, small bowel, liver, spleen, salivary glands, lung/trachea/bronchi, lymph nodes, eye, skin |
| *Brevundimonas* spp. | peritoneum, hematological, skin, soft tissue |
| *Brucella* spp. | lung/trachea/bronchi, lymph nodes pulmonary hilum, meninges, brain, spinal cord, lymph nodes, mediastinum, bone, eye, small bowel, colon, liver, biliary tract, kidney, ureter, bladder, hematological, skin, testes, spleen, prostate, joints |
| *Burkholderia gladioli* | hematological, meninges, lung/trachea/bronchi |
| *Burkholderia mallei* | lung/trachea/bronchi, skin, soft tissue, liver, spleen, muscle, lymph nodes pulmonary hilum, mediastinal lymph nodes, mediastinum, head and neck lymph nodes, hematological |
| *Burkholderia pseudomallei* | lung/trachea/bronchi, skin, kidney, bladder, ureter, soft tissue, bone, brain, spinal cord, muscle, hematological, prostate, kidney, ureter, meninges |
| *Calymmatobacterium granulomatis* | skin, penis, vulva, soft tissue, vagina, cervix, bone, hematological, inguinal lymph nodes |
| *Campylobacter coli* | small bowel, colon |
| *Campylobacter fetus* | lung/trachea/bronchi, small bowel, colon, meninges, brain, peritoneum, bone, gallbladder, ovaries, hematological, heart, kidney, bladder, ureter |
| *Campylobacter jejuni* | colon, hematological, gallbladder, pancreas, bladder, bone, meninges |
| *Campylobacter sputorum* | small bowel, colon |
| *Capnoctyophaga canimorsus* | skin, soft tissue, meninges, hematological, bone, lung/trachea/bronchi, eye |
| *Capnoctyophaga cynodegmi* | skin, soft tissue, meninges, hematological, bone, lung/trachea/bronchi, eye |
| CDC groups EF-4a and EF-4b | hematological, eye, skin, soft tissue |
| *Chlamydia pneumoniae* | lung/trachea/bronchi, lymph nodes pulmonary hilum, liver, brain, meninges, skin, thyroid, pancreas, hematological |
| *Chlamydia psittaci* | lung/trachea/bronchi, lymph nodes pulmonary hilum, mediastinum, liver, brain, meninges, hematological, skin, thyroid, pancreas |
| *Chlamydia trachomatis* | inguinal lymph nodes, penis, vulva, vagina, cervix, uterus, ovaries and adnexae, peritoneum, prostate, eye |
| *Chlamydophila pneumoniae* | laryngx, trachea/bronchi, hematological |
| *Chromobacterium violaceum* | hematological, liver, spleen, lung/trachea/bronchi, kidney, bladder, ureter, eye/orbit, bone, brain, meninges, spinal cord |
| *Chlamydophila psittaci* | lung/trachea/bronchi |
| *Chryseobacterium* spp. | meninges, lung/trachea/bronchi, hematological |
| *Clostridium bifermentans* | small bowel, colon, stomach, skin, soft tissue, hematological |
| *Clostridium botulinum* | colon, small bowel, skin |
| *Clostridium difficile* | colon |
| *Clostridium indolis* | small bowel, colon, stomach, skin, soft tissue, hematological |
| *Clostridium mangenolii* | small bowel, colon, stomach, skin, soft tissue, hematological |

TABLE 8-continued

Exogenous Bacterial Human Pathogens, and their Sites of Infection

| bacterial species | tissue/organ sites |
| --- | --- |
| *Clostridium perfringens* | small bowel, colon, stomach, skin, soft tissue, hematological, heart |
| *Clostridium sordellii* | small bowel, colon, stomach, skin, soft tissue, hematological |
| *Clostridium sporogenes* | small bowel, colon, stomach, skin, soft tissue, hematological |
| *Clostridium subterminale* | small bowel, colon, stomach, skin, soft tissue, hematological |
| *Clostridium tetani* | skin, soft tissue |
| *Comamonas* spp. | hematological, peritoneum, eye |
| *Corynebacterium pseudotuberculosis* | neck/axillary/inguinal/mediastinal lymph nodes, lymph nodes pulmonary hilum, lung/trachea/bronchi, mediastinum |
| *Coxiella burnetii* | lung/bronchi/trachea, brain, spinal cord, liver, bone, joints |
| *Edwarsiella tarda* | skin, soft tissue, liver, meninges, small bowel, colon, bone, uterus, ovaries |
| *Ehrlichia* spp. | meninges, brain, spinal cord, hematological, bone, liver, kidney, spleen, lymph nodes |
| *Erysipelothrix rhusiopathiae* | skin, hematological, bone, brain, peritoneum |
| *Francisella tularensis* | nasopharynx, oral, tonsil, lung/trachea/bronchi, skin, axillary/head and neck/inguinal lymph nodes, hematological, eye, small bowel |
| *Fusobacterium* spp. | skin, soft tissue, hematological |
| *Gordonia* spp. | skin, soft tissue, lung/trachea/bronchi, mediastinum, brain, spinal cord, hematological, meninges, eye |
| *Haemophilus ducreyi* | skin, inguinal lymph nodes, penis, vulva, vagina |
| *Helicobacter pylori* | stomach |
| *Legionella* spp. | lung/trachea/bronchi, lymph nodes pulmonary hilum, hematological, brain, spinal cord, muscle, pancreas |
| *Leptospirosis* spp. | lung/trachea/bronchi, pancreas, meninges, brain, spinal cord, skin, lymph nodes, eye, hematological, nasopharynx, oral, tonsil, kidney, liver, spleen |
| *Listeria monocytogenes* | Hematological (septicemia), brain, meninges, spinal cord, small bowel, colon, GIT, cornea, lung, uterus or cervix in pregnant women |
| *Methylobacterium* spp. | hematological, peritoneum, skin, soft tissue, bone |
| *Mycobacterium avium* | lung/bronchi/trachea, lymph nodes pulmonary hilum, prostate, pancreas, spleen, skin, neck lymph nodes, esophagus, bone, hematological |
| *Mycobacterium bovis* | colon, small bowel, joints |
| *Mycobacterium kansasii* | lung/bronchi/trachea, lymph nodes pulmonary hilum, prostate, bone |
| *Mycobacterium leprae* | skin, soft tissues, testes, eye |
| *Mycobacterium marinum* | skin, soft tissue, bone |
| *Mycobacterium scrofulaceum* | head and neck lymph nodes |
| *Mycobacterium tuberculosis* | lung/bronchi/trachea, lymph nodes pulmonary hilum, prostate, peritoneum, pancreas, spleen, lymph nodes, small bowel, meninges, brain, spinal cord, kidney, ureter, bladder, muscle, esophagus, colon, testes, eye, ovaries, cervix, vagina, uterus, mediastinum, larynx, skin, hematological, pleura, joints |
| *Mycobacterium ulcerans* | skin, soft tissue |
| other *Mycobacterium* spp. | lung/bronchi/trachea, lymph nodes pulmonary hilum, skin, soft tissues, bone, head and neck lymph nodes, joints |
| *Myroides* spp. | kidney, bladder, ureter, skin, soft tissue, hematological |
| *Neisseria gonorrhoeae* | nasopharyx, oral, tonsil, prostate, penis, vagina, cervix, uterus, ovary/adnexae, peritoneum, skin, muscle, bone, liver, hematological, head and neck and inguinal and intra-abdominal lymph nodes, anus, joints |
| *Neorickettsia sennetsu* | hematological, bone, lymph nodes, liver, spleen |
| *Nocardia* spp. | lung/bronchi/trachea, pancreas, meninges, spinal cord, brain, skin, soft tissue, eye, bone, kidney, heart, hematological |

TABLE 8-continued

Exogenous Bacterial Human Pathogens, and their Sites of Infection

| bacterial species | tissue/organ sites |
|---|---|
| *Orientia tsutsugamushi* | meninges, brain, spinal cord, hematological, skin, inguinal and axillary lymph nodes, spleen, lung/bronchi/trachea |
| *Pandoraea* spp. | lung/trachea/bronchi, hematological |
| *Pasteurella canis* | skin, soft tissue, hematological |
| *Pasteurella dagmatis* | skin, soft tissue, hematological |
| *Pasteurella stomatis* | skin, soft tissue, hematological |
| *Pediococcus* spp. | hematological, liver, colon |
| *Pityrosporum ovale* | skin |
| *Plesiomonas shigelloides* | small bowel, colon, hematological, meninges, bone, gall bladder, skin, soft tissue |
| *Pseudomonas aeruginosa* | lung/trachea/bronchi, hemaotogical, skin, soft tissue, bone, meninges, brain, eye, kidney, bladder, ureter, heart, joints |
| other *Pseudomonas* spp. | skin, soft tissue, lung/trachea/bronchi, mediastinum, hematological |
| *Ralstonia* spp. | hematological, meninges, bone |
| *Rhizobium* spp. | hematological, peritoneum, eye, kidney, bladder, ureter |
| *Rhodococcus* spp. | lung/trachea/bronchi, hematological, brain, skin, lymph nodes, bone, mediastinum, liver, spleen, soft tissue, spinal cord, meninges |
| *Rickettsia akari* | skin |
| *Rickettsia conorii* | lung/bronchi/trachea, lymph nodes pulmonary hilum, meninges, brain, spinal cord, hematolofical, skin, kidney, liver, spleen, pancreas |
| *Rickettsia felis* | skin, brain, spinal cord |
| *Rickettsia prowazekii* | meninges, brain, spinal cord, hematological, lung/bronchi/trachea, skin, spleen |
| *Rickettsia rickettsiae* | lung/bronchi/trachea, lymph nodes pulmonary hilum, meninges, brain, spinal cord, hematological, muscle, small bowel, liver, skin |
| *Rickettsia slovaca* | skin, head and neck lymph nodes |
| *Rickettsia typhi* | meninges, hematological, liver, kidney, brain, lung/bronchi/trachea, spleen |
| *Roseomonas* spp. | hematological, peritoneum, skin, soft tissue, bladder, kidney, ureter |
| *Salmonella* spp. | lung/bronchi/trachea, pancreas, spleen, intra-abdominal lymph nodes, stomach, small bowel, colon, meninges, skin, muscle, bone, hematological, heart, joints |
| *Shewanella* spp. | skin, soft tissue, eye, bone, hematological, peritoneum |
| *Shigella boydii* | colon |
| *Shigella dysenteriae* | colon |
| *Shigella flexneri* | colon |
| *Shigella sonnei* | colon |
| *Sphingobacterium* spp. | brain, meninges, spinal cord, eye, skin, soft tissue |
| *Sphingomonas* spp. | hematological, meninges, peritoneum, skin, soft tissue, kidney, bladder, ureter |
| *Spirillum minus* | skin, axillary/inguinal/neck lymph nodes, hematological, liver, spleen |
| other *Spirillum* spp. | colon |
| *Stenotrophomonas maltophilia* | meninges, hematological, peritoneum, lung/trachea/bronchi, eye, kidney, bladder, ureter, skin, soft tissue |
| *Streptobacillus moniliformis* | skin, bone, hematological, lung/trachea/bronchi, meninges, brain, liver, spleen |
| *Streptococcus iniae* | skin, hematological, soft tissue |
| *Streptococcus zooepidemicus* | small bowel, nasopharynx, bone, meninges, hematological, head and neck lymph nodes |
| *Streptomices* spp. | skin, soft tissue, lung/trachea/bronchi, mediastinum, brain, spinal cord, hematological, meninges, joints |
| *Treponema pallidum* | nasopharynx, tonsil, oral, meninges, brain, spinal cord, penis, vulva, vagina, anus, cervix, eye, hematological, inguinal and head and neck lymph nodes |
| *Tropheryma whipplei* | brain, spinal cord, hematological, small bowel, colon, heart, lung/trachea/bronchi, eye |
| *Tsukamurella* spp. | skin, soft tissue, lung/trachea/bronchi, mediastinum, brain, spinal cord, hematological, meninges |
| *Vibrio cholerae* | colon, small bowel |
| *Vibrio cincinnatiensis* | hematological, meninges |

TABLE 8-continued

Exogenous Bacterial Human Pathogens, and their Sites of Infection

| bacterial species | tissue/organ sites |
| --- | --- |
| *Vibrio damsela* | skin, soft tissue |
| *Vibrio fluvialis* | small bowel, colon |
| *Vibrio furnissii* | small bowel, colon |
| *Vibrio hollisae* | small bowel, colon, skin, soft tissue |
| *Vibrio metschnikovii* | hematological |
| *Vibrio parahaemolyticus* | colon, small bowel |
| *Vibrio vulnificus* | soft tissue, blood, skin |
| *Yersinia enterocolitica* | nasopharynx, tonsil, small bowel, intra-abdominal lymph nodes, colon, muscle, lung/trachea/bronchi, liver, spleen, hematological, joints |
| *Yersinia pestis* | lung/trachea/bronchi, lymph nodes pulmonary hilum, inguinal/axillary/neck lymph nodes, oral, tonsil, hematological, skin, joints |
| *Yersinia pseudotuberculosis* | small bowel, colon, abdominal lymph nodes, joints |

In some embodiments, microbial pathogens for use in the invention may be viral pathogens. Table 9 provides an exemplary list of viral pathogens together with the tissue and organ sites for which each viral species is understood to be a pathogen. Accordingly, one aspect of the invention involves utilizing immunogenic compositions that are specific for the named viruses to treat pathologies associated with infections caused by heterologous micro-organisms in the organs or tissues that are identified adjacent to the name of the virus in Table 9. For example, an antigenic composition derived from, or specific for, a vaccinia virus, may be used to treat a condition characterized by an infection by a heterologous micro-organism in the skin, hematological tissues, lymph nodes, brain, spinal cord, eye or heart.

TABLE 9

Viral Human Pathogens and Their Sites of Infection

| virus | tissue/organ sites |
| --- | --- |
| Vaccinia | skin, hematological, lymph nodes, brain, spinal cord, eye, heart |
| Variola (smallpox) | skin, hematological, lymph nodes, brain |
| Monkeypox | skin, hematological, head and neck lymph nodes, brain, eye, lung/trachea/bronchi, pulmonary hilar lymph nodes, mediastinum, nasopharynx |
| Cowpox | skin, hematological, lymph nodes |
| Parapoxviruses | Skin |
| Molluscum contagiosum | skin |
| Tanapox | skin, hematological, axillary and inguinal lymph nodes |
| Herpes Simplex virus (1 and 2) | nasopharynx, oral, tonsil, hematological, lung/bronchi/trachea, pancreas, meninges, brain, spinal cord, inguinal and head/neck lymph nodes, penis, vulva, perineum, esophagus, liver, eye, skin, rectum, tonsil, mediastinum, anus, vagina, cervix |
| Varicella-zoster | nasopharynx, sinus, lung/trachea/bronchi, pulmonary hilar lymph nodes, hematological, pancreas, meninges, brain, spinal cord, esophagus, liver, eye, skin, heart, mediastinum |
| Cytomegalovirus | nasopharynx, lymph nodes, tonsil, hematological, lung/trachea/bronchi, pancreas, abdominal lymph nodes, brain, spinal cord, esophagus, small bowel, colon/rectum, eye, liver, heart, skin, mediastinum, esophagus |
| Epstein-Barr virus | nasopharynx, tonsil, oral, lymph nodes, hematological, lung, abdominal lymph nodes, brain, spinal cord, muscles, esophagus, liver, heart, skin, spleen, kidney, muscle, heart, lung/trachea/bronchi, pulmonary hilar lymph nodes, mediastinum |
| Human herpesvirus 6 | skin, hematological, lung/trachea/bronchi, pulmonary hilar lymph nodes, brain, meninges, liver |
| Human herpesvirus 7 | skin, brain, liver |
| Human herpesvirus 8 | nasopharynx, tonsil, hematological, skin, spleen, head and neck lymph nodes |
| Simian herpes B virus | brain, spinal cord, skin, hematological, lymph nodes |

TABLE 9-continued

Viral Human Pathogens and Their Sites of Infection

| virus | tissue/organ sites |
|---|---|
| Adenovirus | nasopharynx, oral, larynx, trachea, bronchi, lung, lymph nodes, meninges, brain, spinal cord, small bowel, colon, liver, intra-abdominal lymph nodes, mediastinum, bladder, sinus, hematological, ureter, kidney, bladder, thyroid, heart |
| BK virus | kidney |
| Human papillomavirus | skin, anus, penis, vulva, cervix, vagina, oral |
| Hepatitis B virus | liver, pancreas, hematological, bone, joints |
| Hepatitis D virus | liver |
| Parvovirus B19 | skin, hematological, nasopharynx, bone, kidney, heart, liver, brain, meninges, joints |
| Orthoreoviruses | nasopharynx, small bowel, colon, oral, sinus, lymph nodes, skin, lung/trachea/bronchi, meninges, brain, spinal cord, liver |
| Orbiviruses | brain, muscle, hematological, |
| Coltiviruses | hematological, skin, muscle, oral, spleen, lymph nodes, meninges, brain |
| Rotaviruses | small bowel, colon, liver, hematological, pancreas, nasopharynx, billiary tract, meninges, brain |
| Alphaviruses | brain, spinal cord, small bowel, colon, hematological, skin, bone |
| Rubella | skin, hematological, head and neck lymph nodes, spleen, nasopharynx, bone, brain, tonsil, bronchi, liver, heart, joints |
| Yellow fever virus | hematological, liver, lung/trachea/bronchi, kidney, adrenal gland, spleen, lymph nodes, stomach, kidney |
| Dengue fever virus | hematological, lymph nodes, skin, spleen, muscle, liver, brain, nasopharynx, joints |
| Japanese encephalitis virus | brain, hematological, spinal cord |
| West Nile encephalitis virus | brain, hematological, spinal cord, muscle, lymph nodes, liver, spleen, pancreas, meninges |
| St. Louis encephalitis virus | brain, hematological, spinal cord, meninges, muscle, nasopharynx |
| Tick-borne encephalitis virus | brain, hematological, spinal cord, muscle, meninges |
| other Flaviviruses | hematological, brain, meninges, bone, muscles, skin, lymph nodes |
| Hepatitis C virus | hematological, liver, joints |
| Hepatitis G virus | liver |
| Coronaviruses | nasopharynx, sinus, oral, tonsil, larynx, lung/trachea/bronchi, pulmonary hilar lymph nodes, small bowel, colon, tonsil, hematological |
| Toroviruses | small bowel, colon, hematological |
| Parainfluenza viruses | nasopharynx, sinus, tonsil, oral, larynx, lung/trachea/bronchi, pulmonary hilar lymph nodes, meninges, hematological, mediastinum |
| Mumps virus | salivary glands, pancreas, brain, spinal cord, liver, testes, hematological, meninges, ovaries, bone, heart, kidney, thyroid, prostate, breast, joints |
| Respiratory syncytial virus | nasopharynx, tonsil, sinus, lung/trachea/bronchi, pulmonary hilar lymph nodes, mediastinum, hematological, oral, pleura |
| Human metapneumovirus | nasopharynx, lung/trachea/bronchi, pulmonary hilar lymph nodes, tonsil, sinus, mediastinum, hematological, oral, pleura, larynx, eye, skin, small bowel, colon |
| Rubeola | nasopharynx, sinus, hematological, lung/trachea/bronchi, pulmonary hilar lymph nodes, intra-abdominal lymph nodes, meninges, brain, spinal cord, liver, spleen, lymph nodes, skin, thymus, eye, oral, heart |
| Hendra virus | brain, meninges, lung/trachea/bronchi, kidney, hematological, muscle, |
| Nipah virus | brain, meninges, spleen, lymph nodes, thymus, lung/trachea/bronchi, kidneys, brain, spinal cord, meninges, hematological |
| Vesicular stomatitis virus | hematological, muscle, oral, tonsil, nasopharyngeal, lymph nodes, small bowel, colon |
| Rabies virus | skin, meninges, brain, spinal cord, oral, nasopharynx, salivary glands, hematological |
| Lyssaviruses | brain, spinal cord |
| Influenza virus | nasopharynx, laryngx, lung/trachea/bronchi, pulmonary hilar lymph nodes, meninges, muscle, hematological, mediastinum, muscle, sinus, tonsil, oral, eye, pleura, brain, spinal cord, salivary glands, thyroid, heart |

TABLE 9-continued

Viral Human Pathogens and Their Sites of Infection

| virus | tissue/organ sites |
|---|---|
| California encephalitis virus | hematological, brain, meninges |
| Hantaviruses | hematological, kidney, eye, skin, oral, muscle, lung/trachea/bronchi |
| other Bunyaviruses | brain, hematological, muscle, meninges, spinal cord |
| Lymphocytic choriomeningitis virus | hematological, muscle, lymph nodes, skin, brain, meninges, testes, bone |
| Lassa virus | nasopharynx, brain, spinal cord, lung/trachea/bronchi, pulmonary hilar lymph nodes, mediastinum, muscle, testes, eye, heart, |
| Machupo virus | brain, meninges, hematological, muscle, eye, skin, lymph nodes, nasopharynx, small bowel, colon |
| Junin virus | brain, meninges, hematological, muscle, eye, skin, lymph nodes, nasopharynx, small bowel, colon |
| Human T-Cell Lymphotropic viruses | hematological, skin, lymph nodes, muscle, eye, bone, lung, pulmonary hilar lymph nodes, spinal cord, brain |
| Poliovirus | nasopharynx, lung/trachea/bronchi, pulmonary hilar lymph nodes, small bowel, neck and intra-abdominal lymph nodes, colon, hematological, liver, spleen, skin, brain, spinal cord, meninges, heart |
| Coxsackieviruses | nasopharynx, larynx, oral, tonsil, lung/trachea/bronchi, pulmonary hilar lymph nodes, mediastinum, pancreas, muscle, brain, meninges, small bowel, neck and intra-abdominal lymph nodes, colon, hematological, spleen, skin, eye, sinus, liver, testes, bone, pleura, salivary glands, heart |
| Echoviruses | nasopharynx, oral, tonsil, lung/trachea/bronchi, pulmonary hilar lymph nodes, muscle, brain, meninges, small bowel, neck and intra-abdominal lymph nodes, colon, hematological, mediastinum, spleen, skin, eye, sinus, liver, pancreas, testes, bone, salivary glands, heart |
| other Enteroviruses | lung/trachea/bronchi, pulmonary hilar lymph nodes, meninges, brain, skin, heart, joints |
| Hepatitis A virus | small bowel, colon, hematological, liver, spleen, brain, spinal cord, gallbladder, pancreas, kidney |
| Rhinoviruses | nasopharynx, sinus, oral, tonsil, larynx, lung/trachea/bronchi, pulmonary hilar lymph nodes |
| Noroviruses and other Caliciviruses | small bowel, colon |
| Astroviruses | small bowel, colon |
| Picobirnaviruses | small bowel, colon |
| Hepatitis E virus | liver, small bowel, colon, hematological |

The cumulative information in Tables 6 through 9 provides an extensive identification of microbial pathogens that may be used in the formulation of antigenic compositions of the invention, together with an identification of the tissues or organs in which these organisms are pathogenic, and accordingly identifies the correspondence between selected tissues or organs in which an infection by a heterologous organism is situated, and the organisms that may be used to produce antigenic formulations for treating the condition.

In some embodiments, the microbial pathogen selected for use in antigenic compositions of the invention may be one that is a common cause of acute infection in the tissue or organ in which the heterologous infection is to be treated. Table 10 identifies bacterial and viral pathogens of this kind, together with the tissues and organs in which they commonly cause infection. Accordingly, in selected embodiments, an infection residing in a tissue identified in the first column of Table 10 may be treated with an antigenic composition that comprises antigenic determinants for one or more of the heterologous pathogenic organisms listed in the second column of Table 10. For example, an infection in the skin may be treated with an antigenic composition comprising antigenic determinants of one or more of the following heterologous organisms: *Staphylococcus aureus*, Beta hemolytic streptococci group A, B, C and G, *Corynebacterium diptheriae*, *Corynebacterium ulcerans*, *Pseudomonas aeruginosa*, rubeola, rubella, varicella-zoster, echoviruses, coxsackieviruses, adenovirus, vaccinia, herpes simplex, or parvo B19.

TABLE 10

Common Causes of Acute Infection (Bacterial and Viruses) For Each Tissue/Organ Site

| Tissue/organ site | Common Bacterial or Viral Pathogens of specific tissue/organ site |
|---|---|
| Skin | *Staphylococcus aureus*, Beta hemolytic streptococci group A, B, C and G, *Corynebacterium diptheriae*, |

TABLE 10-continued

Common Causes of Acute Infection (Bacterial and Viruses) For Each Tissue/Organ Site

| Tissue/ organ site | Common Bacterial or Viral Pathogens of specific tissue/organ site |
|---|---|
| | *Corynebacterium ulcerans, Pseudomonas aeruginosa* rubeola, rubella, varicella-zoster, echoviruses, coxsackieviruses, adenovirus, vaccinia, herpes simplex, parvo B19 |
| Soft tissue (i.e. fat and muscle) (e.g., sarcoma) | *Streptococcus pyogenes, Staphylococcus aureus, Clostridium perfringens*, other *Clostridium* spp. influenza, coxsackieviruses |
| Breast | *Staphylococcus aureus, Streptococcus pyogenes* |
| Lymph nodes: head and neck | *Staphylococcus aureus, Streptococcus pyogenes* Epstein-Barr, cytomegalovirus, adenovirus, measles, rubella, herpes simplex, coxsackieviruses, varicella-zoster |
| Lymph nodes: axillae/arm | *Staphylococcus aureus, Streptococcus pyogenes* measles, rubella, Epstein-Barr, cytomegalovirus, adenovirus, varicella-zoster |
| Lymph nodes: mediastinal | viridans streptococci, *Peptococcus* spp., *Peptostreptococcus* spp., *Bacteroides* spp., *Fusobacterium* spp., *Mycobacterium tuberculosis* measles, rubella, Epstein-Barr, cytomegalovirus, varicella-zoster, adenovirus |
| Lymph nodes: pulmonary hilum | *Streptococcus pneumoniae, Moraxella catarrhalis, Mycoplasma pneumoniae, Klebsiella pneumoniae, Haemophilus influenza, Chlamydophila pneumoniae, Bordetella pertussis, Mycobacterium tuberculosis* influenza, adenovirus, rhinovirus, coronavirus, parainfluenza, respiratory syncytial virus, human metapneumovirus, coxsackievirus |
| Lymph nodes: intra-abdominal | *Yersinia enterocolitica, Yersinia pseudotuberculosis, Salmonella* spp., *Streptococcus pyogenes, Escherichia coli, Staphylococcus aureus, Mycobacterium tuberculosis* measles, rubella, Epstein-Barr, cytomegalovirus, varicella-zoster, adenovirus, influenza, coxsackieviruses |
| Lymph nodes: inguinal/leg | *Staphylococcus aureus, Streptococcus pyogenes* measles, rubella, Epstein-Barr, cytomegalovirus, herpes simplex |
| Hematological (e.g. leukemias, multiple myeloma) | *Staphylococcus aureus, Streptococcus pyogenes*, coagulase-negative staphylococci, *Enterococcus* spp., *Escherichia coli, Klebsiella* spp., *Enterobacter* spp., *Proteus* spp., *Pseudomonas aeruginosa, Bacteroides fragilis, Streptococcus pneumoniae*, group B streptococci rubeola, rubella, varicella-zoster, echoviruses, coxsackieviruses, adenovirus, Epstein-Barr, cytomegalovirus, herpes simplex |
| Bone | *Staphylococcus aureus*, coagulase-negative staphylococci, *Streptococcus pyogenes, Streptococcus pneumoniae, Streptococcus agalactiae*, other streptococci spp., *Escherichia coli, Pseudomonas* spp., *Enterobacter* spp., *Proteus* spp., *Serratia* spp. parvovirus B19, rubella, hepatitis B |
| Joint | *Staphylococcus aureus*, coagulase-negative staphylococci, *Streptococcus pyogenes, Streptococcus pneumoniae, Streptococcus agalactiae*, other streptococci spp., *Escherichia coli, Pseudomonas* spp., *Enterobacter* spp., *Proteus* spp., *Serratia* spp., *Neisseria gonorrhea, salmonella* species, *Mycobacterim tuberculosis, Hemophilus influenza* parvovirus B19, rubella, hepatitis B *Scedosporium prolificans* |
| Meninges | *Haemophilus influenzae, Neisseria meningitidis, Streptococcus pneumoniae, Streptococcus agalactiae, Listeria monocytogenes* echoviruses, coxsackieviruses, other enteroviruses, mumps |
| Brain | *Streptococcus* spp. (including *S. anginosus, S. constellatus, S. intermedius*), *Staphylococcus aureus, Bacteroides* spp., *Prevotella* spp., *Proteus* spp., *Escherichia coli, Klebsiella* spp., *Pseudomonas* spp., *Enterobacter* spp., *Borrelia burgdorferi* coxsackieviruses, echoviruses, poliovirus, other enteroviruses, mumps, herpes simplex, varicella-zoster, flaviviruses, bunyaviruses |

TABLE 10-continued

Common Causes of Acute Infection (Bacterial and Viruses) For Each Tissue/Organ Site

| Tissue/ organ site | Common Bacterial or Viral Pathogens of specific tissue/organ site |
|---|---|
| Spinal cord | *Haemophilus influenzae, Neisseria meningitidis, Streptococcus pneumoniae, Streptococcus agalactiae, Listeria monocytogenes, Borrelia burgdorferi* coxsackieviruses, echoviruses, poliovirus, other enteroviruses, mumps, herpes simplex, varicella-zoster, flaviviruses, bunyaviruses |
| Eye/Orbit | *Staphylococcus aureus, Streptococcus pyogenes, Streptococcus pneumoniae, Streptococcus milleri, Escherichia coli, Bacillus cereus, Chlamydia trachomatis, Haemophilus influenza, Pseudomonas* spp., *Klebsiella* spp., *Treponema pallidum* adenoviruses, herpes simplex, varicella-zoster, cytomegalovirus |
| Salivary glands | *Staphylococcus aureus*, viridans streptococci (e.g., *Streptococcus salivarius, Streptococcus sanguis, Streptococcus mutans*), *Peptostreptococcus* spp., *Bacteroides* spp., and other oral anaerobes mumps, influenza, enteroviruses, rabies |
| Oral | *Prevotella melaninogenicus*, anaerobic streptococci, viridans streptococci, *Actinomyces* spp., *Peptostreptococcus* spp., *Bacteroides* spp., and other oral anaerobes herpes simplex, coxsackieviruses, Epstein-Barr |
| Tonsil | *Streptococcus pyogenes*, Group C and G B-hemolytic streptococci rhinoviruses, influenza, coronavirus, adenovirus, parainfluenza, respiratory syncytial virus, herpes simplex |
| Sinus | *Streptococcus pneumoniae, Haemophilus influenza, Moraxella catarrhalis*, α-streptococci, anaerobic bacteria (e.g., *Prevotella* spp.), *Staphylococcus aureus* rhinoviruses, influenza, adenovirus, parainfluenza |
| Nasopharynx | *Streptococcus pyogenes*, Group C and G B-hemolytic streptococci rhinoviruses, influenza, coronavirus, adenovirus, parainfluenza, respiratory syncytial virus, herpes simplex |
| Thyroid | *Staphylococcus aureus, Streptococcus pyogenes, Streptococcus pneumoniae* mumps, influenza |
| Larynx | *Mycoplasma pneumoniae, Chlamydophila pneumoniae, Streptococcus pyogenes* rhinovirus, influenza, parainfluenza, adenovirus, coronavirus, human metapneumovirus |
| Trachea | *Mycoplasma pneumoniae* parainfluenza, influenza, respiratory syncytial virus, adenovirus |
| Bronchi | *Mycoplasma pneumoniae, Chlamydophila pneumoniae, Bordetella pertussis, Streptococcus pneumoniae, Haemophilus influenzae* influenza, adenovirus, rhinovirus, coronavirus, parainfluenza, respiratory syncytial virus, human metapneumovirus, coxsackievirus |
| Lung | *Streptococcus pneumoniae, Moraxella catarrhalis, Mycoplasma pneumoniae, Klebsiella pneumoniae, Haemophilus influenza* influenza, adenovirus, respiratory syncytial virus, parainfluenza |
| Pleura | *Staphylococcus aureus, Streptococcus pyogenes, Streptococcus pneumoniae, Haemophilus influenzae, Bacteroides fragilis, Prevotella* spp., *Fusobacterium nucleatum, peptostreptococcus* spp., *Mycobacterium tuberculosis* influenza, adenovirus, respiratory syncytial virus, parainfluenza |
| Mediastinum | viridans streptococci, *Peptococcus* spp., *Peptostreptococcus* spp., *Bacteroides* spp., *Fusobacterium* spp. measles, rubella, Epstein-Barr, cytomegalovirus |
| Heart | *Streptococcus* spp. (including *S. mitior, S. bovis, S. sanguis, S. mutans, S. anginosus*), *Enterococcus* spp., *Staphylococcus* spp., *Corynebacterium diptheriae, Clostridium perfringens, Neisseria meningitidis, Salmonella* spp. |

TABLE 10-continued

Common Causes of Acute Infection (Bacterial and Viruses) For Each Tissue/Organ Site

| Tissue/organ site | Common Bacterial or Viral Pathogens of specific tissue/organ site |
|---|---|
| | enteroviruses, coxsackieviruses, echoviruses, poliovirus, adenovirus, mumps, rubeola, influenza |
| Esophagus | *Actinomyces* spp., *Mycobacterium avium*, *Mycobacterium tuberculosis*, *Streptococcus* spp. |
| | cytomegalovirus, herpes simplex, varicella-zoster |
| Stomach | *Streptococcus pyogenes*, *Helicobacter pylori* |
| | cytomegalovirus, herpes simplex, Epstein-Barr, rotaviruses, noroviruses, adenoviruses |
| Small bowel | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |
| Colon/Rectum | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |
| Anus | *Streptococcus pyogenes*, *Bacteroides* spp., *Fusobacterium* spp., anaerobic streptococci, *Clostridium* spp., *E. coli*, *Enterobacter* spp., *Pseudomonas aeruginosa*, *Treponema pallidum* |
| | herpes simplex |
| Perineum | *Escherichia coli*, *Klebsiella* spp., *Enterococcus* spp., *Bacteroides* spp., *Fusobacterium* spp., *Clostridium* spp., *Pseudomonas aeruginosa*, anaerobic streptococci, *Clostridium* spp., *E. coli*, *Enterobacter* spp. |
| | herpes simplex |
| Liver | *Escherichia coli*, *Klebsiella* spp., *Streptococcus* (anginosus group), *Enterococcus* spp., other viridans streptococci, *Bacteroides* spp. |
| | hepatitis A, Epstein-Barr, herpes simplex, mumps, rubella, rubeola, varicella-zoster, coxsackieviruses, adenovirus |
| Gallbladder | *Escherichia coli*, *Klebsiella* spp., *Enterobacter* spp., enterococci, *Bacteroides* spp., *Fusobacterium* spp., *Clostridium* spp., *Salmonella enteriditis*, *Yersinia enterocolitica*, *Shigella flexneri* |
| Biliary tract | *Escherichia coli*, *Klebsiella* spp., *Enterobacter* spp., Enterococci spp., *Bacteroides* spp., *Fusobacterium* spp., *Clostridium* spp., *Salmonella enteriditis*, *Yersinia enterocolitica*, *Shigella flexneri* |
| | hepatitis A, Epstein-Barr, herpes simplex, mumps, rubella, rubeola, varicella-zoster, cocsackieviruses, adenovirus |
| Pancreas | *Escherichia coli*, *Klebsiella* spp., *Enterococcus* spp., *Pseudomonas* spp., *Staphylococcal* spp., *Mycoplasma* spp., *Salmonella typhi*, *Leptospirosis* spp., *Legionella* spp. |
| | mumps, coxsackievirus, hepatitis B, cytomegalovirus, herpes simplex 2, varicella-zoster |
| Spleen | *Streptococcus* spp., *Staphylococcus* spp., *Salmonella* spp., *Pseudomonas* spp., *Escherichia coli*, *Enterococcus* spp. |
| | Epstein-Barr, cytomegalovirus, adenovirus, measles, rubella, coxsackieviruses, varicella-zoster |
| Adrenal gland | *Streptococcus* spp., *Staphylococcus* spp., *Salmonella* spp., *Pseudomonas* spp., *Escherichia coli*, *Enterococcus* spp. |
| | varicella-zoster |
| Kidney | *Escherichia coli*, *Proteus mirabilis*, *Proteus vulgatus*, *Providentia* spp., *Morganella* spp., *Enterococcus faecalis*, *Pseudomonas aeruginosa* |
| | BK virus, mumps |
| Ureter | *Escherichia coli*, *Proteus mirabilis*, *Proteus vulgatus*, *Providentia* spp., *Morganella* spp., *Enterococcus* spp. |
| Bladder | *Escherichia coli*, *Proteus mirabilis*, *Proteus vulgatus*, *Providentia* spp., *Morganella* spp., *Enterococcus faecalis*, *Corynebacterium jekeum* |
| | adenovirus, cytomegalovirus |
| Peritoneum | *Staphylococcus aureus*, *Streptococcus pyogenes*, *Streptococcus pneumonia*, *Escherichia coli*, *Klebsiella* spp., *Proteus* spp., *Enterococci* spp., *Bacteroides fragilis*, *Prevotella melaninogenica*, *Peptococcus* spp., *Peptostreptococcus* spp., *Fusobacterium* spp., *Clostridium* spp. |

TABLE 10-continued

Common Causes of Acute Infection (Bacterial and Viruses) For Each Tissue/Organ Site

| Tissue/ organ site | Common Bacterial or Viral Pathogens of specific tissue/organ site |
|---|---|
| Retroperitoneal area | *Escherichia coli, Staphylococcus aureus* |
| Prostate | *Escherichia coli, Klebsiella* spp., *Enterobacter* spp., *Proteus mirabilis, Enterococci* spp., *Pseudomonas* spp., *Corynebacterium* spp., *Neisseria gonorrhoeae* herpes simplex |
| Testicle | *Escherichia coli, Klebsiella pneumoniae, Pseudomonas aeruginosa, Staphylococcus* spp., *Streptococcus* spp., *Salmonella enteriditis* mumps, coxsackievirus, lymphocytic choriomeningitis virus |
| Penis | *Staphylococcus aureus, Streptococcus pyogenes, Neisseria gonorrhoeae, Treponema pallidum* herpes simplex, human papillomavirus |
| Ovary/Adnexae | *Neisseria gonorrhoeae, Chlamydia trachomatis, Gardenerella vaginalis, Prevotella* spp., *Bacteroides* spp., *Peptococcus* spp. *Streptococcus* spp., *Escherichia coli* |
| Uterus | *Neisseria gonorrhoeae, Chlamydia trachomatis, Gardenerella vaginalis, Prevotella* spp., *Bacteroides* spp., *Peptococcus* spp., *Streptococcus* spp., *Escherichia coli* |
| Cervix | *Neisseria gonorrhoeae, Chlamydia trachomatis, Treponema pallidum* herpes simplex |
| Vagina | *Gardenerella vaginalis, Prevotella* spp., *Bacteroides* spp., peptococci spp., *Escherichia coli, Neisseria gonorrhoeae, Chlamydia Trachomatis, Treponema pallidum,* herpes simplex |
| Vulva | *Staphylococcus aureus, Streptococcus pyogenes, Treponema pallidum* herpes simplex |

In selected embodiments, particular microbial pathogens are suited for treatment of particular pathologies associated with heterologous microbal infections located in the tissue or organ within which the organism is pathogenic, examples of selected embodiments are set out in Table 10. These are exemplary embodiments, and not an exhaustive list of the alternative formulations for use in accordance with the invention.

The specific microbes which commonly cause infection in a specific tissue or organ may vary by geographical location. For example, *Mycobacterium tuberculosis* is a more common cause of lung infection in some geographical locations and populations than in others and therefore, while *M. tuberculosis* may not be a common lung pathogen in some geographic and population groups it may be a common lung pathogen in others. Table 10 is thus not an exhaustive list of common pathogens for all geographic locations and population groups. It is understood that a clinical microbiologist skilled in the art could determine the common pathogenic species in a particular geographic area or population group for a specific tissue or organ site in accordance with the invention. For veterinary use, there will of course be specific pathogens that are common in selected tissues of selected species, and this may also vary geographically.

In selected embodiments, the invention involves diagnostic steps to assess a patient's previous exposure to microbial pathogens. For example, the diagnostic steps may include taking a medical history of exposure to selected pathogens, and/or evaluating a patient's immune response to a selected pathogen. For example, a serology test may be conducted to detect antibodies to selected pathogens in a patient's sera. In connection with this aspect of the invention, antigenic determinants of a selected microbial pathogen may be chosen for use in an immunogenic composition on a selected patient based on a diagnostic indication that the patient has had one or more prior exposure(s) to the pathogen, for example by virtue of the presence of antibodies to antigenic determinants of that pathogen in the patient's sera.

In further selected embodiments, the invention involves diagnostic steps to assess a patient's immunological response to treatment with a selected immunogenic composition. For example, the diagnostic steps may include evaluating a patient's immune response to the antigenic determinants of that immunogenic composition, for example using a serological test to detect antibodies to those antigenic determinants. In connection with this aspect of the invention a treatment with a selected immunogenic composition may be continued if the evaluation indicates that there is an active immunological response to the antigenic determinants of that composition, and the treatment may be discontinued, and an alternative treatment with a different immunogenic composition may be initiated, if the evaluation indicates that there is not a sufficiently active immunological response to the antigenic determinants of the immunogenic composition.

In selected embodiments, the microbial pathogen selected for use in antigenic compositions of the invention may be one that is the most common cause of acute infection in the tissue or organ in which the heterologous infection is to be treated. For example, for the treatment of pathologies associated with infections of the bone, *Staphylococcus aureus* would be the bacterial species selected for treatment of infections caused by heterologous organisms; for the treatment of infections in lung tissue, *Streptococcus pneumoniae* would be selected for treatment of infections caused by heterologous organisms; for the treatment of breast infections, *Staphylococcus aureus* would be selected for treatment of infections caused by heterologous organisms; for the treatment of kidney or bladder infections, *Escherichia*

*coli* would be selected for treatment of infections caused by heterologous organisms; and for the treatment of infections in the colon, *Escherichia coli* would be the bacterial species selected for treatment of infections caused by heterologous organisms. It is understood that a clinical microbiologist skilled in the art could determine the most frequently pathogenic species, bacterial or viral, for each specific tissue or organ in accordance with the invention. In selected embodiments, only antigenic determinants of the most common pathogen for the particular tissue or organ are used to treat heterologous infections of that tissue or organ. In alternative embodiments, antigenic determinants of the most common pathogen for the particular tissue or organ could be used in combination with antigenic determinants of other pathogens that are known to be pathogenic in the of that particular tissue or organ, preferentially selecting from the more common pathogens.

In some embodiments, the invention provides antigenic compositions in which a threshold proportion of antigenic determinants selected in accordance with the invention are used, relative to any other antigenic determinants in the composition. For example, antigenic compositions may have greater than X % of the antigenic determinants therein derived from pathogenic (or commonly pathogenic, or most commonly pathogenic) species, where X may for example be 10, 30, 40, 50, 60, 70, 80, 90, 95 or 100 (or any integer value between 10 and 100). For example, at least X % of the antigenic determinants in the antigenic composition may be specific for microbial pathogens that are pathogenic (or commonly pathogenic or most commonly pathogenic) in the specific organ or tissue of the patient within which the heterologous infection is situated. Using an alternative measure, of the total number of microbial pathogens in the antigenic composition, at least X % may be selected to be microbial pathogens that are pathogenic (or commonly pathogenic or most commonly pathogenic) in the specific organ or tissue of the patient within which the heterologous microbial infection is situated. In some embodiments, the antigenic composition may accordingly consist essentially of antigenic determinants of one or more microbial pathogens that are each pathogenic (or commonly pathogenic or most commonly pathogenic) in the specific organ or tissue of the patient within which the heterologous infection is situated.

In some embodiments, the invention comprises the use of bacterial or viral vaccines or formulations that are approved for other purposes (e.g., poliomyelitis vaccine, H. influenza vaccine, meningococcal vaccine, pneumococcal vaccine, influenza vaccine, hepatitis B vaccine, hepatitis A vaccine, diphtheria vaccine, tetanus vaccine, pertussis vaccine, measles vaccine, mumps vaccine, rubella vaccine, varicella vaccine, BCG vaccine, cholera vaccine, Japanese encephalitis vaccine, rabies vaccine, typhoid vaccine, yellow fever vaccine, small pox vaccine, etc.) for use as treatments of infections caused by heterologous micro-organisms by selecting a vaccine containing a pathogen (or antigenic constituent of a pathogen) that is pathogenic in the specific organ or tissue of the patient within which the heterologous infection is situated by consulting Tables 6-10. For example, a *S. pneumoniae* vaccine, either a whole cell vaccine or a vaccine comprised of one or more antigenic components of *S. pneumoniae* (e.g., pneumococcal polysaccharide-23-valent) could be used to treat a heterologous infection at any of the following sites in which *S. pneumoniae* is listed as a common pathogen in Table 10: pulmonary hilar lymph nodes, bone, meninges, spinal cord, eye/orbit, sinus, thyroid, bronchi, lungs, pleura or peritoneum. As a further example, a hepatitis B vaccine could be used to treat a heterologous infection at any of the following sites in which hepatitis B virus is listed as a pathogen in Table 9, as follows: liver, pancreas, or hematological infections.

In some embodiments, selected compositions and methods are specifically excluded from the scope of the invention. For example, the use of the a formulation of antigens of a particular microbial pathogen in the treatment of a pathology associated with infection by that organism. For example, selected embodiments exclude the use of PVF or MRV vaccines for the treatment of lung infections caused by the organisms that are present in those formulations.

Example 1: Murine Studies

Example 1a: Illustrating the Influence of a Heat Inactivated *Klebsiella pneumoniae* Antigenic Composition on Monocyte/Macrophage and Dendritic Cell Populations in Mice The following methods and materials were utilized in this Example:

Mice.

C57BL/6 female mice 7-8 weeks of age were ordered from Harlan Labs (Livermore, Calif.) for these studies.

Antibodies and Reagents.

The following antibodies were used in this Example: anti-I-A/I-E FITC (MHC Class II; M5/114.15.2); anti-Gr-1 PE (RB6-8C5); anti-CD11b PerCP-Cy5 (M1/70); anti-CD11c APC (N418); anti-CD4 FITC (GK1.5); anti-NK1.1 PE (PK136); anti-CD8a eFluor780 (53-6.7); anti-CD44 APC (IM7). All antibodies were acquired from eBioscience (San Diego, Calif.). Liberase TM and DNAse I was acquired from Roche. All media was from HyClone (Fisher).

Treatment with Antigenic Compositions.

Heat killed *K. pneumoniae* with phenol (KO12 [5.0 OD600 units]) was diluted 1/10 in PBS containing 0.4% phenol and 100 µl was injected subcutaneously on day 0, 2, 4, and 6 into 4 mice. Control mice (n=5) were injected on day 0, 2, 4, and 6 with PBS.

Brochoalveolar Lavage.

On day 7 mice were sacrificed and a bronchoalveolar lavage (BAL) was performed by exposing the trachea followed by insertion of a 22G catheter attached to a 1 ml syringe. 1 ml of PBS was injected into the lungs and removed and placed into a 1.5 ml microcentrifuge tube. The lungs were subsequently washed 3 more times with 1 ml of PBS and the fluid was pooled. The first wash from each mouse was centrifuged at 400×g and the supernatant was frozen for cytokine analysis. The final 3 ml of lavage fluid was centrifuged and the cells were pooled with the cell pellet from the first lavage. The cells were counted and stained with antibodies specific for MHC class 11, Ly6G/C, CD11b, and CD11c. After staining the cells were washed and analyzed on a FACS Calibur flow cytometer.

Lung Digestion.

After BAL was performed the lungs were placed in 5 ml of RPMI containing 417.5 µg/ml Liberase TL (Roche) and 200 µg/ml DNAse I (Roche). The lungs were then digested at 37° C. for 30 mins. After digestion the lungs were forced through a 70 um cell strainer to create a single cell suspension. The cells were then centrifuged, washed, resuspended in FACS Buffer (PBS with 2% FCS and 5 mM EDTA) and counted. After counting the cells were stained and analyzed by FACS using the same antibodies as for the BAL cells.

Peritoneal Lavage.

1 ml of PBS was injected into the peritoneum of mice using a 1 ml syringe attached to a 25G needle after BAL. The abdomen was massaged for 1 minute and 0.5 ml of PBS was recovered from the peritoneum using a 1 ml pipet. The lavage fluid was put in a 1.5 ml centrifuge tube, centrifuged at 400×g for 5 mins, and resuspended in FACS buffer prior to staining and FACS analysis.

Spleen and Lymph Node Analysis.

The spleen and draining lymph node were removed after BAL and peritoneal lavage and placed in PBS. The spleen was disrupted by mashing through a 70 μm cell strainer (Fisher) and the lymph node was disrupted using the rubber end of the plunger from a 1 ml syringe. After disruption, the single cell suspension from the spleen and lymph nodes was centrifuged, washed once with FACS Buffer, and resuspended in FACS Buffer prior to counting, staining, and FACS analysis.

FACS Analysis.

Cells were stained on ice for 20 mins in 96 well plates using 50 ul of antibodies diluted in FACS buffer. After 20 mins, 100 μl of FACs buffer was added to the wells and the plates were centrifuged at 400×g for 5 mins. Subsequently the media was removed and the cells were washed 1 more time with FACS buffer. After the final wash the cells were resuspended in 200 μl of FACS buffer and the data was acquired using a FACS Calibur flow cytometer (BD). A minimum of 20,000 live events were collected for all samples except the BAL where a minimum of 5,000 events was collected.

The following results were obtained in this Example.

Figure 1B:
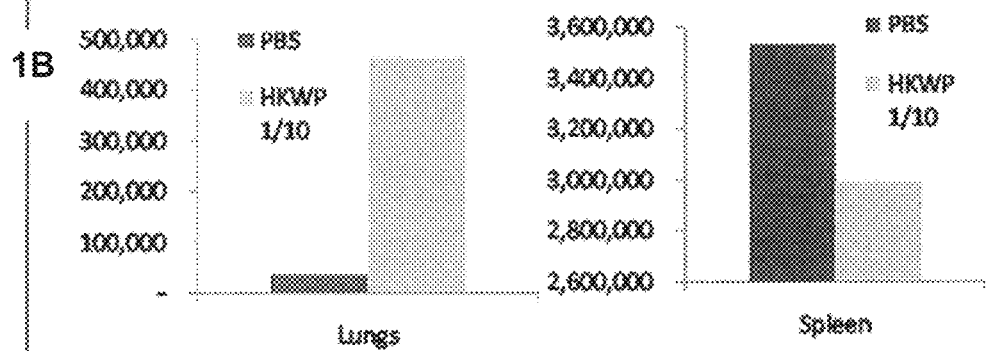
Figure 1C:
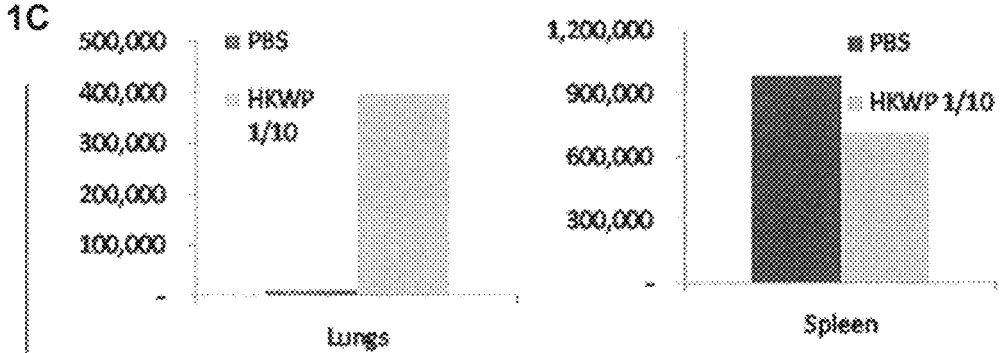

Normal mice were treated with a K. pneumoniae antigenic composition on day 0, 2, 4, and 6. On day 7 the mice were sacrificed and the bronchoalveolar lavage fluid, lung tissue, peritoneal lavage fluid, lymph nodes, and spleen was analyzed for changes in monocyte and macrophages. An increase in the number of acute inflammatory blood monocytes/macrophages, defined by high expression of CD11b and Gr-1 (same marker as Ly6c), and F4/80 in the lymph node draining the site of injection of the K. pneumoniae antigenic composition was observed (see: FIG. 1A). These acute inflammatory monocytes/macrophages also express very high levels of MHC class II molecules suggesting exposure to bacterial antigens. Importantly, treatment of mice with the K. pneumoniae antigenic composition for one week led to a marked increase in the frequency of acute inflammatory monocytes in the bronchoalveolar lavage fluid and in the lungs (i.e., the targeted organ) but not in the spleen or peritoneum of treated mice, suggesting that treatment can induce homing of monocytes specifically to the lungs without affecting other organs (see: FIG. 1B). Monocytes can differentiate into dendritic cells (DCs) in the lungs and consistent with our observations of a marked increase in monocyte recruitment it was also observed that there was a marked increase in the frequency of cells displaying markers for mature DCs (see: FIG. 1C).

As illustrated in FIGS. 1A to 1C, treatment with a K. pneumoniae antigenic composition for 7 days resulted in a marked increase (compared to treatment with placebo=PBS) in both acute inflammatory monocytes and dendritic cells in the lungs of mice. As illustrated in FIGS. 1A to 1C, mice were treated with either a K. pneumoniae antigenic composition for or PBS on day 0, 2, 4, and 6. On day 7, the mice were sacrificed and the total number of A) and B) inflammatory monocytes (CD11b+ Gr-1+ cells) and C) dendritic cells (CD11c+ MHC class II+ cells) were determined by flow cytometry in the lung and spleen. The error bars depicted in A) represent the mean of 4-5 mice per group.

Example 1B. Illustrating the Influence of a Heat Inactivated *Klebsiella pneumoniae* Antigenic Composition and a Heat Inactivated *E. coli* Antigenic Composition on Monocyte/Macrophage, Dendritic Cell, and Effector Cell Populations in Mice The following methods and materials were utilized in this Example:

Mice.

C57BL/6 female mice 7-8 weeks of age were ordered from Harlan Labs (Livermore, Calif.) for these studies.

Antibodies and Reagents.

The following antibodies were used: anti-I-A/I-E FITC (MHC Class II; M5/114.15.2); anti-Gr-1 PE (RB6-8C5); anti-CD11b PerCP-Cy5 (M1/70); anti-CD11c APC (N418); anti-CD4 FITC (GK1.5); anti-NK1.1 PE (PK136); anti-CD8a eFluor780 (53-6.7); anti-CD44 APC (IM7). All antibodies were acquired from eBioscience (San Diego, Calif.). Liberase TM and DNAse I was acquired from Roche. All media was from HyClone (Fisher).

Treatment with Antigenic Compositions.

Heat-killed K. pneumoniae with phenol (K. pneumoniae; lot KO12; 5.0 OD600 units) was diluted 1/10 in PBS containing 0.4% phenol and 100 ul was injected subcutaneously on day 0, 2, 4, and 6 into 5 mice. Heat-killed E. coli (lot; 5.0 OD600 units) was diluted 1/10 in containing 0.4% phenol and 100 μl was injected subcutaneously on day 0, 2, 4, and 6 into 5 mice. Control mice (n=5) were injected on day 0, 2, 4, and 6 with PBS.

Brochoalveolar Lavage.

On day 7 mice were sacrificed and a bronchoalveolar lavage (BAL) was performed by exposing the trachea followed by insertion of a 22G catheter attached to a 1 ml syringe. 1 ml of PBS was injected into the lungs and removed and placed into a 1.5 ml microcentrifuge tube. The lungs were subsequently washed 3 more times with 1 ml of PBS and the fluid was pooled. The first wash from each mouse was centrifuged at 400×g and the supernatant was frozen for cytokine analysis. The final 3 ml of lavage fluid was centrifuged and the cells were pooled with the cell pellet from the first lavage. The cells were counted and stained with antibodies specific for MHC class II, Ly6G/C, CD11b, and CD11c. After staining the cells were washed and analyzed on a FACS Calibur flow cytometer.

Lung Digestion.

After BAL was performed the lungs were placed in 5 ml of RPMI containing 417.5 μg/ml Liberase TL (Roche) and 200 μg/ml DNAse I (Roche). The lungs were then digested at 37° C. for 30 mins. After digestion the lungs were forced through a 70 μm cell strainer to create a single cell suspension. The cells were then centrifuged, washed, resuspended in FACS Buffer (PBS with 2% FCS and 5 mM EDTA) and counted. After counting the cells were stained and analyzed by FACS using the same antibodies as for the BAL cells.

Peritoneal Lavage.

1 ml of PBS was injected into the peritoneum of mice using a 1 ml syringe attached to a 25G needle after BAL. The abdomen was massaged for 1 minute and 0.5 ml of PBS was recovered from the peritoneum using a 1 ml pipet. The lavage fluid was put in a 1.5 ml centrifuge tube, centrifuged at 400×g for 5 mins, and resuspended in FACS buffer prior to staining and FACS analysis.

Spleen and Lymph Node Analysis.

The spleen and draining lymph node were removed after BAL and peritoneal lavage and placed in PBS. The spleen was disrupted by mashing through a 70 μm cell strainer (Fisher) and the lymph node was disrupted using the rubber end of the plunger from a 1 ml syringe. After disruption, the single cell suspension from the spleen and lymph nodes was centrifuged, washed once with FACS Buffer, and resuspended in FACS Buffer prior to counting, staining, and FACS analysis.

FACS Analysis.

Cells were stained on ice for 20 mins in 96 well plates using 50 μl of antibodies diluted in FACS buffer. After 20 mins, 100 μl of FACs buffer was added to the wells and the plates were centrifuged at 400×g for 5 mins. Subsequently the media was removed and the cells were washed 1 more time with FACS buffer. After the final wash the cells were resuspended in 200 μl of FACS buffer and the data was acquired using a FACS Calibur flow cytometer (BD). A minimum of 20,000 live events were collected for all samples except the BAL where a minimum of 5,000 events was collected.

Figure 2:
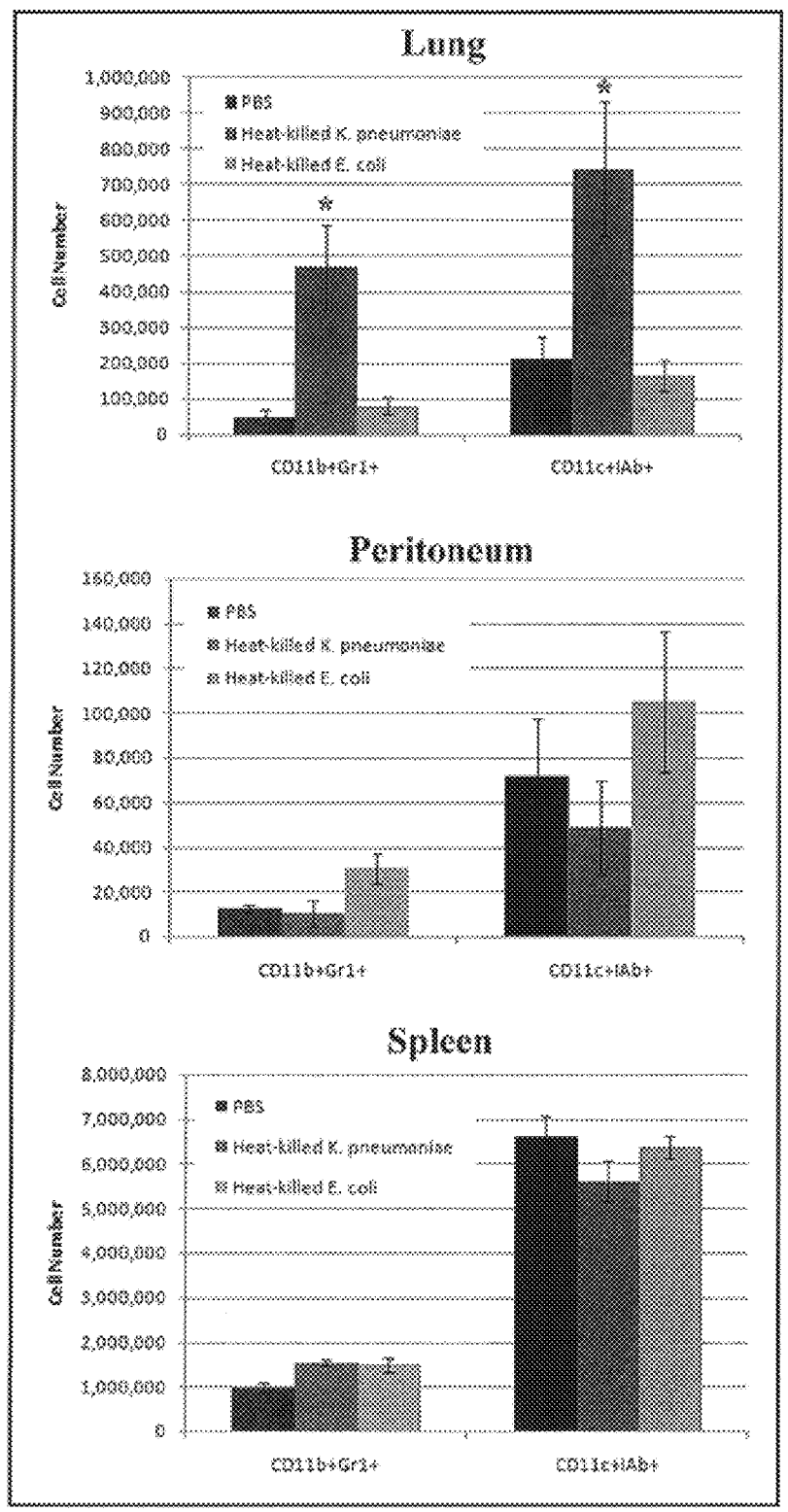
FIG. 2 shows the total number of monocytes and dendritic cells in the lung, peritoneum and spleen of mice following treatment with either a *K. pneumoniae* antigenic composition, an *E. coli* antigenic composition, or PBS, as described in Example 1B herein.
Figure 18:
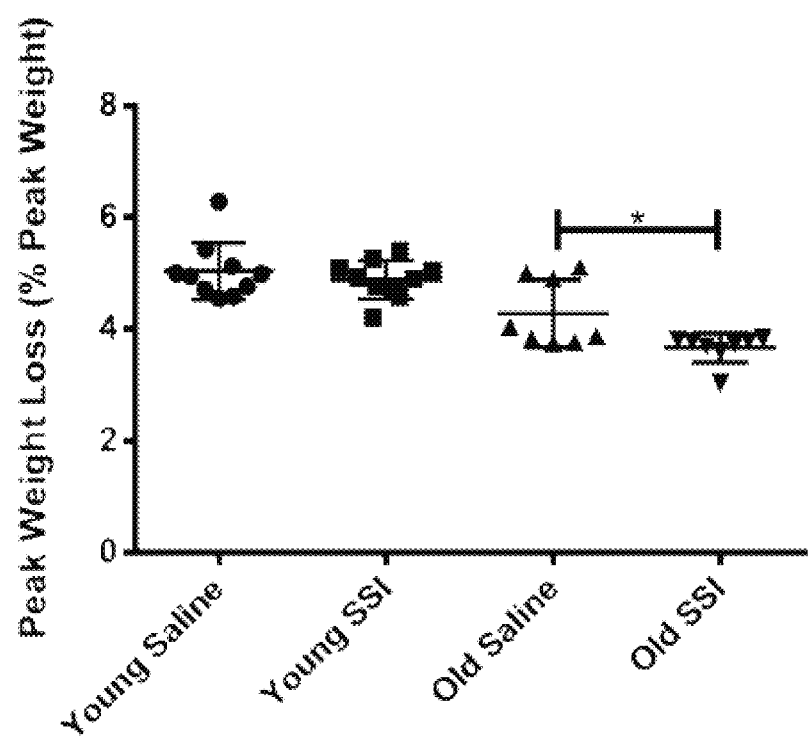
FIG. 18 is a graph illustrating that QBKPN SSI reduces weight loss in aged mice, following challenge with *S. pneumoniae*, and this benefit is greater for aged mice compared to young mice.

The following results were obtained in this Example:

As illustrated in FIG. 2, mice were treated on day 0, 2, 4, and 6 with either a *K. pneumoniae* antigenic composition, an *E. coli* antigenic composition or PBS. On day 7 the mice were sacrificed and the total number of inflammatory monocytes (CD11b+ Gr-1+ cells) and dendritic cells (CD11c+ MHC class II+ cells) were determined by flow cytometry in the peritoneal lavage fluid, lungs, lymph node and spleen. Error bars in FIG. 18 represent the standard deviation from 5 mice. *p-value<0.05 using a Student's t-test.

FIG. 2 illustrates that treatment with a *K. pneumoniae* antigenic composition, but not an *E. coli* antigenic composition treatment, markedly increased the number of monocytes and DCs in the lungs of mice. In contrast to the lungs, *K. pneumoniae* did not lead to an increase in monocytes in the peritoneum of the mice whereas *E. coli* did. Importantly, there was only a slight increase in the number of inflammatory monocytes and no increase in DCs in the spleens of mice treated with either *K. pneumoniae* or *E. coli* suggesting that the effects of the therapies are not general and are, in fact, specific for a particular organ site. In addition to looking at the effects of treatment on inflammatory monocytes and DCs in the lungs of mice, we also looked at changes in other leukocytes such as cytotoxic CD8 T cells, CD4 T helper cells, and natural killer (NK) cells.

Figure 3:
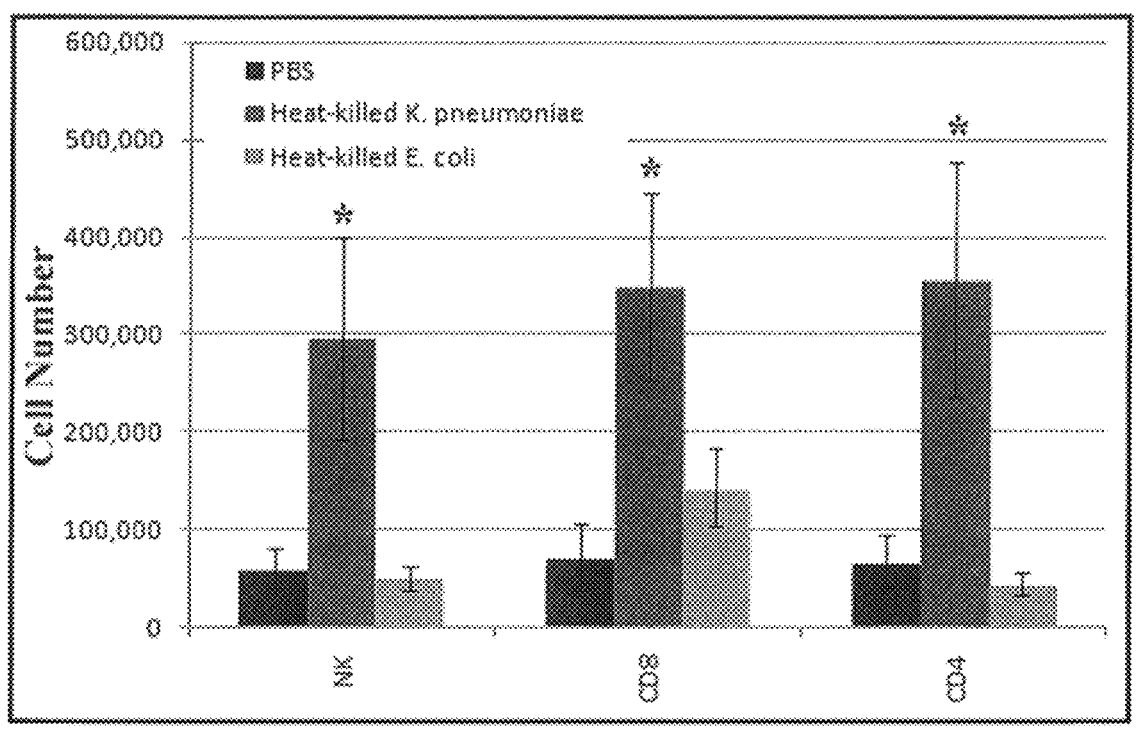
FIG. 3 shows the total number of CD4+ T cells, CD8+ T cells, and NK cells from mice treated with either a *K. pneumoniae* antigenic composition, an *E. coli* antigenic composition, or PBS, as described in Example 1B herein.

FIG. 3 illustrates that a *K. pneumoniae* antigenic composition, but not PBS or an *E. coli* antigenic composition, resulted in a marked increase in the frequency and total numbers of NK cells, CD4 and CD8 T cells in the lungs of treated mice. This Example demonstrates that subcutaneous injection of a killed bacterial species which normally causes lung infection can promote the accumulation of leukocytes in the lungs without the presence of any inflammation in that site. In addition, it demonstrates that this effect is specific to the targeted site and that it is also specific to the bacterial constituents of the treatment used.

As illustrated in FIG. 3, mice were treated on day 0, 2, 4, and 6 with either a *K. pneumoniae* antigenic composition, an *E. coli* antigenic composition, or PBS. On day 7, the mice were sacrificed and the total number of CD4 T cells, CD8 T cells, and natural killer (NK) cells were determined by flow cytometry. Error bars represent the sd of values obtained from 5 mice per group. *p-value<0.05 using a Student's t-test.

Example 1C. Illustrating the Effects of Heat, Irradiation, and Phenol Inactivation on *K. pneumoniae* Antigenic Compositions, Including Leukocyte Recruitment into the Lungs of Mice, and the Effects of Phenol as a Preservative The following methods and materials were utilized in this Example:

Mice.

C57BL/6 female mice 7-8 weeks of age were ordered from Harlan Labs (Livermore, Calif.) for these studies.

Antigenic Compositions.

Heat killed *K. pneumoniae* antigenic composition with phenol (KO12), heat killed *K. pneumoniae* antigenic composition without phenol (KO25), irradiated *K. pneumoniae* antigenic composition without phenol (KO24), and phenol killed *K. pneumoniae* antigenic composition without phenol (KO25) were used in this study. All bacterial formulations were at a concentration of 5.0 OD units in saline. For 1/10 dilution, 1 ml of bacterial formulation was added to 9 ml of DPBS and mixed immediately and then again prior to injection. For 1/100 dilution, 0.1 ml of bacterial formulation will be added to 9.9 ml of DPBS and mixed immediately and then again prior to injection. For dilutions of heat-killed *Klebsiella pneumoniae* antigenic composition with phenol, the dilutions were carried out as above using a DPBS solution containing 0.4% phenol (w/v). To prepare the 0.4% phenol in DPBS, first a 5% phenol solution was prepared by adding 0.5 g of solid phenol (Sigma Aldrich, St. Louis, Mo.) to 10 ml of DPBS (Hyclone, Logan, Utah) This solution was filtered through a 0.22 um filter (Millipore, Billerica, Mass.) and stored at 4° C. Immediately prior to use the 5% phenol solution was diluted 1 ml in 12.5 ml DPBS and used to prepare the bacterial formulations.

Treatment with Antigenic Compositions.

5 mice per group were treated subcutaneously on day 0, 2, 4, and 6 with 0.1 ml of a heat-killed *K. pneumoniae* antigenic composition diluted 1/10 in PBS or PBS with 0.4% phenol, 0.1 ml of an irradiated *K. pneumoniae* antigenic composition diluted 1/10 in PBS, or a phenol inactivated *K. pneumoniae* antigenic composition diluted 1/10 with PBS or PBS with 0.4% phenol. On day 7 the mice were sacrificed and leukocyte recruitment to the lungs was analyzed as in Example 1B.

Figure 4:
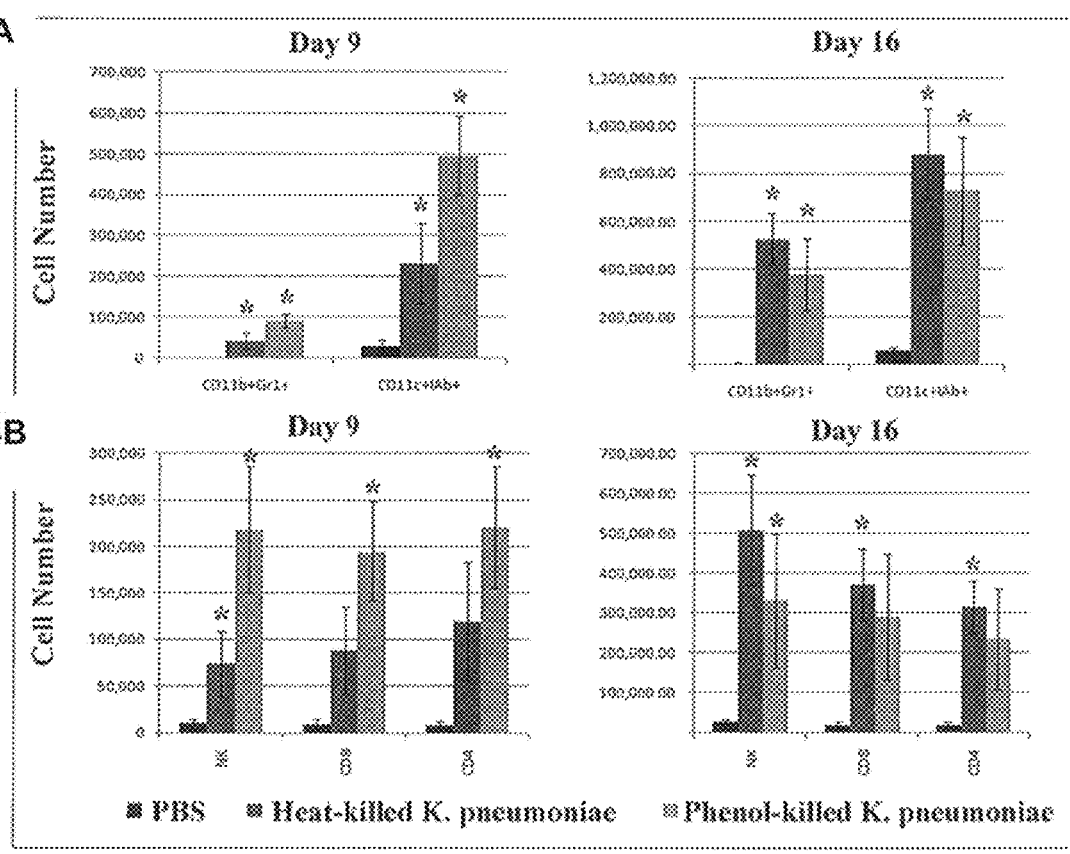
FIGS. 4A and 4B show the total number of (A) inflammatory monocytes and dendritic cells and (B) CD4+ T cells, CD8+ T cells, and NK cells from mice treated with either a heat-inactivated *K. pneumoniae* antigenic composition, a phenol-inactivated *K. pneumoniae* antigenic composition, or PBS, as described in Example 10 herein.

The following results were obtained in this Example:

In this example, we used leukocyte recruitment to the lungs as a surrogate of efficacy to compare the efficacy of *K. pneumoniae* antigenic compositions inactivated by various methods. FIGS. 4A to 4B illustrate that, for both heat killed and phenol killed *K. pneumoniae* antigenic compositions, the addition of phenol (0.4%) as a preservative, increased efficacy, as measured by cellular recruitment. In some embodiments, a small amount of phenol (i.e., 0.4% as a preservative) may stabilize a component of the bacterial cell wall, for example a component that is important in antigen pattern recognition and activating an optimal targeted response. In comparing the 3 formulations containing phenol as a preservative (i.e., heat killed, phenol killed and radiation killed), irradiated *K. pneumoniae* antigenic composition led to the greatest recruitment of acute inflammatory monocytes, DCs, NK cells, and T cells to the lungs, followed by phenol killed *K. pneumoniae* antigenic composition, with heat killed *K. pneumoniae* antigenic composition resulting in the least cellular recruitment.

As illustrated in FIGS. 4A to 4B, mice were treated on day 0, 2, 4, and 6 with *K. pneumoniae* antigenic composition inactivated by heat (HKWP) or without (HKnp) phenol preservative, inactivated with phenol with (PKWP) or without (PKnp) phenol preservative, or *K. pneumoniae* antigenic composition inactivated by irradiation with phenol preservative (IRWP). On day 7 the mice were sacrificed and the total numbers of (A) inflammatory monocytes (CD11b+ Gr-1+) and DCs (CD11c+ Iab+) or (B) CD4 T cells, CD8 T cells, and natural killer (NK) cells were determined by flow cytometry. Error bars represent the sd of values from 5 mice per group. *p-value<0.05 compared to mice treated with IRWP using a Student's t-test.

Example 2: Site Specificity Studies

Figure 5:
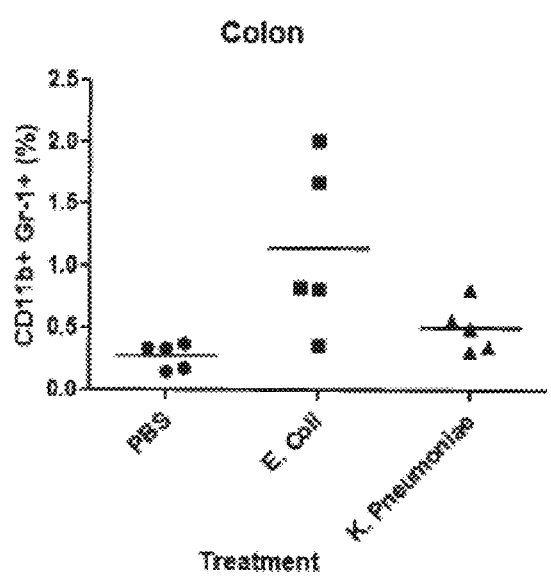
FIG. 5 shows the relative frequency of CD11b+ Gr-1+ cells detected from the colons of mice treated with either *K. pneumoniae* or *E. coli* antigenic compositions or with PBS control.

With a focus on investigating the M1/M2 phenotypes in the in vivo model described herein which is used in conjunction with the antigenic compositions described herein, the following experiments were performed. Briefly, 5 mice per group were treated on day 0, 2, 4, and 6 with either PBS, *E. coli* colon antigenic compositions, or *K. pneumoniae* antigenic compositions. On day 7 of the experiment, the mice were sacrificed and a bronchoalveolar lavage was performed. Subsequently the lungs and proximal colon were removed and enzymatically digested. After digestion, the recovered cells were washed and stained with antibodies specific for I-A/I-E FITC (MHC class II; M5/114.15.2); anti-Gr-1 PE (RB6-8C5_; anti-CD11b PerCP-Cy5 (M1/70); anti-CD11c APC (N418). All antibodies were acquired from eBioscience (San Diego, Calif.). The lung cells were counted to determine the total number of cells (the colon was not counted because we did not remove equal amounts of colon between samples). After staining for 20 mins the cells were washed and analyzed by FACS. Each data point shown in corresponding FIG. 5 represents the frequency of CD11b+ Gr-1+ cells in the live gate for one mouse. As shown in FIG. 5, treatment with *E. coli* antigenic compositions leads to an increased frequency of inflammatory monocytes in the colon of treated mice.

Figure 6A:
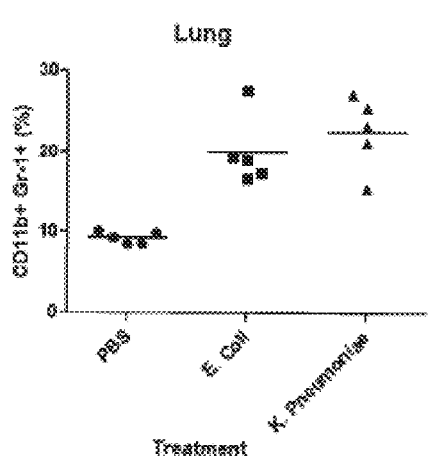
FIGS. 6A and 6B show the relative frequency of CD11b+ Gr-1+ cells detected from the lungs of mice treated with either *K. pneumoniae* or *E. coli* antigenic compositions or with PBS control.
Figure 6B:
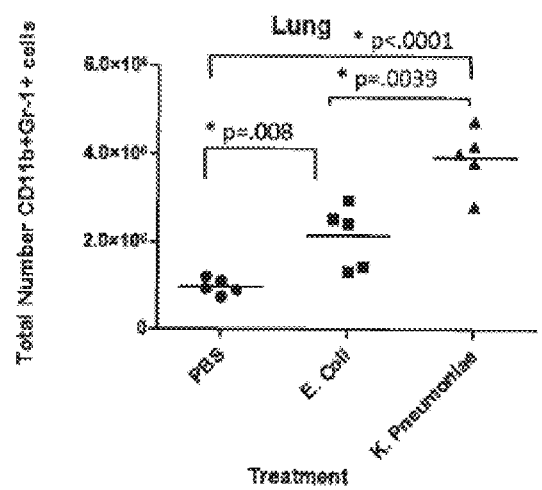

Further, and as shown in FIGS. 6A to 6B, when monocytes in the lungs were examined based on the experimental methods detailed herein, it was found that while both *E. coli* and *K. pneumoniae* antigenic compositions increase the frequency of monocytes in the lungs of mice, *K. pneumoniae* antigenic compositions were more effective when counting for total numbers. Referring to FIGS. 6A to 6B, the left-most panel shows the frequency of CD11b+Gr-1+ (inflammatory monocyte) cells in the lungs; the right-most panel shows the total number of CD11b+Gr-1+ cells in the lung.

Example 3: Microbial Prophylaxis in Lungs

Example 3a: *Klebsiella pneumoniae*-Derived Antigenic Formulation (SSI) Protects Against *S. pneumoniae* Challenge in the Lungs This Example illustrates that a SSI preparation of whole killed *Klebsiella pneumonia* administered subcutaneously in mice induced increases in circulating monocytes and provides protection against subsequent bacterial challenge with *Streptococcus pneumoniae* introduced into the nasopharynx. *Streptococcus pneumoniae*, or pneumococcus, is a Gram-positive, alpha-hemolytic, aerobic member of the order Lactobacillales. In contrast, *Klebsiella pneumoniae* is a Gram-negative, non-motile, encapsulated, lactose-fermenting, facultative anaerobe member of the order Enterobacteriales. These organisms are classified in distinct taxonomic phyla.

C57BL/6 mice were pretreated by subcutaneously injection with placebo or the *Klebsiella pneumonia* formulation every other day for three weeks, then challenged with $1 \times 10^9$ CFU of *S. pneumonia* P1547 and monitored for 5 days for signs of clinical infection. On day 5, mice were sacrificed (moribund mice were sacrificed before day 5) and evaluated for bacterial load and immune parameters.

Figure 7A:
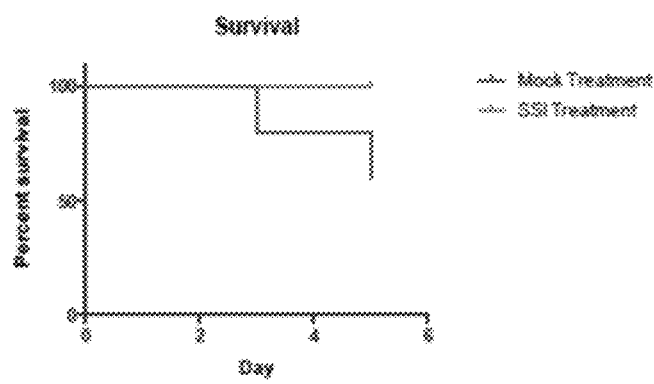
FIGS. 7A to 7E illustrate microbial prophylaxis as discussed in Example 3, in which treatment with a composition comprising whole killed *K. pneumoniae* cells provides protective immunity against subsequent challenge by *S. pneumoniae*.
Figure 7B:
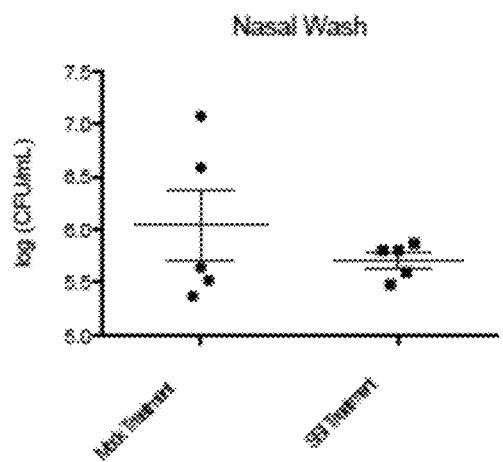
Figure 7C:
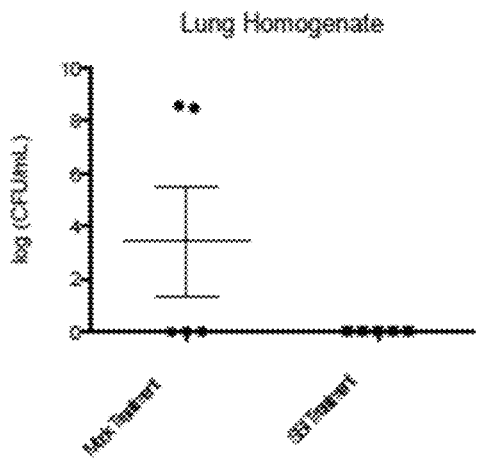
Figure 7D:
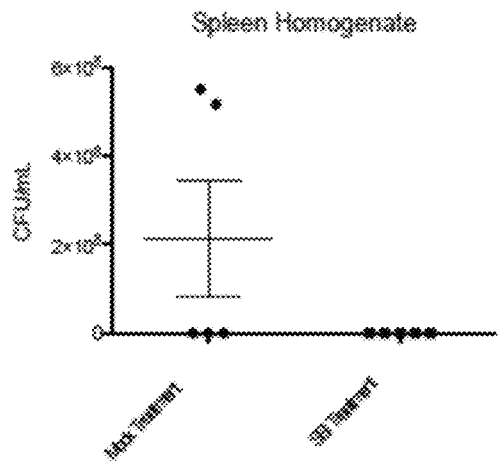
Figure 7E:
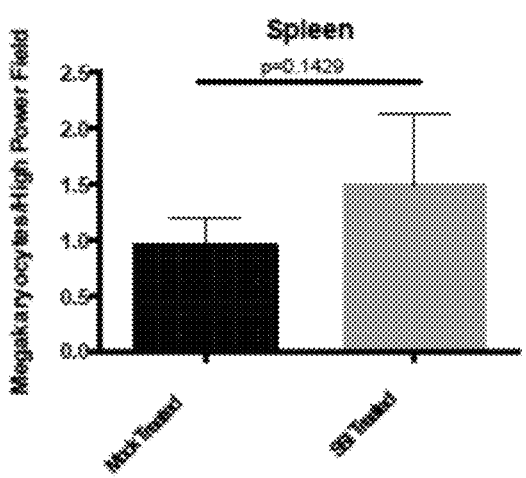

As illustrated in FIG. 7A, mice treated with the *Klebsiella pneumonia* formulation were protected from *S. pneumonia* infection (5/5) whereas placebo-treated mice were only partially protected (3/5). Furthermore, TNF and MCP-1 gene expression in lungs of resistant mice (both SSI- and placebo-treated) were higher than placebo-treated mice that succumbed to infection. FIG. 7B illustrates reduced bacterial counts in nasal cavity, lungs, and spleen with the SSI treatment.

Example 3b: *Klebsiella pneumoniae*-Derived Antigenic Formulation (SSI) Protects Against *P. aeruginosa* or *S. pneumoniae* Challenge in the Lungs

Figure 9A:
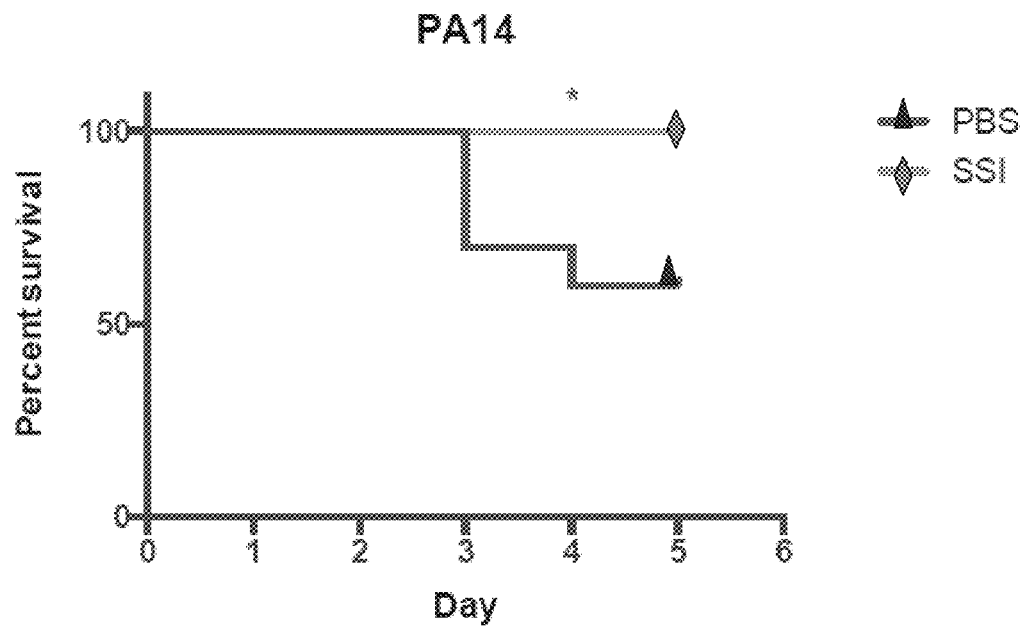
FIGS. 9A and 9B illustrate heterologous anti-microbial therapy in a mouse model, as discussed in Example 3, in which treatment with a composition comprising whole killed *Klebsiella pneumonia* cells is effective in ameliorating a lung infection caused by *Pseudomonas aeruginosa* (PA14).
Figure 9B:
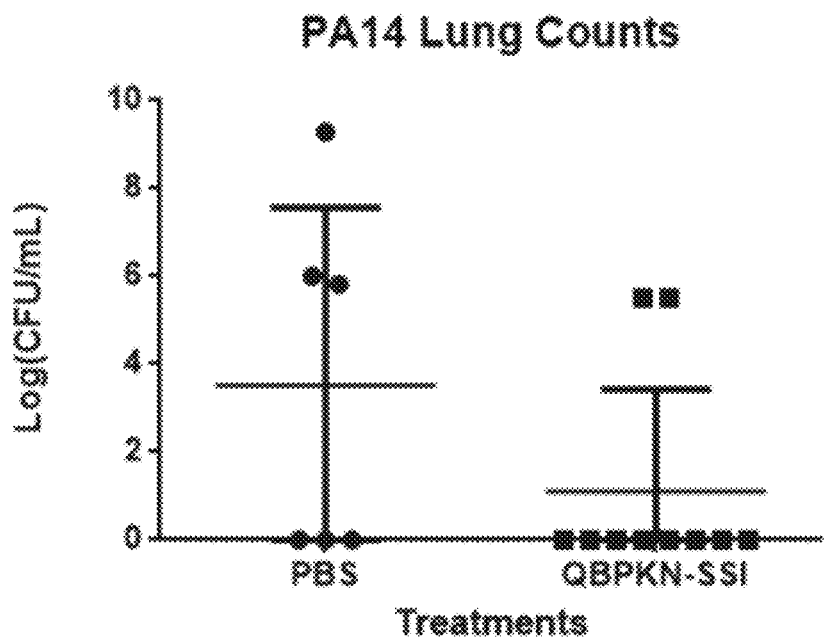

*Pseudomonas aeruginosa* (PA14, $7.8 \times 10^8$ CFU/mouse) was instilled into lungs of 8-10 week old C57131/6 mice pretreated with 30 µL PBS or an SSI formulated from whole killed *Klebsiella pneumoniae* every other day for 3 weeks, with survival as shown in FIG. 9A. Of the 6 surviving mice at day 5, 3/6 of the PBS treated group had bacteria in the lungs and only 2/10 SSI treated mice had bacteria in the lungs, as shown in FIG. 9B.

Figure 10:
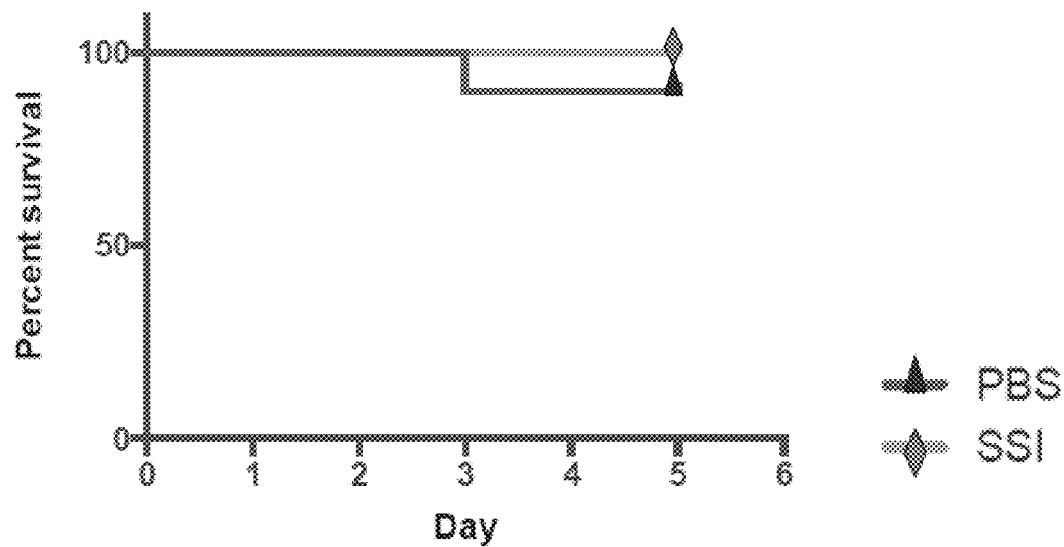
FIG. 10 illustrates heterologous anti-microbial therapy in a mouse model, as discussed in Example 3, in which treatment with a composition comprising whole killed *Klebsiella pneumonia* cells is effective in ameliorating a lung infection caused by *Streptococcus pneumoniae* (P1542).

*Streptococcus pneumoniae* (P1542, $4.1 \times 10^6$ CFU/mouse) was instilled into lungs of 8-10 wo C57Bl/6 mice pretreated with 30 µL PBS or an SSI formulated from whole killed *Klebsiella pneumoniae* every other day for 3 weeks, with survival as shown in FIG. 10.

This Example illustrates that a SSI preparation of whole killed *Klebsiella pneumonia* administered subcutaneously in mice induces prophylactic antimicrobial activity against infection in the lungs with *Pseudomonas aeruginosa* or *S. pneumoniae*. FIGS. 9A to 9B illustrate significantly enhanced survival in a *Pseudomonas aeruginosa* challenge, and FIG. 10 illustrates enhanced survival in a *S. pneumoniae* challenge. These data illustrate prophylaxis mediated by an antigenic composition of one lung pathogen, effective against two heterologous lung pathogens.

Example 3c: Comparison of *Klebsiella pneumoniae*-Derived Antigenic Formulation (SSI) and *E. coli*-Derived Antigenic Formulation (SSI) in Protecting Against *S. pneumoniae* or *P. aeruginosa* Challenge in the Lungs In this Example, *Klebsiella pneumoniae* SSI (QBKPN) demonstrated statistically superior efficacy in prophylaxis compared to the *E. coli* SSI (QBECO), in protecting against *S. pneumoniae* or *P. aeruginosa* challenge in the lungs.

Figure 15:
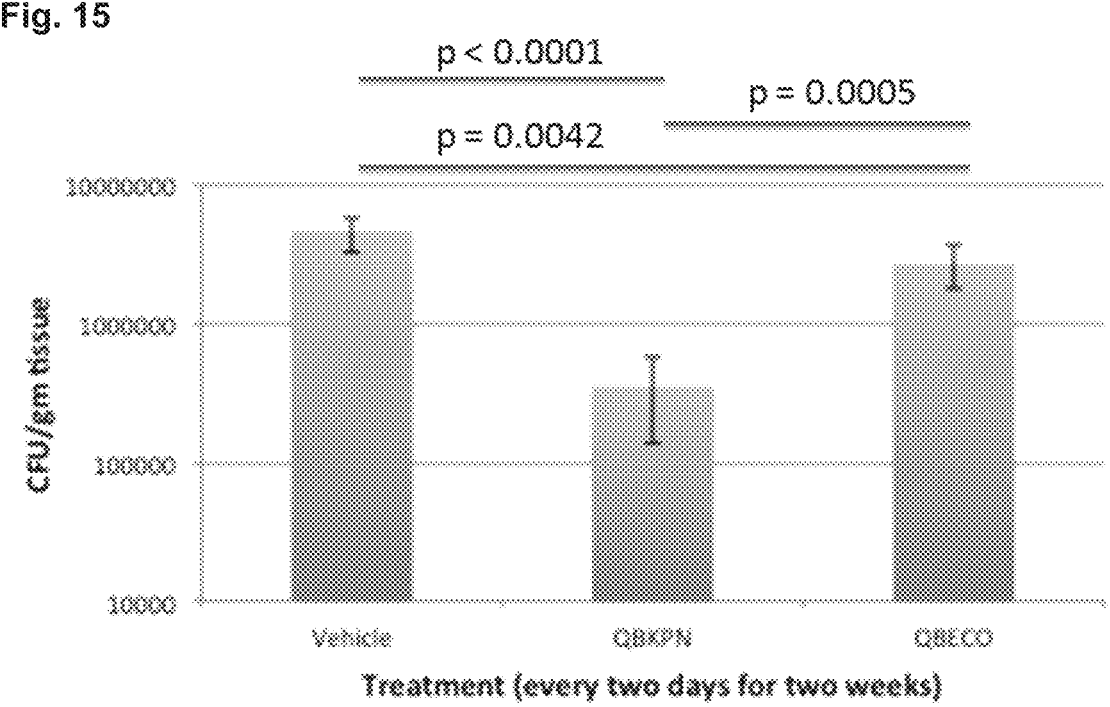
FIG. 15 is a bar graph illustrating heterologous anti-microbial therapy in a mouse model, as discussed in Example 3c, illustrating *Klebsiella pneumoniae* SSI (QBKPN) demonstrated statistically superior efficacy in prophylaxis compared to the *E. coli* SSI (QBECO), in protecting against *P. aeruginosa* challenge in the lungs.

For the model treatment of *P. aeruginosa*, mice were treated with the indicated SSI (0.03 ml/injection) for 14 days, then challenged with *Pseudomonas aeruginosa* (PA14) by intranasal instillation of $6.0 \times 10^8$ CFU of bacteria. Three days later, lungs were aseptically resected, homogenized, and assessed for bacterial load using *Pseudomonas* selection agar plates. FIG. 15 shows the results (data are CFU/g of lung (mean+/- std dev), illustrating *Klebsiella pneumoniae* SSI (QBKPN) demonstrated statistically superior efficacy in prophylaxis compared to the *E. coli* SSI (QBECO), in protecting against *P. aeruginosa* challenge in the lungs.

Figure 16:
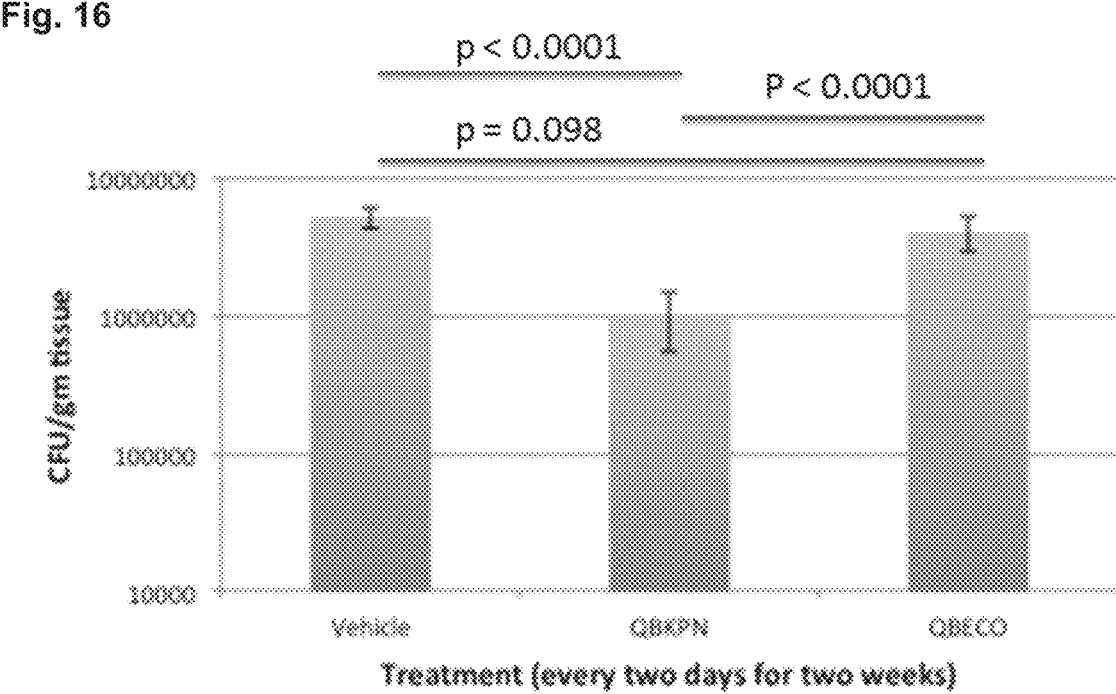
FIG. 16 is a bar graph illustrating heterologous antimicrobial therapy in a mouse model, as discussed in Example 3c, illustrating *Klebsiella pneumoniae* SSI (QBKPN) demonstrated statistically superior efficacy in prophylaxis compared to the *E. coli* SSI (QBECO), in protecting against *S. pneumoniae* challenge in the lungs.

For the model treatment of *S. pneumoniae*, mice were treated with the indicated SSI (0.03 ml/injection) for 14 days, then challenged with *Streptococcus pneumoniae* (PA14) by intranasal instillation of $5.0 \times 10^5$ CFU of bacteria. Three days later, lungs were aseptically resected, homogenized, and assessed for bacterial load using *Pseudomonas* selection agar plates. FIG. 16 shows the results (data are CFU/g of lung (mean+/− std dev), illustrating *Klebsiella pneumoniae* SSI (QBKPN) demonstrated statistically superior efficacy in prophylaxis compared to the *E. coli* SSI (QBECO), in protecting against *S. pneumoniae* challenge in the lungs.

Example 4: Antimicrobial Therapy in GIT

This example illustrates heterologous anti-microbial therapy in a mouse model of inflammatory bowel disease that uses a specific species (NRG 857) of Adherent Invasive *E. coli* (AIEC) to induce a chronic IBD-like infection in the colon in the 129e strain of mice that have a reduced ability to clear AIEC.

Figure 8A:
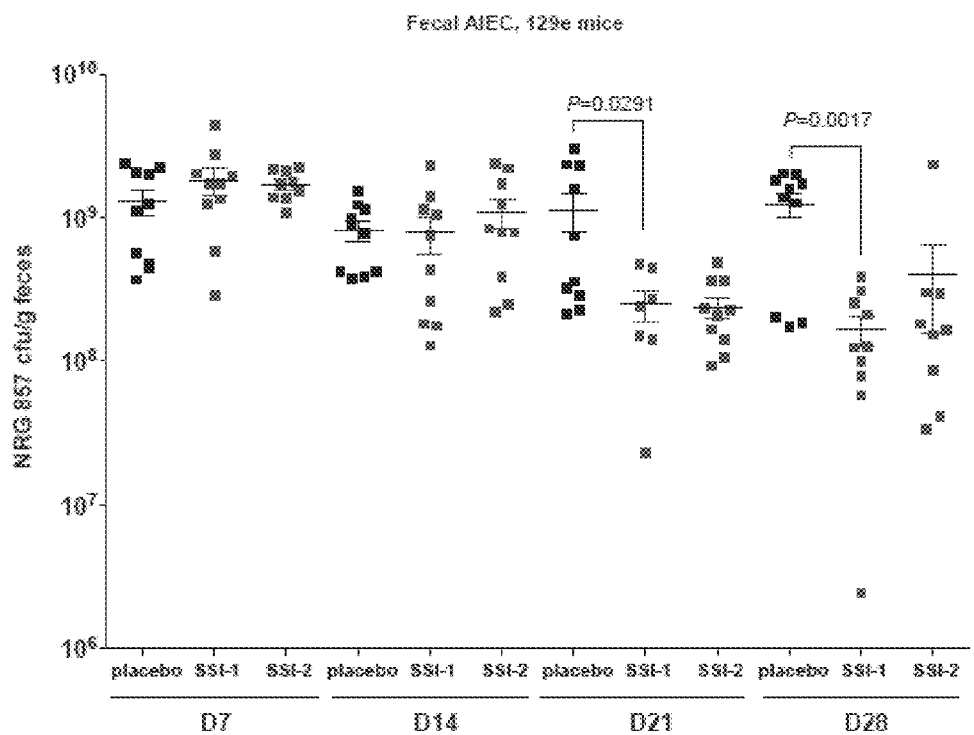
FIGS. 8A and 8B illustrate heterologous anti-microbial therapy in a mouse model, as discussed in Example 4, in which treatment with a composition comprising whole killed *E. coli* cells is effective in ameliorating an infection caused by a heterologous strain of adherent invasive *E. coli*.
Figure 8B:
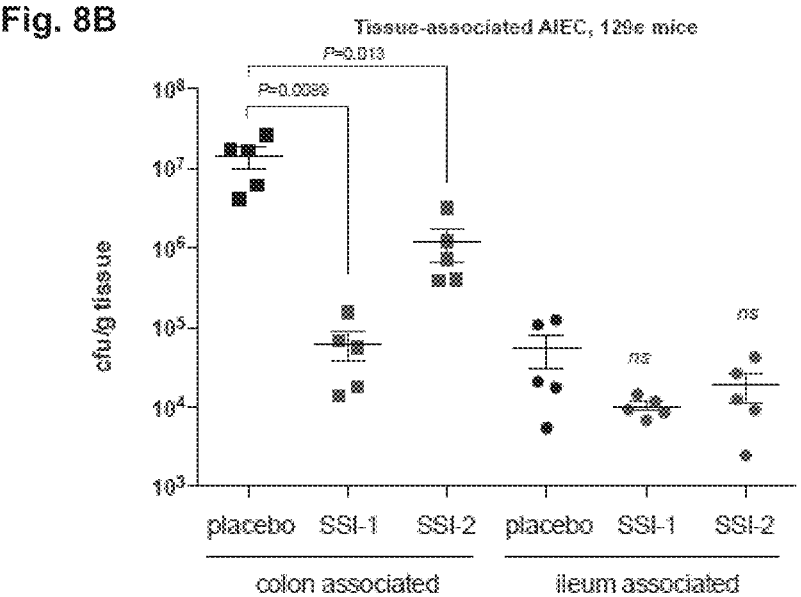

The 129e mice were infected with NRG 857 and treated with either (1) placebo, (2) a whole killed cell formulation of *E. coli* (SSI-1 in FIG. 8A to 8B), or (3) a whole killed cell formulation of *S. enterica*, which is an exogenous pathogen which can cause gastrointestinal infection in mice (referred to as SSI-2 in FIG. 8). The results illustrate that the whole killed formulation of *E. coli* was effective in reducing counts of NRG 857 in colon tissue (300 times less than placebo treated mice—note that the graph is a logarithmic scale) and feces of 129e mice. In addition, the *S. enterica* formulations also exhibited some anti-microbial activity against the heterologous AIEC infection.

In accordance with one aspect of the invention, macrophage defect or deficiency, leading to a reduced ability to clear bacterial infection and necrotic debris, may be the underlying trigger for some pathologies associated with microbial infections. This has for example been postulated to be the case in Crohn's disease. Aspects of the invention accordingly involve the induction of organ specific macrophage recruitment and activation, resulting in clearance of bacterial infection.

Example 5: Antimicrobial Prophylaxis in Peritoneal Cavity

Figure 11A:
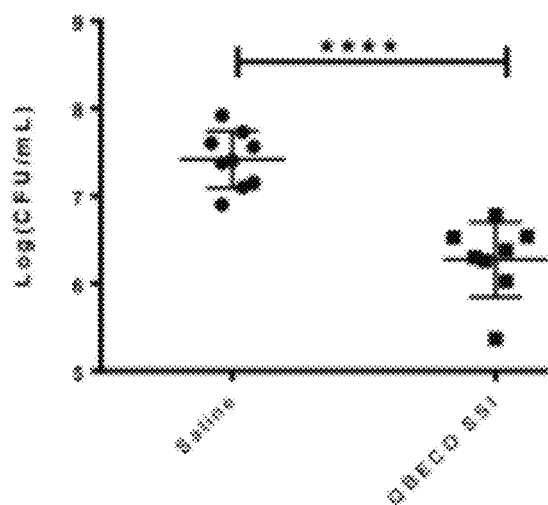
FIGS. 11A and 11B illustrate heterologous anti-microbial therapy in a mouse model, as discussed in Example 5, in which treatment with a composition comprising whole killed *E. coli* cells is effective in ameliorating a peritoneal infection caused by *S. enterica*.
Figure 11B:
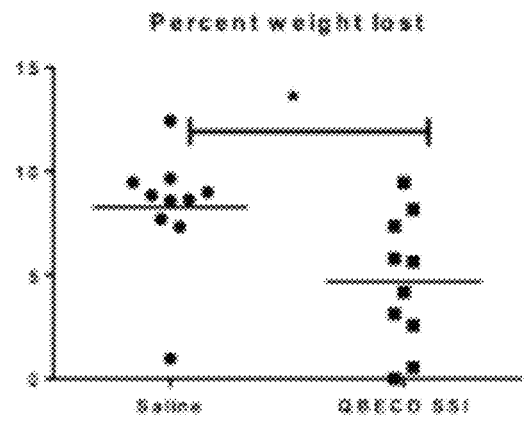

In a first aspect, this example illustrates that a whole killed *E. coli* SSI formulation is effective in protecting against a *S. enterica*. As illustrated in FIGS. 11A to 11B, SSI treated mice had significantly fewer bacteria in the spleen than saline treated mice (p<0.0001), and SSI treated mice had less peak weight loss than saline treated mice (p<0.02).

Figure 12A:
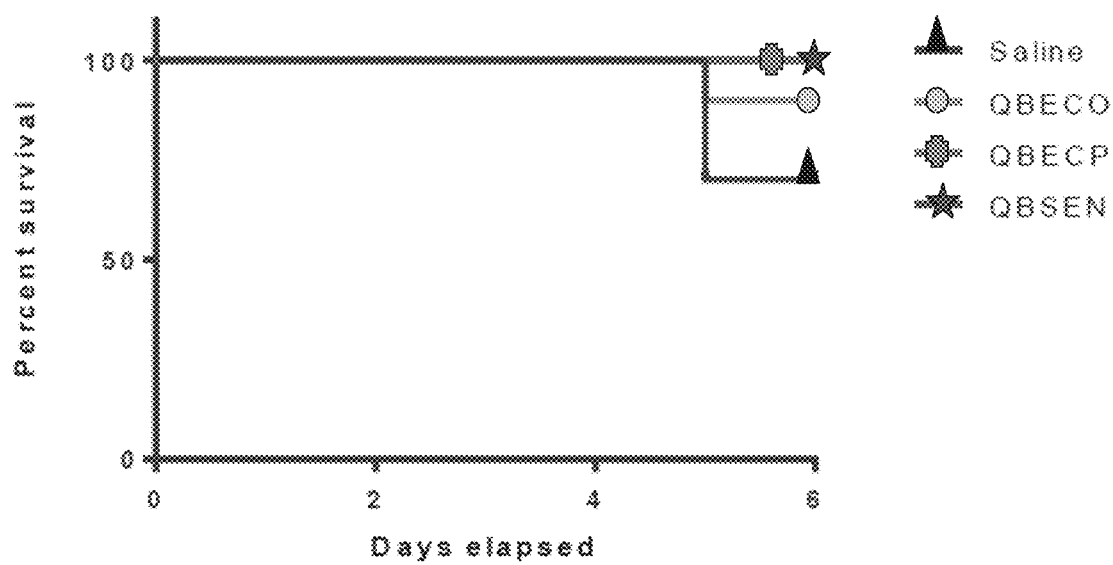
FIGS. 12A, 12B and 12C illustrate heterologous anti-microbial therapy in a mouse model, as discussed in Example 5, in which the effectiveness of treatments with two different compositions comprising alternative strains of whole killed *E. coli* cells is compared to a treatment with an antigenic *S. enterica* composition in ameliorating a peritoneal infection caused by *S. enterica*.
Figure 12B:
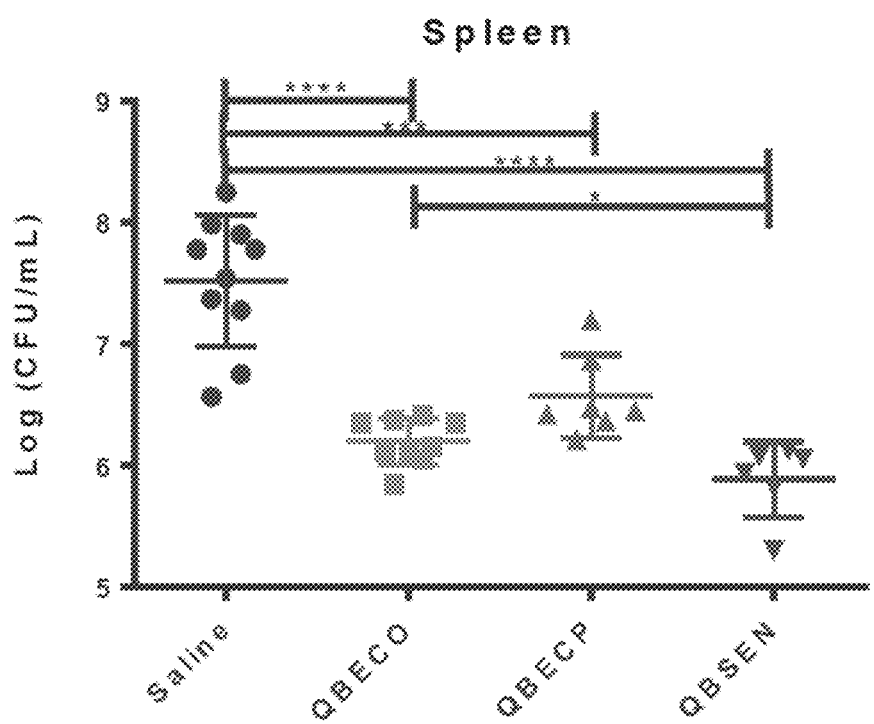
Figure 12C:
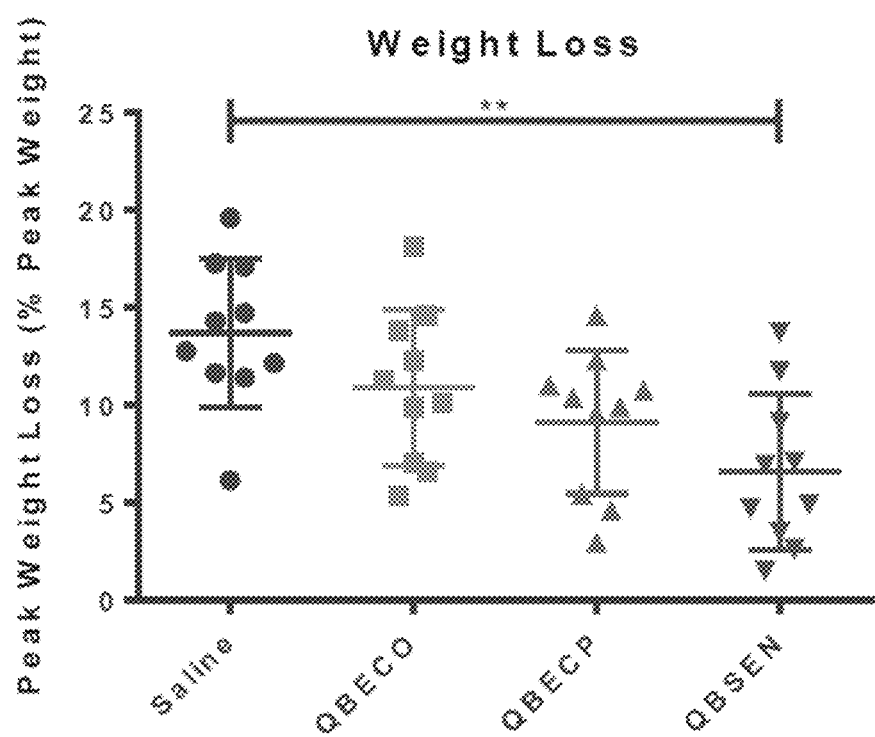

In an alternative aspect, this Example illustrates that two alternative whole killed *E. coli* SSI formulations (QBECO and QBECP), made from different strains of *E. coli*, are effective in a mouse model in protecting against a *S. enterica* challenge, with levels of prophylaxis that compare favourably to prior administration of an antigenic *S. enterica* formulation (QBSEN). In this Example, mice were pretreated by skin injection with the alternative formulations, QBECO, QBECP (SSI from urologic *E. coli*), or QBSEN (each given every other day for 3 weeks) and then infected with *S. enterica*. Survival was improved for all treatments, with QBECP providing comparable benefit to QBSEN, as illustrated in FIG. 12A. Mice were sacrificed, and colony counts in the spleen were quantitated and found to be lower in all the treated groups, as illustrated in FIG. 12B. Similarly, weight loss was found to be lower in all the treated groups, as illustrated in FIG. 12C.

Figure 19:
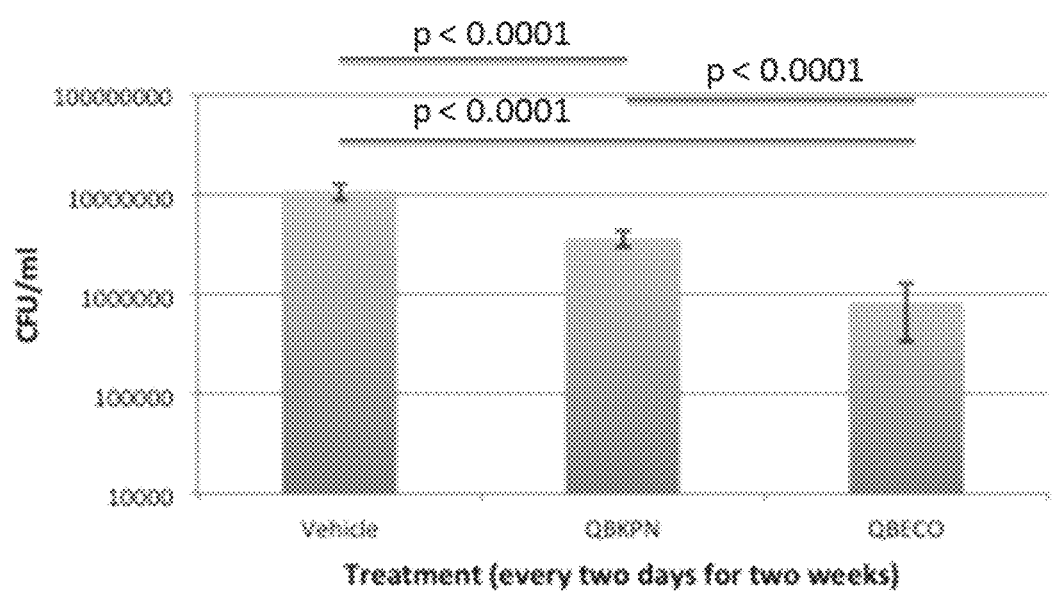
FIG. 19 illustrates antimicrobial prophylaxis in the peritoneal cavity, with a graph illustrating that both QBECO and QBKPN SSIs are protective, as measured by bacterial load in the spleen, with counts in mice treated with QBECO bing significantly lower than mice treated with QBKPN (data are CFU/ml (mean+/− std dev).

In a further illustration of targeted and optimized intraperitoneal (IP) prophylaxis, mice were treated with alternative SSIs, QBKPN and QBECO, or vehicle; then challenged with *Salmonella enterica* (*typhimurium*) by IP instillation of $1.0 \times 10^6$ CFU of bacteria. Three days later, spleens were aseptically resected, homogenized, and assessed for bacterial load on Hektoen enteric agar plates. FIG. 19 illustrates that both QBECO and QBKPN are protective, as measured by bacterial load in the spleen, and counts in mice treated with QBECO are significantly lower than mice treated with QBKPN (data are CFU/ml (mean+/− std dev).

Example 6: Antimicrobial Prophylaxis in Skin

Figure 13:
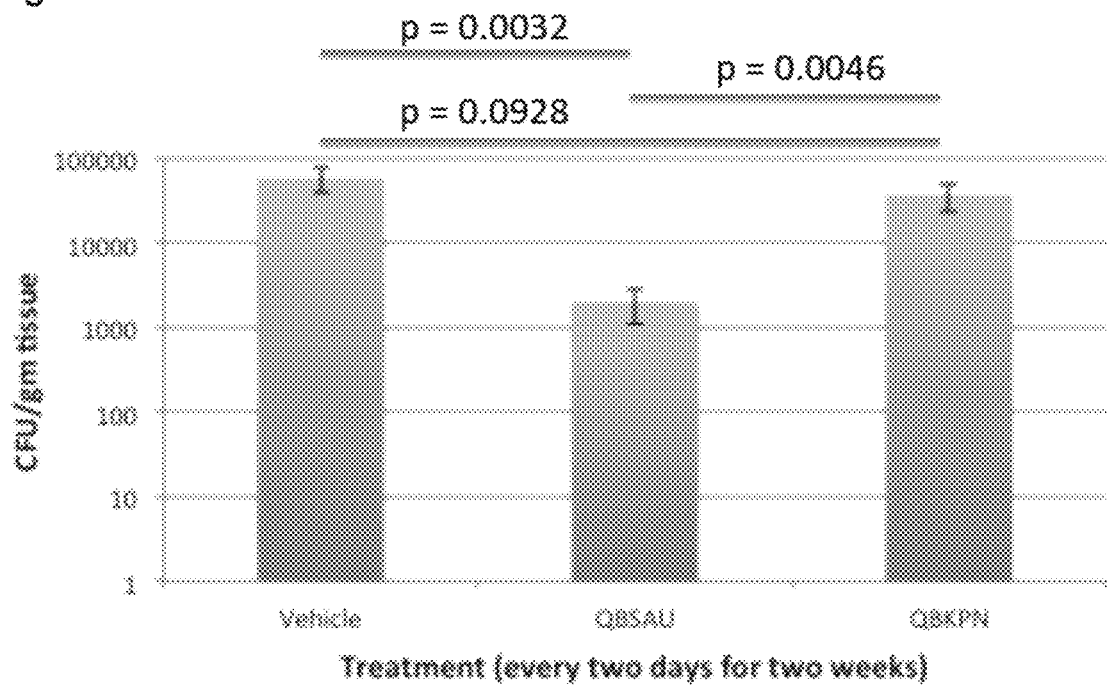
FIG. 13 is a bar graph illustrating heterologous anti-microbial therapy in a mouse model, as discussed in Example 6, in which the effectiveness of a *S. aureus*-derived SSI (QBSAU) is shown against *P. aeruginosa* challenge in skin, with significantly reduced *P. aeruginosa* bacterial counts following QBSAU pretreatment.
Figure 14:
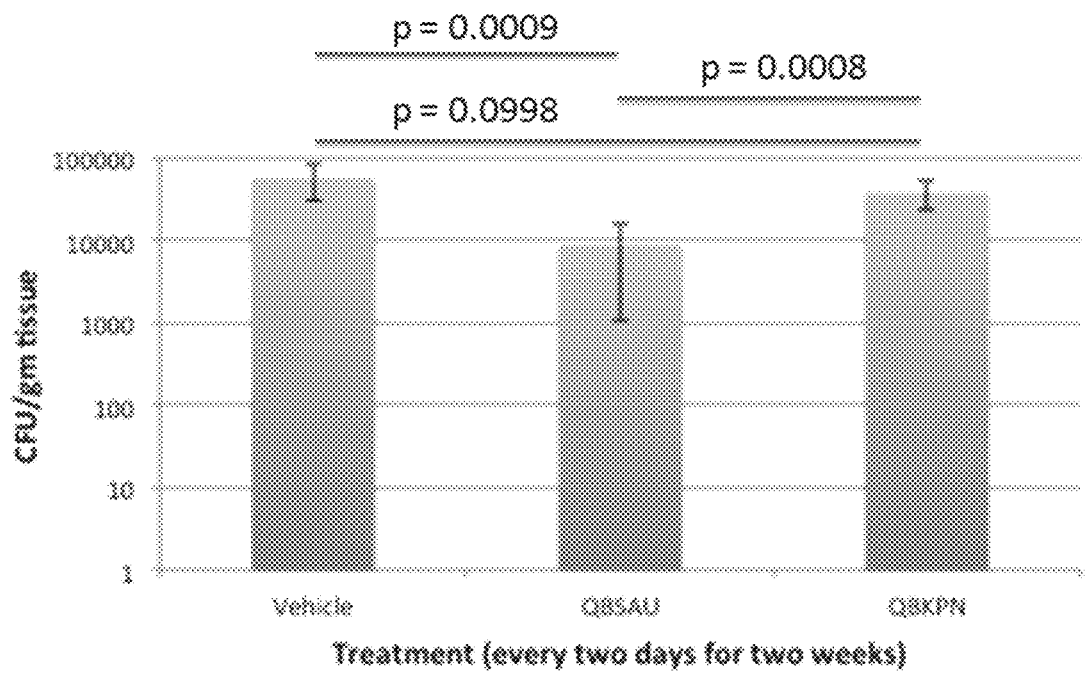
FIG. 14 is a bar graph illustrating heterologous anti-microbial therapy in a mouse model, as discussed in Example 6, repeating and confirming the data shown in FIG. 13, in which the effectiveness of a *S. aureus*-derived SSI (QBSAU) is shown against *P. aeruginosa* challenge in skin, with significantly reduced *P. aeruginosa* bacterial counts following QBSAU pretreatment.

This example illustrates targeted heterologous anti-microbial therapy in a mouse model of skin infection, illustrating the improved efficacy of antigenic formulations derived from microbial pathogens of the target tissue. Mice were treated with selected antigenic formulations of the invention (0.03 ml/injection) for 14 days, then challenged with *Pseudomonas aeruginosa* (PA14) by intradermal injection of $6.5 \times 10^5$ CFU. Three days later, skin was aseptically resected, homogenized, and assessed for bacterial load using *Pseudomonas* selection agar plates. FIG. 13 illustrates that QBSAU (*S. aureus*-derived SSI) protects against *P. aeruginosa* challenge in skin, with significantly reduced bacterial counts following QBSAU, compared to QBKPN (which is not a skin pathogen in the murine model). A repeat iteration of the foregoing procedure replicated the results, as shown in FIG. 14 (n=8 mice/group).

Example 7: Antimicrobial Prophylaxis in Geriatric Model Aged Mice

Figure 17A:
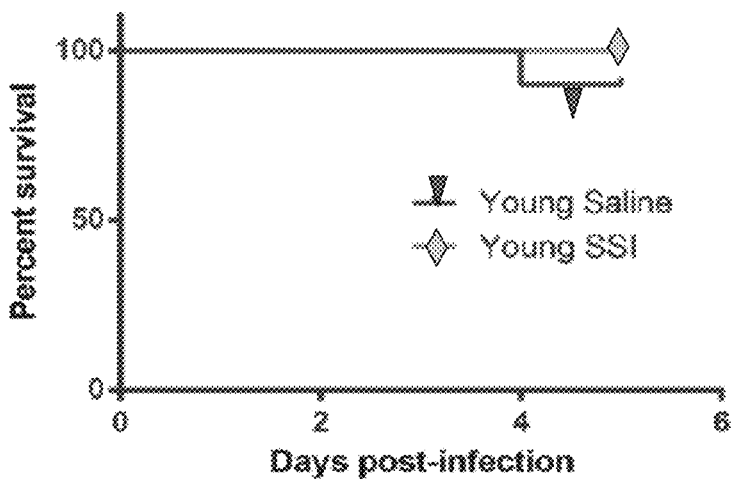
FIGS. 17A and 17B are two graphs showing targeted heterologous anti-microbial therapy in a geriatric mouse model of lung infection, showing that *Klebsiella pneumoniae* SSI (QBKPN) protects against *S. pneumoniae* challenge in lungs of aged mice. Survival benefit for old mice, FIG. 17B, was more pronounced than for young mice, FIG. 17A.
Figure 17B:
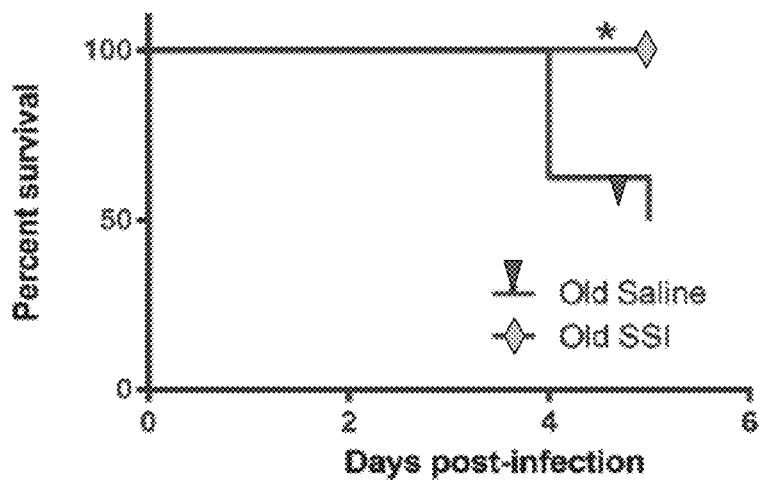

This example illustrates targeted heterologous anti-microbial therapy in a geriatric mouse model of lung infection, showing that *Klebsiella pneumoniae* SSI (QBKPN) protects against *S. pneumoniae* challenge in lungs of aged mice. FIGS. 17A to 17B show that the survival benefit for old mice, FIG. 17B, was more pronounced than for young mice, FIG. 17A. FIG. 18 illustrates corroborative data, showing that QBKPN reduces weight loss in aged mice, following challenge with *S. pneumoniae*, and this benefit is greater for aged mice compared to young mice.

Example 8: Antiviral Prophylaxis in Lungs

In this Example, mice wherein injected with QBKPN or QBECO SSI, or vehicle for 14 days, in accordance with the protocol outlined in other Examples. Mice were then challenged intranasally with murine herpes virus 68 (MHV68), a virus that is genetically modified to drive a luciferase reporter. MHV68 is a model viral pathogen for studying lung infection. Three days after challenge, mice were injected with 300 micrograms of luciferin; 10 min later, mice were sacrificed, lungs resected, and imaged with a Xenogen IVIS imager. Luminescence in the lungs is an indicator of active viral infection and replication.

Pretreatment of mice with QBKPN SSI dramatically diminished the luminescence signal in lungs of mice, providing evidence of antiviral prophylaxis in lungs using targeted antigenic bacterial formulations. The same dramatic result was not observed for QBECO.

OTHER EMBODIMENTS

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. In some embodiments, the invention excludes steps that involve medical or surgical treatment. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method of modulating an immune system in a vertebrate host for the prophylactic [or therapeutic]treatment of infection by a first microbial pathogen in a target tissue, the method comprising:
    administering to the vertebrate host an effective amount of an antigenic formulation comprising antigenic determinants specific for a second heterologous microbial pathogen, wherein:
    the antigenic determinants are selected from the group consisting of whole cells or cell wall extracts;
    the first microbial pathogen is a microbial lung pathogen that is not a *Klebsiella pneumonia, Streptococcus pneumonia, Pseudomonas aeruginosa* or a viral lung pathogen, and the second heterologous microbial pathogen is a *Klebsiella pneumonia*, and the target tissue is the lung; and,
    wherein the administering comprises administering successive doses of the formulation at a dosage interval of at least one hour, so that two or more doses are administered over a period from 2 days to 1 month, over a dosage duration of at least one week.

2. The method of claim 1, wherein the first microbial pathogen is *Moraxella catarrhalis, Mycoplasma pneumoniae*, or *Haemophilus* influenza.

3. The method of claim 1, wherein the host is a human patient.

4. The method of claim 2, wherein the host is a human patient.

5. The method of claim 1, wherein the antigenic determinants comprise whole cells.

6. The method of claim 2, wherein the antigenic determinants comprise whole cells.

7. The method of claim 3, wherein the antigenic determinants comprise whole cells.

8. The method of claim 4, wherein the antigenic determinants comprise whole cells.

9. The method of claim 5, wherein the whole cells are killed.

10. The method of claim 6, wherein the whole cells are killed.

11. The method of claim 7, wherein the whole cells are killed.

12. The method of claim 8, wherein the whole cells are killed.

13. The method of claim 5, wherein the whole cells are attenuated.

14. The method of claim 6, wherein the whole cells are attenuated.

15. The method of claim 7, wherein the whole cells are attenuated.

16. The method of claim 8, wherein the whole cells are attenuated.

17. The method of claim 1, wherein the antigenic determinants comprise cell wall extracts.

18. The method of claim 2, wherein the antigenic determinants comprise cell wall extracts.

19. The method of claim 3, wherein the antigenic determinants comprise cell wall extracts.

20. The method of claim 4, wherein the antigenic determinants comprise cell wall extracts.

* * * * *

UNITED STATES PATENT AND TRADEMARK OFFICE
CERTIFICATE OF CORRECTION

PATENT NO. : 10,946,083 B2
APPLICATION NO. : 16/264040
DATED : March 16, 2021
INVENTOR(S) : Harold David Gunn et al.

Page 1 of 1

It is certified that error appears in the above-identified patent and that said Letters Patent is hereby corrected as shown below:

In the Specification

Replace "Example 10" with -- Example 1C -- (Column 2, Line 2); and

Replace "*Penicillium mameffei*" with -- *Penicillium marneffei* -- (Column 32, Line 14).

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*